(12) United States Patent
McGinley et al.

(10) Patent No.: US 11,998,257 B2
(45) Date of Patent: Jun. 4, 2024

(54) TECHNIQUES AND INSTRUMENTS FOR PLACEMENT OF ORTHOPEDIC IMPLANTS RELATIVE TO BONE FEATURES

(71) Applicant: McGinley Engineered Solutions, LLC, Casper, WY (US)

(72) Inventors: Joseph C. McGinley, Casper, WY (US); Matthew V. Russell, Casper, WY (US); Vincent Palazzolo, Casper, WY (US); Ben Warren, Glenrock, WY (US); Adam M. Johnson, Casper, WY (US)

(73) Assignee: MCGINLEY ENGINEERED SOLUTIONS, LLC, Casper, WY (US)

( * ) Notice: Subject to any disclaimer, the term of this patent is extended or adjusted under 35 U.S.C. 154(b) by 43 days.

(21) Appl. No.: 17/838,020

(22) Filed: Jun. 10, 2022

(65) Prior Publication Data

US 2022/0304732 A1     Sep. 29, 2022

Related U.S. Application Data

(60) Continuation of application No. 16/817,375, filed on Mar. 12, 2020, now abandoned, which is a (Continued)

(51) Int. Cl.
*A61B 17/88* (2006.01)
*A61B 17/56* (2006.01)
(Continued)

(52) U.S. Cl.
CPC ......... *A61B 17/8872* (2013.01); *A61B 17/56* (2013.01); *A61B 34/20* (2016.02);
(Continued)

(58) Field of Classification Search
CPC ............ A61B 17/1633; A61B 17/8872; A61B 17/162; A61M 25/09041
See application file for complete search history.

(56) References Cited

U.S. PATENT DOCUMENTS 502,798 A    8/1893  Wilbur
1,831,813 A   11/1931  Axel
(Continued)

FOREIGN PATENT DOCUMENTS

DE   102011056927 A1   6/2013
EP       3199112 A1    8/2017
(Continued)

*Primary Examiner* — Olivia C Chang
(74) *Attorney, Agent, or Firm* — HOLZER PATEL DRENNAN

(57) ABSTRACT

Methods and instruments for placement of orthopedic implants in bones of a patient. The placement may include selective placement of the implant relative to structure of the bone using a measurement system that may detect interfaces between layers of the bone. The orthopedic implants may be engaged by various embodiments of chucks. The chucks may include structure for engaging indexing features of a corresponding orthopedic implant to restrict movement of the implant relative to the chuck along a working axis. The chucks may allow for use of an instrument having a measurement system for accurate and repeatable placement of the implants using the instrument.

7 Claims, 58 Drawing Sheets

Related U.S. Application Data continuation of application No. 15/635,554, filed on Jun. 28, 2017, now Pat. No. 10,588,680, which is a division of application No. 15/336,202, filed on Oct. 27, 2016, now Pat. No. 10,390,869.

(60) Provisional application No. 62/247,022, filed on Oct. 27, 2015.

(51) Int. Cl.
*A61B 34/20* (2016.01)
*A61B 90/00* (2016.01)
*A61B 17/72* (2006.01)
*A61B 17/84* (2006.01)

(52) U.S. Cl.
CPC .............. *A61B 90/00* (2016.02); *A61B 90/06* (2016.02); *A61B 2017/564* (2013.01); *A61B 17/72* (2013.01); *A61B 17/846* (2013.01); *A61B 2034/2059* (2016.02); *A61B 2090/062* (2016.02); *A61B 2090/064* (2016.02)

(56) References Cited

U.S. PATENT DOCUMENTS

| | | |
|---|---|---|
| 2,883,891 A | 4/1959 | Shulters et al. |
| 3,804,544 A | 4/1974 | Adams |
| 4,014,621 A | 3/1977 | Johnson et al. |
| 4,063,356 A | 12/1977 | Hepworth |
| 4,157,231 A | 6/1979 | Phillips |
| 4,310,269 A | 1/1982 | Neu et al. |
| 4,329,092 A | 5/1982 | Poenitzsch et al. |
| 4,329,095 A | 5/1982 | Schmuck |
| 4,644,335 A | 2/1987 | Wen |
| 4,710,075 A | 12/1987 | Davison |
| 4,723,911 A | 2/1988 | Kurtz |
| 4,765,333 A | 8/1988 | Bray |
| 4,867,158 A | 9/1989 | Sugg |
| 4,951,690 A | 8/1990 | Baker |
| 5,013,194 A | 5/1991 | Wienhold |
| 5,014,793 A | 5/1991 | Germanton et al. |
| 5,022,798 A | 6/1991 | Eckman |
| 5,071,293 A | 12/1991 | Wells |
| 5,133,728 A | 7/1992 | Petersen |
| 5,139,376 A | 8/1992 | Pumphrey |
| 5,161,921 A | 11/1992 | Corsi |
| 5,277,799 A | 1/1994 | Bransch |
| 5,361,504 A | 11/1994 | Huang |
| 5,380,333 A | 1/1995 | Meloul et al. |
| 5,411,503 A | 5/1995 | Hollstien et al. |
| 5,533,842 A | 7/1996 | Johnson et al. |
| 5,538,423 A | 7/1996 | Coss et al. |
| 5,584,838 A | 12/1996 | Rona et al. |
| 5,599,142 A | 2/1997 | Fujimoto et al. |
| 5,613,810 A | 3/1997 | Bureller |
| 5,810,828 A | 9/1998 | Lightman et al. |
| 5,902,306 A | 5/1999 | Norman |
| 5,961,257 A | 10/1999 | Bettini et al. |
| 5,980,248 A | 11/1999 | Kusakabe et al. |
| 6,033,409 A | 3/2000 | Allotta |
| 6,081,741 A | 6/2000 | Hollis |
| 6,096,042 A | 8/2000 | Herbert |
| 6,342,057 B1 | 1/2002 | Brace et al. |
| 6,494,590 B1 | 12/2002 | Paganini et al. |
| 6,527,778 B2 | 3/2003 | Athanasiou et al. |
| 6,587,184 B2 | 7/2003 | Wuersch et al. |
| 6,665,948 B1 | 12/2003 | Kozin et al. |
| 6,786,683 B2 | 9/2004 | Schaer et al. |
| 6,925,725 B2 | 8/2005 | Herrmann et al. |
| 7,073,989 B2 | 7/2006 | Erickson et al. |
| 7,185,998 B2 | 3/2007 | Oomori et al. |
| 7,220,088 B2 | 5/2007 | Ferrari et al. |
| 7,235,940 B2 | 6/2007 | Bosch et al. |
| 7,314,048 B2 | 1/2008 | Couture et al. |
| 7,482,819 B2 | 1/2009 | Wuersch |
| 7,578,642 B2 | 8/2009 | Fritsche et al. |
| 7,681,659 B2 | 3/2010 | Zhang et al. |
| 7,691,106 B2 | 4/2010 | Schenberger et al. |
| 7,840,253 B2 | 11/2010 | Tremblay et al. |
| 7,946,049 B1 | 5/2011 | Wilton |
| 7,992,311 B2 | 8/2011 | Cerwin |
| 8,092,457 B2 | 1/2012 | Oettinger et al. |
| 8,162,074 B2 | 4/2012 | Cook |
| 8,167,518 B2 | 5/2012 | Mathis et al. |
| 8,171,642 B2 | 5/2012 | Fritsche et al. |
| 8,317,437 B2 | 11/2012 | Merkley et al. |
| 8,460,297 B2 | 6/2013 | Watlington et al. |
| 8,463,421 B2 | 6/2013 | Brett et al. |
| 8,511,945 B2 | 8/2013 | Apkarian et al. |
| 8,734,153 B2 | 5/2014 | Arzanpour et al. |
| 8,821,493 B2 | 9/2014 | Anderson |
| 8,894,654 B2 | 11/2014 | Anderson |
| 8,925,169 B2 | 1/2015 | Schevers |
| 8,970,207 B2 | 3/2015 | Baumgartner |
| 9,022,949 B2 | 5/2015 | Herndon |
| 9,114,494 B1 | 8/2015 | Mah |
| 9,204,885 B2 | 12/2015 | McGinley et al. |
| 9,358,016 B2 | 6/2016 | McGinley et al. |
| 9,370,372 B2 | 6/2016 | McGinley et al. |
| 9,492,181 B2 | 11/2016 | McGinley et al. |
| 9,855,060 B2 | 1/2018 | Ardel |
| 2001/0031919 A1 | 10/2001 | Strommer et al. |
| 2001/0047219 A1 | 11/2001 | Oden |
| 2002/0165549 A1 | 11/2002 | Owusu-Akyaw et al. |
| 2003/0049082 A1 | 3/2003 | Morrison et al. |
| 2003/0229351 A1 | 12/2003 | Tidwell et al. |
| 2004/0146367 A1 | 7/2004 | Gerhardt et al. |
| 2004/0179829 A1 | 9/2004 | Phillips et al. |
| 2004/0215395 A1 | 10/2004 | Strasser et al. |
| 2005/0116673 A1 | 6/2005 | Carl et al. |
| 2005/0131415 A1 | 6/2005 | Hearn et al. |
| 2005/0169717 A1 | 8/2005 | Field |
| 2005/0261870 A1 | 11/2005 | Cramer et al. |
| 2006/0004371 A1 | 1/2006 | Williams et al. |
| 2006/0008771 A1 | 1/2006 | Courvoisier |
| 2006/0025677 A1 | 2/2006 | Verard et al. |
| 2006/0074292 A1 | 4/2006 | Thomson et al. |
| 2006/0241628 A1 | 10/2006 | Parak |
| 2006/0258938 A1 | 11/2006 | Hoffman et al. |
| 2007/0030486 A1 | 2/2007 | Gelbart |
| 2007/0035311 A1 | 2/2007 | Wuersch |
| 2007/0041799 A1 | 2/2007 | Schaefer et al. |
| 2008/0119725 A1 | 5/2008 | Lloyd |
| 2008/0167653 A1 | 7/2008 | Watlington et al. |
| 2008/0226409 A1 | 9/2008 | Hasenzahl |
| 2008/0228195 A1 | 9/2008 | Von et al. |
| 2008/0243125 A1 | 10/2008 | Guzman et al. |
| 2008/0292416 A1 | 11/2008 | Kado et al. |
| 2009/0131986 A1 | 5/2009 | Lee et al. |
| 2009/0182226 A1 | 7/2009 | Weitzner et al. |
| 2009/0245956 A1 | 10/2009 | Apkarian et al. |
| 2009/0299439 A1 | 12/2009 | Saladino et al. |
| 2009/0326537 A1 | 12/2009 | Anderson |
| 2010/0114099 A1 | 5/2010 | Patwardhan |
| 2010/0137874 A1 | 6/2010 | Kim et al. |
| 2010/0239380 A1 | 9/2010 | Amirov et al. |
| 2010/0239830 A1 | 9/2010 | Ohnishi et al. |
| 2011/0020084 A1 | 1/2011 | Brett et al. |
| 2011/0060242 A1 | 3/2011 | Mrva et al. |
| 2011/0245831 A1 | 10/2011 | Giersch et al. |
| 2011/0245832 A1 | 10/2011 | Giersch et al. |
| 2011/0245833 A1 | 10/2011 | Anderson |
| 2011/0301611 A1 | 12/2011 | Garcia et al. |
| 2012/0037386 A1 | 2/2012 | Cook |
| 2012/0123418 A1 | 5/2012 | Giurgi et al. |
| 2012/0179070 A1 | 7/2012 | Pommer et al. |
| 2012/0253348 A1 | 10/2012 | Arlettaz et al. |
| 2013/0122466 A1 | 5/2013 | Connor et al. |
| 2013/0237811 A1 | 9/2013 | Mihailescu et al. |
| 2013/0304069 A1 | 11/2013 | Bono et al. |
| 2013/0307529 A1 | 11/2013 | Baumgartner |
| 2013/0327552 A1 | 12/2013 | Lovelass et al. |
| 2014/0039517 A1 | 2/2014 | Bowling et al. |
| 2014/0081659 A1 | 3/2014 | Nawana et al. |

(56) References Cited

U.S. PATENT DOCUMENTS

| | | |
|---|---|---|
| 2014/0107471 A1 | 4/2014 | Haider et al. |
| 2014/0275760 A1 | 9/2014 | Lee et al. |
| 2014/0275989 A1 | 9/2014 | Jacobsen et al. |
| 2014/0350685 A1 | 11/2014 | Bagga et al. |
| 2015/0066030 A1 | 3/2015 | McGinley et al. |
| 2015/0066035 A1 | 3/2015 | McGinley et al. |
| 2015/0066036 A1 | 3/2015 | McGinley et al. |
| 2015/0066037 A1 | 3/2015 | McGinley et al. |
| 2015/0066038 A1 | 3/2015 | McGinley et al. |
| 2015/0165580 A1 | 6/2015 | Holland |
| 2016/0120553 A1* | 5/2016 | Xie ............... A61B 17/162 606/80 |
| 2016/0178343 A1 | 6/2016 | Hale et al. |
| 2016/0247276 A1 | 8/2016 | Chou et al. |
| 2017/0143396 A1 | 5/2017 | McGinley et al. |
| 2017/0345398 A1 | 11/2017 | Fuchs et al. |
| 2018/0070113 A1 | 3/2018 | Phillips et al. |
| 2018/0110572 A1 | 4/2018 | Flatt |
| 2018/0260931 A1 | 9/2018 | Ozguner et al. |
| 2018/0325528 A1* | 11/2018 | Windolf ............ A61B 17/1622 |
| 2019/0209287 A1 | 7/2019 | Zenz-Olson |

FOREIGN PATENT DOCUMENTS

| | | |
|---|---|---|
| WO | 9724991 A1 | 7/1997 |
| WO | 2015006296 A1 | 1/2015 |
| WO | 2015014771 A2 | 2/2015 |
| WO | 2015034562 A1 | 3/2015 |
| WO | 2015082904 A1 | 6/2015 |
| WO | 2016207628 A1 | 12/2016 |

\* cited by examiner

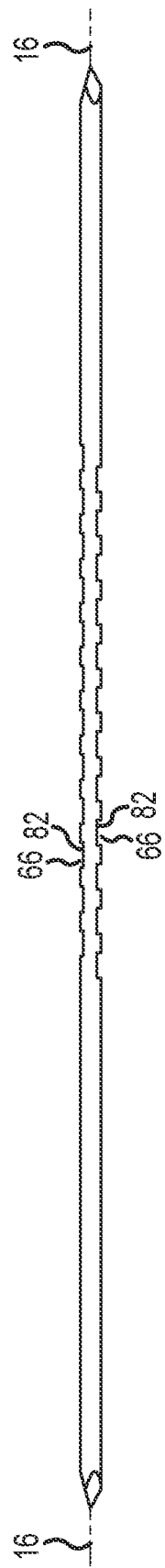

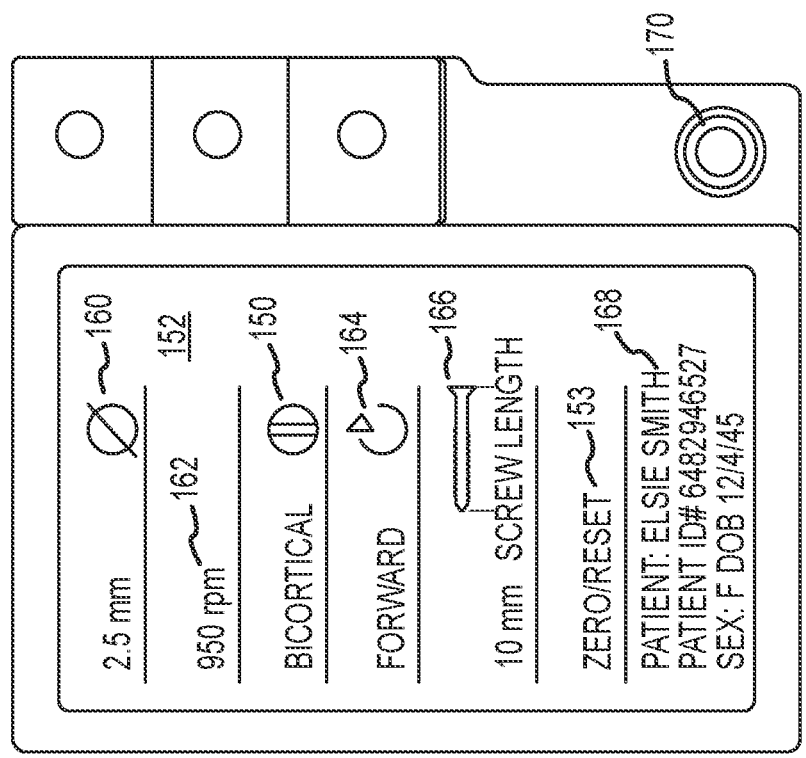
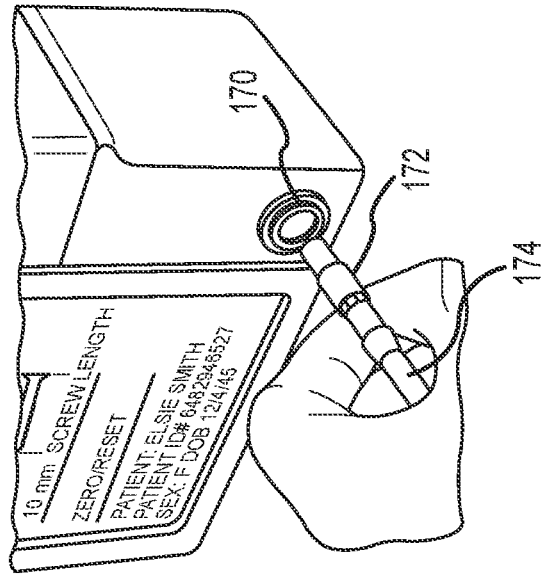
FIG. 36A
FIG. 36B

TECHNIQUES AND INSTRUMENTS FOR PLACEMENT OF ORTHOPEDIC IMPLANTS RELATIVE TO BONE FEATURES

RELATED APPLICATIONS

This application is a continuation of U.S. application Ser. No. 16/817,375 filed on Mar. 12, 2020, entitled "TECHNIQUES AND INSTRUMENTS FOR PLACEMENT OF ORTHOPEDIC IMPLANTS RELATIVE TO BONE FEATURES", is a continuation application of U.S. application Ser. No. 15/635,554, filed on Jun. 28, 2017, entitled "TECHNIQUES AND INSTRUMENTS FOR PLACEMENT OF ORTHOPEDIC IMPLANTS RELATIVE TO BONE FEATURES", which is a divisional application of U.S. application Ser. No. 15/336,202, filed on Oct. 27, 2016, entitled "TECHNIQUES AND INSTRUMENTS FOR PLACEMENT OF ORTHOPEDIC IMPLANTS RELATIVE TO BONE FEATURES", which claims the benefit of U.S. Provisional Patent Application No. 62/247,022 filed Oct. 27, 2015, entitled "SYSTEM AND METHOD FOR PLACEMENT OF ORTHOPEDIC IMPLANTS RELATIVE TO BONE FEATURES," which is incorporated herein by reference in its entirety.

FIELD

The present disclosure generally relates to the field of surgical tools, and specifically to surgical tools for use in placement of orthopedic implants relative to the bone of a patient.

BACKGROUND

Often times it is necessary during orthopedic surgical operations to place an implant relative to a bone of a patient. Such orthopedic implants may include transcutaneous pins (e.g., intra medullary (IM) pins), wires (e.g., Kirschner wires (K-wires)), or other implants. For instance, such implants may be used for pin fixation of bones, in connection with skeletal traction, or for other purposes. In any regard, placement of such implants may involve significant time, effort, and skill on the part of a surgeon.

For instance, depending upon the nature of the operation and/or purpose of the implant, it may be necessary to dispose the distal tip of the implant at various locations relative to the structure of the bone of the patient. Furthermore, it may be necessary to create boxes or use other tools in connection with placement of an orthopedic implant. In doing so, the surgeon is left to judge such placement based solely upon the feel or perception of the surgeon. As the implants may be placed using powered tools such as pneumatic or electric drills or the like, the placement of an implant often results in added time and complexity to an orthopedic operation. Moreover, as the surgeon's feel or perception is relied on for accurate placement, the potential exists for the implant to be misplaced. Furthermore, having an implant pass completely through the bone in which it is to be placed may also result in damage to the issue surrounding the bone. In any event, the placement of orthopedic implants may present complications that may result in increased time, cost, or risk to surgical procedures.

SUMMARY

In view of the foregoing, the present disclosure is generally directed to the use of an instrument having a measurement system to place orthopedic implants with improved reliability and accuracy. Specifically, the measurement system may be operable to automatically determine (e.g., based on one or more sensors of the measurement system) when the orthopedic implant (e.g., a leading edge thereof) passes through interfaces of various anatomical structures in a bone of the patient. As such, an orthopedic implant may be placed based on the sensed position of the implant by the measurement system. Further still, in connection with the placement of a surgical instrument, other surgical tools (e.g., drills, saws, grinders, etc.) may also be used by a surgeon to assist in the operation. Accordingly, the measurement system as described herein may also or alternatively be used to determine the placement of a surgical tool (e.g., a drill, saw, burr, etc.) that may be used in an operation.

When using the instrument having a measurement system as described herein, a surgeon may be able to rely on an automatically determined position of the orthopedic implant without having to rely on simply "sensing" or "feeling" the location of the implant relative to the relevant anatomical structures. As the sensitivities of the various sensors of the instruments may be greater than that of the surgeon's senses alone, the position of an orthopedic implant may be more accurately and reliably placed relative to the anatomy of interest. Moreover, as use of a measurement system does not rely on a surgeon's "feel," placement of the orthopedic implant may be more repeatable.

In an embodiment of a measurement system described herein, a displacement sensor may be provided for use in determining the relative displacement of the orthopedic implant to a reference point. For instance, the reference point may be the exterior portion of the bone in which the implant is to be inserted. The displacement sensor may include a linear displacement sensor that is displaced relative to the orthopedic implant as the orthopedic implant is advanced into the bone of the patient. In this regard, it is advantageous to maintain the orthopedic implant stationary relative to the displacement sensor axially in relation to the working axis of the orthopedic implant (i.e., the axis about which the orthopedic implant is rotated and along which the orthopedic implant travels when advanced into the bone). That is, if the implant slips axially, the displacement measurement may be inaccurate. However, while the implant is to be maintained axially stationary relative to the displacement sensor during advancement, the nature of orthopedic implants may result in the need to release the implant from the instrument, retract of the instrument in a direction opposite the direction of advancement of the implant into the bone, and reengage the implant for further advancement. Also, the instrument may be released to retract the instrument from the implant once placed in the final position as desired.

Accordingly, the ability to selectively release the orthopedic implant from the instrument for retraction and/or reengagement may be provided. Such selective release of the orthopedic implant is preferably provided in an efficient and ergonomic manner as the operation of release and/or reengagement may occur frequently during an operation. As such, various chuck embodiments are described herein that may be used to selectively engage an orthopedic implant for use with an instrument.

At least some embodiments described herein may allow for engagement in orthopedic implant by a chuck of instrument without requiring (i.e., in the absence of) an external force be applied to the chuck by the user. For instance, many previously posed chucks used to engage orthopedic implants required a user to continuously maintain a force on the chuck (e.g., a trigger lever thereof) to maintain engagement of the chuck with the orthopedic implant. Such an arrangement that requires continuous application of an external force on the chuck by the user to maintain engagement of the orthopedic implant by the chuck may be disadvantageous in a number of ways. Initially, requiring a user to grasp and maintain an external force upon the chuck may diminish the user's ability to accurately and precisely control the instrument. For example, a user may be required to reach with the fingers of the hand used to grasp the handle of the instrument to apply the force on the chuck to maintain engagement of the orthopedic implant with the chuck. In contrast, the embodiments described herein that may allow for engagement of the chuck in the absence of an applied external force by the user may allow the user to more ergonomically grasp the handle of the instrument, thus promoting increased control over the instrument.

Additionally, as may be particularly relevant in the context of use of the chuck with an instrument having a measurement system as described herein, requiring the user to apply an external force to the chuck maintain engagement with the orthopedic implant may provide inaccuracies in relation to the measurement system. Initially, requiring a user to maintain a force on the chuck to engage the orthopedic implant with the chuck may increase the likelihood that the orthopedic implant slips with respect to the chuck. As may be appreciated, any such slippage between the orthopedic implant in the chuck may be detected by the measurement system as movement of the orthopedic implant relative to the bone. That is, slippage between the orthopedic implants in the chuck may result in inaccuracies in relation to the displacement sensor output of the measurement system described herein. However, utilization of a chuck that does not require external force to be applied to the chuck to maintain engagement with the orthopedic implant may reduce the possibility that the orthopedic implant slips with respect to the chuck because the user is not required to actively engage with the chuck to maintain engagement between the chuck and the orthopedic implant.

Further still, the measurement system described herein may utilize a force sensor capable of measuring the axial force acting on the orthopedic implant by transmitting such force through the chuck and/or drive system to a force sensor that is capable of measuring any such axial load. However, requiring a user to impart a force onto the chuck to maintain engagement between the chuck and the orthopedic implant may introduce erroneous forces acting on the chuck and/or drive system that may be detected by the force sensor and do not correspond to axial force experienced by the orthopedic implant as it is advanced relative to the bone of the patient. That is, the force imparted on the chuck by a user to maintain engagement between the chuck and the orthopedic implant may result in a noisy force signal that reduces the accuracy of the measurement system. In turn, utilization of a chuck that does not require an external force be applied to the chuck to maintain engagement between the orthopedic implant and the chuck may improve the accuracy of the measurement system.

In at least certain embodiments described herein, a chuck may be provided that allows for engagement of the orthopedic implant upon a motion of linear advancement of the orthopedic implant relative to the bone of the patient or upon a rotation of the chuck relative to the orthopedic implant. In this regard, upon advancement of the instrument to advance the orthopedic implant relative to the bone of the patient, the chuck may engage the orthopedic implant to limit relative axial movement between the orthopedic implant in the chuck that can be measured by the measurement system. However, retraction of the chuck relative to the orthopedic implant may be allowed such that the chuck disengages the orthopedic implant upon retraction of the chuck relative to the orthopedic implant such that the instrument may be retracted from the orthopedic implant. Similarly, the chuck may engage the orthopedic implant upon rotation of the chuck relative to the orthopedic implant (e.g., in a direction tending to drive the orthopedic implant into a bone of a patient). However, upon counter rotation of the chuck relative to the orthopedic implant, the orthopedic implant may be disengaged by the chuck such that the instrument may be retracted relative to the orthopedic implant. Further still, such chuck embodiments may provide various different states of engagement of the orthopedic implant. For example, the foregoing description of a particular advancement of the chuck relative to the orthopedic implant to cause engagement may be provided in a biased state of the chuck. Furthermore, a locked open state of the chuck may be provided whereby the orthopedic implant is not engaged by the chuck even upon advancement of the chuck relatively orthopedic implant in a manner that would otherwise engage the orthopedic implant when the chuck is in the biased state of the chuck. Additionally, a locked closed state of the chuck may be provided whereby the orthopedic implant may be engaged regardless of whether the chuck is advanced or retracted and/or regardless of how the chuck is rotated relative to the orthopedic implant.

In one particular embodiment, the chuck and orthopedic implant may be coordinately provided such that the chuck may engage one or more of a plurality of indexing features provided on the orthopedic implant. In this regard, the orthopedic implant may be engaged at known relative positions along the orthopedic implant relative to (e.g., along) the working axis. This may assist in determining the distance that the orthopedic implant has been advanced into the bone of the patient. The coordinated engagement between a chuck and one or more of the plurality of indexing members may also help to reduce the potential for axial slipping of the orthopedic implant relative to the chuck as the implant is advanced. Notably, the engagement may maintain the orthopedic implant in an axial position relative to the displacement sensor without the presence of external forces acting on the chuck to maintain the implant in place. For instance, in contrast to prior proposed chuck designs that rely on a user gripping a lever or otherwise actuating the chuck to maintain the engagement with the orthopedic implant, the use of a chuck as described herein that engages an indexing portion may alleviate the need for such user intervention to maintain external forces acting on the chuck to maintain engagement with the orthopedic implant. This may also allow for improved accuracy in measurement of forces acting axially on the orthopedic implant.

In certain embodiments described herein, a chuck may also be provided with an implant holder to reduce axial and/or rotational movement of the orthopedic implant relative to the chuck when the orthopedic implant is not engaged with the chuck jaws. For example, there may be instances when the chuck jaws will not be engaged with the orthopedic implant, but it may still be desired that the orthopedic implant not slide or rotate about the working axis (e.g., to prevent the orthopedic implant from slipping under the influence of gravity). For instance, upon initial introduction of the orthopedic implant relative to the chuck, the user may desire the orthopedic implant to remain stationary absent an application of an external force to the orthopedic implant prevent the orthopedic implant from sliding from the instrument (e.g., under the influence of gravity). In this context leading up to engagement by the chuck jaws of the orthopedic implant for use in a procedure, a surgeon may want the ability to adjust the orthopedic implant from a first position to a second position and/or have the orthopedic implant remain in place when the instrument is moved. As such, the implant holder may help prevent axial slipping of the orthopedic implant relative to the chuck during use without the presence of any additional external forces acting on the orthopedic implant. Specifically, when the orthopedic implant is disposed within a chuck, grippers of the implant holder may engage the orthopedic implant, allowing secure one-handed use of the instrument such that the orthopedic implant is retained in place absent an external force beyond a certain, predetermined magnitude being applied. In this regard, a force by the surgeon to move the orthopedic implant along or about the axis may be facilitated. However, absent application of such an external force (e.g., by the surgeon), the orthopedic implant may remain stationary.

Furthermore, while the instrument having a measurement system as described herein may provide advantages over placing an orthopedic implant in a bone without use of the measurement system, certain operations and/or user preference may result in the instrument being used in a traditional sense without the measurement system. In this regard, the present disclosure also describes chuck embodiments that may engage a traditional orthopedic implant such that the instrument may be operated without the assistance of the measurement system. These chuck embodiments may also include features that allow for management (e.g., retention) of the measurement system components when used in this traditional manner.

Utilization of the measurement system in conjunction with placement of the orthopedic implant may allow for the orthopedic implant to be located precisely relative to the bone of the patient. When placing an orthopedic implant, the exact placement of the distal portion of the implant may vary from procedure to procedure. For example, the placement of the orthopedic implant may vary based upon the bone into which the orthopedic implant placed, the nature of the procedure relative to the bone, the nature of the repair of the bone, the use of the orthopedic implant, or other relevant factors that may dictate the placement of the orthopedic implant. Accordingly, while the measurement system may provide for precise determination of the location of the orthopedic implant as it is advanced into the bone of the patient, it may be necessary to provide various modes of operation for selective placement of the orthopedic implant as desired for a given specific procedure on a given specific portion of anatomy. As such, embodiments of the instrument described herein may include a mode selection that allows the user to select a particular mode of operation for specific placement of the orthopedic implant. Specifically, various modes of operation including a bicortical, subchondral, endosteal, and multi-cortical modes will be described herein.

In turn, the sensors of the measurement system may be interrogated and analyzed to determine placement of the orthopedic implant. Various approaches to this analysis may be provided. For example, different analysis techniques may be used for different given ones of the placement modes. The analysis techniques may include coordinated or collective analysis of a displacement sensor signal and a force sensor signal. Other techniques may include analysis of a single given sensor output of the measurement system. For instance, a displacement sensor or accelerometer may be used singularly for analysis in connection with placement of the implant. In either instance, additional signals may be derived from the single sensor. For instance, a displacement, velocity, acceleration, and/or derivative signal may be derived from the single sensor employed. These values may be used individually or collectively to determine placement of the implant in the bone. Such placement determinations may also be used to assist in the determining a location of a tool (e.g., a drill, saw, grinder, or the like) relative to the structure of a bone.

Further still, specific embodiments of orthopedic implants are described herein that may be utilized to provide improved performance when introduced into the bone of the patient using an instrument having a measurement system as described herein. For instance, determination using the measurement system of the placement of very small diameter orthopedic implants and/or orthopedic implants that are advanced relatively slowly into the bone of the patient may be difficult to determine. In this regard, specific embodiment of an orthopedic implant that may be utilized to provide improved performance when utilized with the measurement system. Specifically, the orthopedic implant may include a tapered or conical distal end of the orthopedic implant that is relatively blunt. A relief portion may be provided proximal to the relatively blunt distal end of the orthopedic implant that may provide a relief to reduce heat near the distal end of the orthopedic implant and/or reduce tissue damage in the area proximal to the distal end of the orthopedic implant. Further still, a helical section may be provided proximally to the distal end of the orthopedic implant and/or the relief portion that may be utilized to engage a cortex of the bone to assist in advancement of the orthopedic implant relative to the bone.

Accordingly, a first aspect of the present invention comprises a surgical instrument for use in placement of orthopedic implants relative to a bone of a patient. The instrument includes an instrument body having a first cannulated passage extending continuously through the instrument body along a working axis of the instrument. The first cannulated passage is sized to receive and extend about at least a portion of an orthopedic implant within the cannulated passage. The instrument also includes a chuck engageable with the orthopedic implant to selectively engage the orthopedic implant to restrict axial movement of the orthopedic implant relative to the chuck along the working axis in the absence of an external force being applied to the chuck. The chuck includes a second cannulated passage axially aligned along the working axis. The instrument also includes a drive engaged with the chuck to impart rotational motion of the chuck about the working axis. The instrument also includes a measurement system having a displacement sensing arm moveable in a direction parallel to the working axis to measure advancement of the orthopedic implant driven by the instrument into the bone of the patient along the working axis.

A number of feature refinements and additional features are applicable to the first aspect. These feature refinements and additional features may be used individually or in any combination. As such, each of the following features that will be discussed may be, but are not required to be, used with any other feature or combination of features of the first aspect.

For example, in certain embodiments, the chuck may be normally biased into engagement with the orthopedic implant. The chuck may include a plurality of jaw members that are engaged by a cam surface biased into engagement with the plurality of jaw members to dispose the jaw members toward the working axis to engage the orthopedic implant.

In an embodiment, a linear motion of advancement of the chuck relative to the orthopedic implant urges the plurality of jaw members of the chuck into engagement with the orthopedic implant. In this embodiment, the cam surface may include an annular ramped surface that is biased into engagement with the plurality of jaw members. Each of the plurality of jaw members may be a roller member engaged with the annular ramped surface such that at least a portion of each of the roller members at least partially extends into the second cannulated passage to engage the orthopedic implant. The roller member may be disposed for pivotal movement about a pivotal axis that is orthogonal to and offset from the working axis, and wherein the pivotal axis is eccentric to the roller member. In turn, the linear motion of advancement of the chuck relative to the orthopedic implant causes rotation of the roller member about the pivotal axis such that the roller member is moved toward the working axis, and such movement of each of the plurality of roller members may create a clamping engagement of the orthopedic implant by the plurality of roller members upon the linear motion of advancement of the chuck relative to the orthopedic implant. In contrast, motion of the chuck opposite the linear motion of advancement may cause counter rotation of the roller member about the pivotal axis such that the roller member is moved away from the working axis, thus allowing the orthopedic implant to move relative to the roller member when the chuck is moved opposite the linear motion of advancement to allow for retraction of the chuck relative to the orthopedic implant.

In an alternate embodiment, a rotational motion of the chuck relative to the orthopedic implant may urge the plurality of jaw members of the chuck into engagement with the orthopedic implant. In this embodiment, the cam surface comprises a helical surface that engages the plurality of jaw members. Each of the plurality of jaw members comprise a spherical member engaged with the helical surface such that at least a portion of each of the spherical members at least partially extends into the second cannulated passage to engage the orthopedic implant. A twist of the helical surface may urge each of the spherical members toward the working axis when rotated in a direction corresponding with advancement of the orthopedic implant.

In these embodiments, the cam surface may be engaged with a control member to dispose the cam surface between a biased state, a locked-open state, and a locked-close state. When in the biased state, the cam surface may urge the plurality of jaw members into engagement with the orthopedic implant at least upon a motion of advancement of the chuck relative to the orthopedic implant. Additionally, when in the locked closed state, the cam surface may engage the orthopedic implant upon a motion of advancement or retraction. Further still, when in the locked open state, the cam surface may dispose the plurality of jaw members to allow movement of the orthopedic implant axially along the working axis relative to the chuck.

In certain contexts described herein, the orthopedic implant may be selected from the group consisting of a transcutaneous pin and a Kirschner wire. However, the disclosure presented herein may be applicable to any orthopedic implant and/or surgical tool that may be engaged with an instrument such as a drill, saw, grinder, or the like.

In an embodiment, the chuck may be operative to engage a plurality of indexing features at predefined axial increments along the orthopedic implant. The chuck may include at least one jaw member displaceable relative to the second cannulated passage to selectively engage and disengage at least one of the plurality of indexing features of the orthopedic implant. The chuck may include a first jaw member and a second jaw member arranged for opposing engagement of the orthopedic implant in a radial direction relative to the working axis. The first jaw member may be offset from the second jaw member relative to the working axis. Specifically, the first jaw member may be offset from the second jaw member relative to the working axis a distance less than a length of the engagement feature along the working axis.

In one application, the first jaw member may be pivotal relative to a first pivot axis and the second jaw member may be pivotal relative to a second pivot axis. The first pivot axis and the second pivot axis may be parallel to and offset from the working axis such that relative pivotal movement between the first jaw member and the second jaw member about the first pivot axis and the second pivot axis, respectively, results in the opposing radial movement of the first jaw member and the second jaw member relative to the working axis. In turn, the chuck may include a control ring disposed at an exterior surface of the chuck that is manipulable by a user to induce the relative pivotal movement of the first jaw member and the second jaw member. The control ring may include a first cam surface and a second cam surface. The first jaw member may include a first follower portion engaged with the first cam surface and the second jaw member may include a second follower portion engaged with the second cam surface. As such, upon rotation of the control ring by a user, the first cam surface and the second cam surfaces may bear on the first follower portion and the second follower portion to move the first jaw member and the second jaw member away from the working axis in a direction radial to the working axis. The first jaw member and the second jaw member may be biased into an engaged position where the first jaw member and the second jaw member may be biased in a direction radially toward the working axis.

In an embodiment, the chuck may also include at least one implant holder displaceable relative to the second cannulated passage to retain the orthopedic implant. The implant holder may include at least one gripper and a spring. The spring may bias the at least one gripper toward the working axis in a direction radial to the working axis. In turn, upon insertion of the orthopedic implant, the orthopedic implant may displace the gripper away from the working axis in a direction radial to the working axis and the implant holder bears on the orthopedic implant in a direction radially toward the working axis.

A second aspect presented herein includes a system for use with a surgical instrument for placement of orthopedic implants. The system includes an orthopedic implant having a plurality indexing features provided at predefined axial increments along the orthopedic implant and a chuck engageable with at least one of the plurality of indexing features to restrict axial movement of the orthopedic implant relative to the chuck along a working axis of the chuck.

A number of feature refinements and additional features are applicable to second aspect. These feature refinements and additional features may be used individually or in any combination. As such, each of the following features that will be discussed may be, but are not required to be, used with any other feature or combination of features of the second aspect. Furthermore, any of the features described in relation to the first aspect may be used with the second aspect.

In an embodiment of the second aspect, the orthopedic implant may include a cylindrical body extending from a proximal portion engageable with a bone of a patient to a distal portion opposite the proximal portion. The orthopedic implant may be selected from the group consisting of a transcutaneous pin and a Kirschner wire. The chuck may include at least one jaw member displaceable relative to the second cannulated passage to selectively engage and disengage at least one of the plurality of indexing features of the orthopedic implant. The plurality of indexing features may include indented portions of the cylindrical body extending radially toward a center axis of the cylindrical body. The indented portions may extend along opposing sides of the orthopedic implant.

In an embodiment, the indented portions may be offset a first distance along the working axis relative to the opposing sides. The chuck may include a first jaw member and a second jaw member arranged for opposing engagement of the orthopedic implant in a radial direction relative to the working axis. The first jaw member may be offset a second distance from the second jaw member relative to the working axis such that the second distance corresponds with the first distance. The first jaw member may be offset from the second jaw member relative to the working axis a distance less than a length of the engagement feature along the working axis. The first jaw member may be pivotal relative to a first pivot axis and the second jaw member may be pivotal relative to a second pivot axis. The first pivot axis and the second pivot axis may be parallel to and offset from the working axis such that relative pivotal movement between the first jaw member and the second jaw member about the first pivot axis and the second pivot axis, respectively, results in the opposing radial movement of the first jaw member and the second jaw member relative to the working axis.

The chuck may include a control ring disposed at an exterior surface of the chuck that is manipulable by a user to induce the relative pivotal movement of the first jaw member and the second jaw member. The control ring may include a first cam surface and a second cam surface. The first jaw member may include a first follower portion engaged with the first cam surface and the second jaw member may include a second follower portion engaged with the second cam surface. Upon rotation of the control ring by a user, the first cam surface and the second cam surfaces bear on the first follower portion and the second follower portion to move the first jaw member and the second jaw member away from the working axis in a direction radial to the working axis. The first jaw member and the second jaw member may be biased into an engaged position where the first jaw member and the second jaw member are biased in a direction radially toward the working axis.

A third aspect includes an orthopedic implant for use in conjunction with a measurement system of an instrument for advancing the orthopedic implant into a bone of a patient. The orthopedic implant includes a distal end comprising a working portion rotatably advanceable relative to the bone of the patient. The implant also includes a cylindrical body extending proximally from the distal end and a plurality of indexing features at predefined axial increments along the cylindrical body of the orthopedic implant that are engageable by a chuck of the instrument to restrict axial movement of the orthopedic implant relative to the chuck along a working axis of the chuck.

A number of feature refinements and additional features are applicable to the third aspect. These feature refinements and additional features may be used individually or in any combination. As such, each of the following features that will be discussed may be, but are not required to be, used with any other feature or combination of features of the third aspect.

For instance, the indexing features may include indented portions of the cylindrical body extending radially toward a center axis of the cylindrical body. The indented portions may extend along opposing sides of the orthopedic implant. The indented portions may be offset a first distance along the working axis relative to the opposing sides.

A fourth aspect includes a method of advancing an orthopedic implant into a bone of a patient. The method includes engaging the orthopedic implant with a chuck of an instrument to restrict axial movement of the orthopedic implant relative to the chuck along a working axis of the chuck. The method further includes first advancing the orthopedic implant distally into the bone of the patient a first distance by imparting rotational motion to the chuck when engaged with the orthopedic implant and first measuring the first distance using a displacement sensor of a measurement system associated with the instrument. The method also includes releasing the orthopedic implant from the chuck and retracting the instrument relative to the orthopedic implant in a proximal direction opposite of the direction of the advancing. The method includes reengaging the orthopedic implant with the chuck of the instrument to restrict axial movement of the orthopedic implant relative to the chuck along a working axis of the chuck and second advancing the orthopedic implant distally into the bone of the patient a second distance by imparting rotational motion to the chuck. The method includes second measuring the second distance using the displacement sensor of the measurement system associated with the instrument.

A number of feature refinements and additional features are applicable to the fourth aspect. These feature refinements and additional features may be used individually or in any combination. As such, each of the following features that will be discussed may be, but are not required to be, used with any other feature or combination of features of the fourth aspect.

For instance, in an embodiment, the method may include summing the first distance and the second distance at the measurement system. Furthermore, the method may include determining that the orthopedic implant is released from the chuck and disregarding any change in displacement of the displacement sensor when the orthopedic implant is released from the chuck. A sensor may be provided relative to the chuck to determine that the orthopedic implant is released from the chuck. The determining may alternatively be based on a user input provided to the measurement system. The engaging may include the chuck engaging the orthopedic implant at a first indexing feature of a plurality of indexing features and the reengaging comprises the chuck engaging the orthopedic implant at a second indexing feature of the plurality of indexing features that is proximal to the first indexing feature. The engaging may occur in response to the first advancing, the reengaging may occur in response to the second advancing, and the releasing may occur in response to the retracting.

A fifth aspect includes a method of placement of an orthopedic implant relative to a bone of a patient. The method includes engaging the orthopedic implant with a chuck of an instrument to restrict axial movement of the orthopedic implant relative to the chuck along a working axis of the chuck and advancing the orthopedic implant distally into the bone of the patient while the orthopedic implant is engaged with the chuck by imparting rotational motion to the chuck with a drive engaged with the chuck.

The method also includes measuring at least one characteristic of the advancement of the orthopedic implant relative to the bone. The method further includes continuously monitoring the at least one characteristic during the advancing to determine a predetermined placement of a distal end of the orthopedic implant and deactivating the drive to cease rotation of the chuck to stop the advancement of the orthopedic implant when the distal end of the orthopedic implant reaches the predetermined placement as determined by the continually monitored at least one characteristic. The predetermined placement is selectable by a user from a bicortical mode, a subchondral mode, an endosteal mode, and a multi-cortical mode.

A number of feature refinements and additional features are applicable to the fifth aspect. These feature refinements and additional features may be used individually or in any combination. As such, each of the following features that will be discussed may be, but are not required to be, used with any other feature or combination of features of the fifth aspect.

For instance, the at least one characteristic may include a force acting axially on the orthopedic implant and a depth of penetration of the orthopedic implant. Additionally or alternatively, the at least one characteristic may include a depth of penetration of the orthopedic implant as determined by a displacement sensor that generates a displacement signal. The displacement signal may also or alternatively be used to generate a velocity signal and an acceleration signal. In this regard, the predetermined placement may be determined based on the displacement signal, the velocity signal, and the acceleration signal. The displacement signal may be used to generate a derivative signal comprising a derivative of an acceleration signal generated using the displacement signal. The derivative signal is used to determine the predetermined placement. An inflection point of the derivative signal may correspond to an interface between a first medium having a first density and a second medium having a second density. Specifically, a concave up inflection point is indicative of the orthopedic implant passing through the interface where the first density is less than the second density. In contrast, a concave down inflection point is indicative of the orthopedic implant passing through the interface where the first density is greater than the second density.

A sixth aspect includes an orthopedic implant. The implant includes a cylindrical body extending between a distal end and a proximal end. The implant also includes a tapered portion adjacent to the distal end that is advanceable relative to a bone of the patient. The implant further includes a relief portion proximal to the distal end extending about the cylindrical body and a helical portion proximal to the relief portion.

A number of feature refinements and additional features are applicable to the sixth aspect. These feature refinements and additional features may be used individually or in any combination. As such, each of the following features that will be discussed may be, but are not required to be, used with any other feature or combination of features of the sixth aspect.

For instance, in an embodiment, the helical portion may include threads to engage a cortex of a bone. The relief portion may include a circumferentially extending step having a first radius that is smaller than a second radius of the cylindrical body.

BRIEF DESCRIPTION OF THE DRAWINGS

FIG. 20 depicts an embodiment of an orthopedic implant having indexing features.

FIGS. 36A and 36B depict an embodiment of a controller for use with an instrument.

DETAILED DESCRIPTION

The following description is not intended to limit the invention to the forms disclosed herein. Consequently, variations and modifications commensurate with the following teachings, skill and knowledge of the relevant art, are within the scope of the present invention. The embodiments described herein are further intended to explain modes known of practicing the invention and to enable others skilled in the art to utilize the invention in such, or other embodiments and with various modifications required by the particular applications(s) or use(s) of the present invention.

Figure 1:
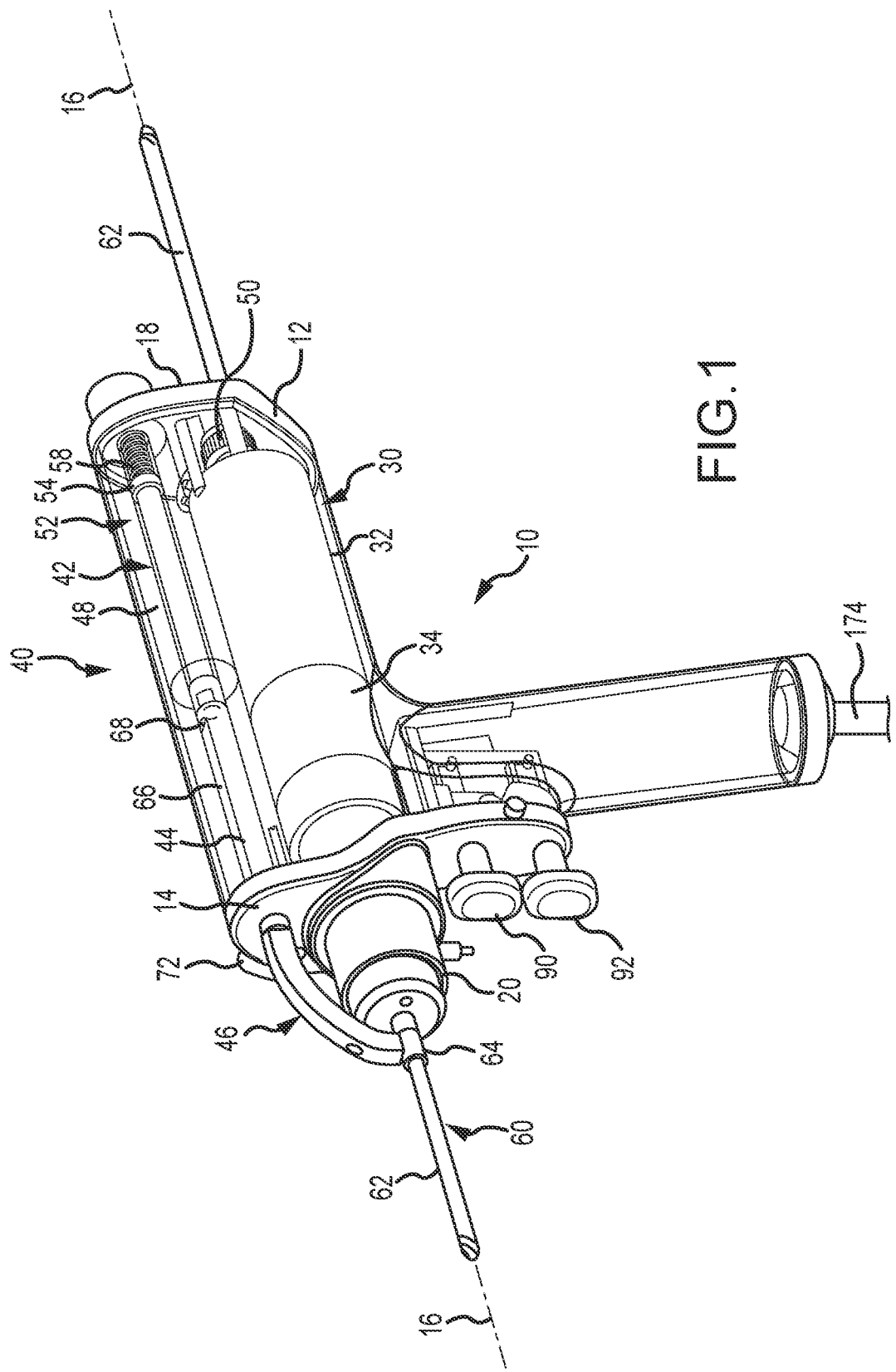
FIG. 1 depicts an embodiment of an instrument that may be used in connection with placement of an orthopedic implant.
Figure 2:
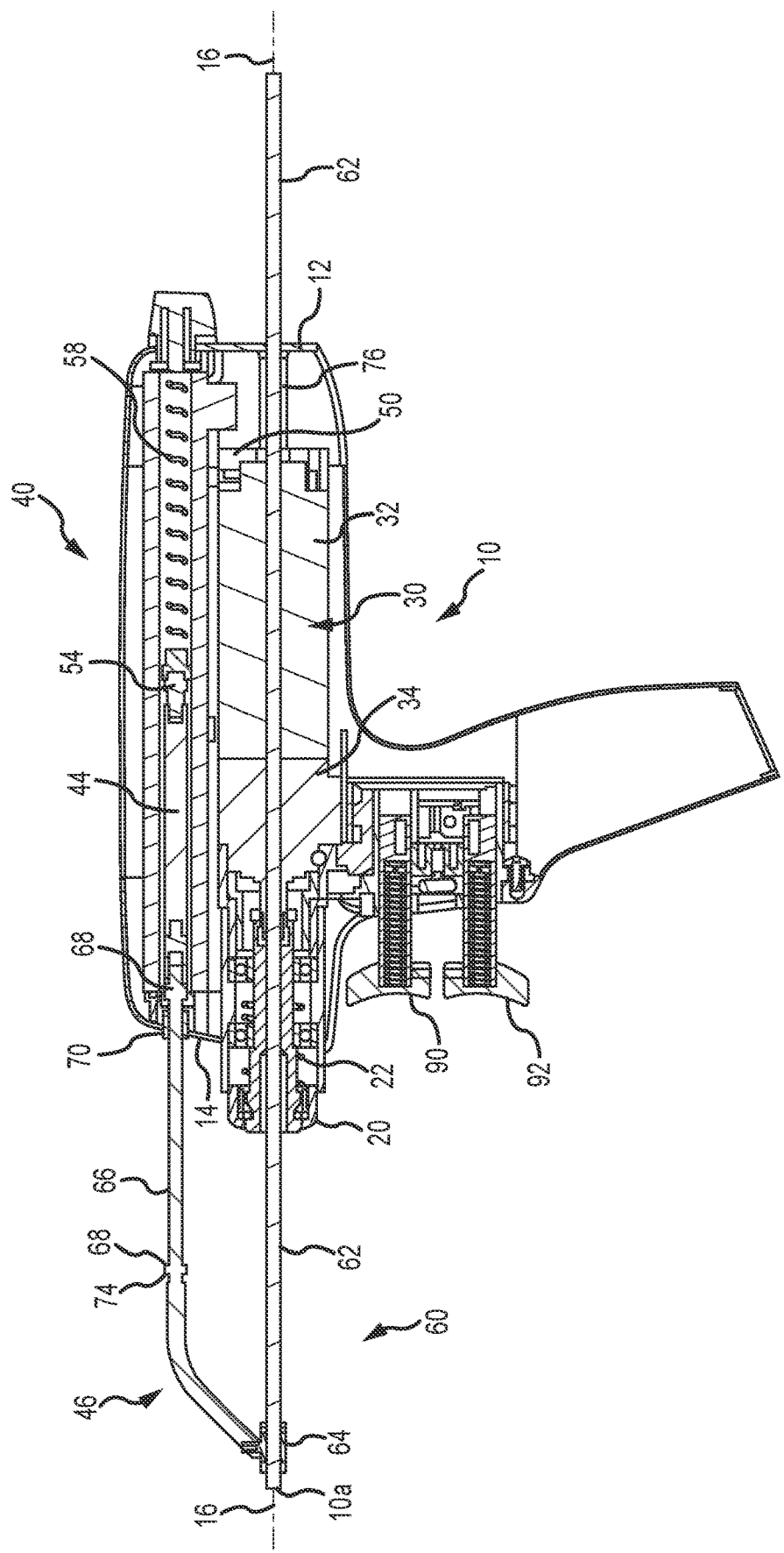
FIG. 2 depicts a cross sectional view of an embodiment of an instrument with an orthopedic implant engaged therewith.
Figure 3:
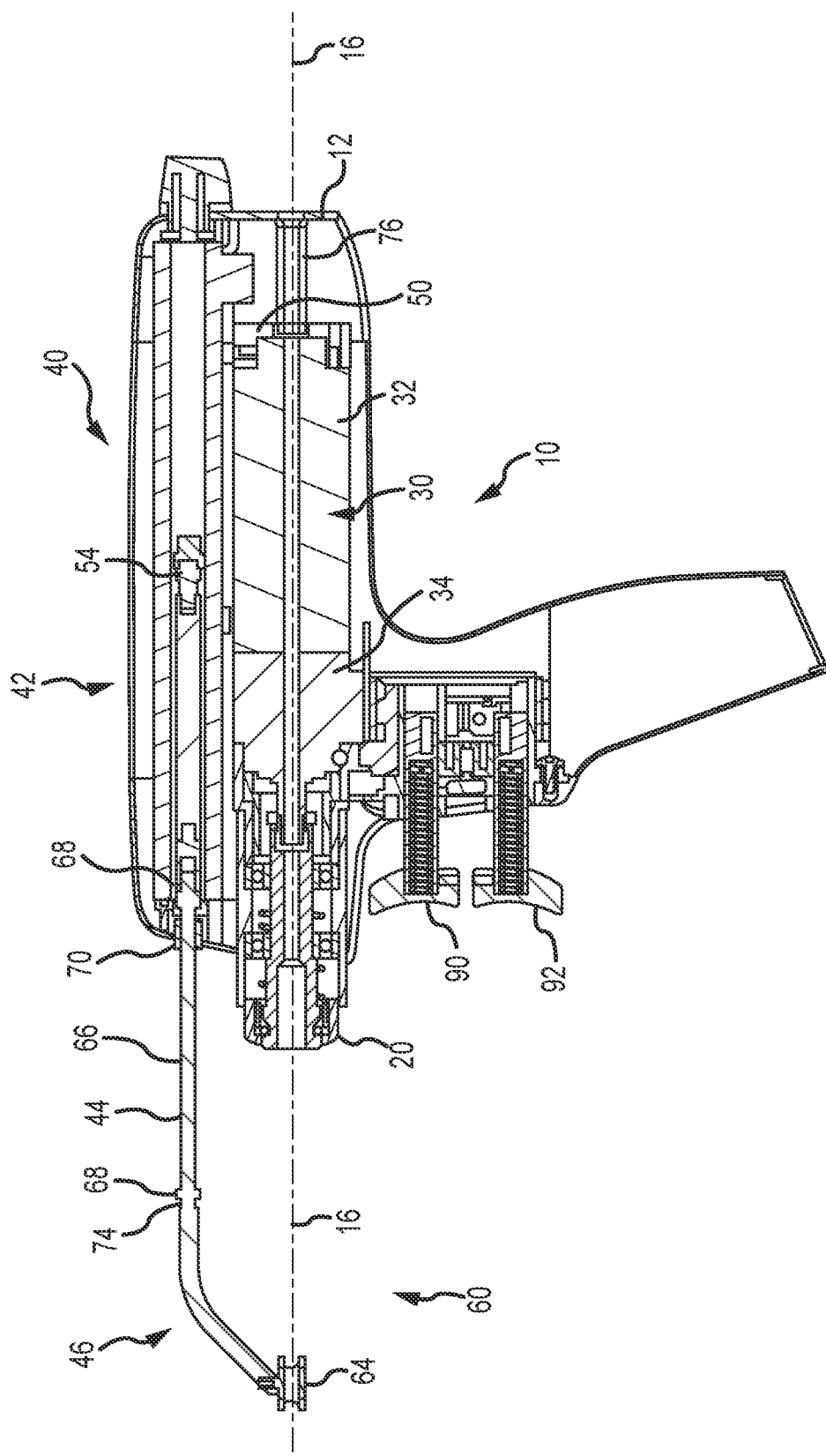
FIG. 3 depicts a cross sectional view of an embodiment of an instrument that may be used with an orthopedic implant.

As described above, the present disclosure includes disclosure that relates to the use of an instrument having a measurement system for placement of an orthopedic implant into the anatomy (e.g., the bone) of a patient. For instance, the orthopedic implant may include a pin or wire that is placed in the bone of the patient using a powered instrument such as a drill or the like. FIGS. 1-3 depict an embodiment of an instrument 10 that may be utilized for such placement of an orthopedic implant 62.

The use of orthopedic implants such as pins (e.g., IM pins) and/or wires (e.g., K-wires) may be used in a variety of orthopedic applications. The orthopedic implants may be used to provide traction to the bones of a patient. Moreover, the orthopedic implant may be placed to allow for induced motion of a bone (e.g., to provide alignment, rotation, or other manipulation of a bone). Furthermore, orthopedic implants may be used for fixation to secure fractured bone portions. In any regard, for the various contexts of uses for the orthopedic implants, different relative placements may be desired. Such placement may be aided by use of a measurement system that may assist in determining placement of the orthopedic implant as described in detail below.

As will be described in greater detail below, use of an instrument having a measurement system may provide a number of benefits in relation to placement of an orthopedic implant. For instance, because the measurement system may have the capability of automatically detecting when an implant passes through an interface of the bone, the user of the instrument may not be required to determine implant placement by "feel" alone. In turn, the time required to place an implant may be reduced. Moreover, the repeatability of implant placement may be increased. Moreover, embodiments are described herein wherein a user may not be required to impart an external force onto a chuck to maintain engagement with an orthopedic implant. In turn, the user may be more able to control the instrument as a more ergonomic grip with greater control of the instrument may be taken by the user. Further still, by not requiring an external force be applied to the chuck for engagement of the instrument, the measurement system may provide increased accuracy both based on a reduced potential that the orthopedic implant slips relative to the instrument and/or based on a more accurate force signal that may not be subject to noise in the form of erroneous forces resulting from engagement with the chuck by the user.

Further still, when utilizing a measurement system for placement of an orthopedic implant, it may be advantageous to periodically disengage the orthopedic implant from the instrument so as to allow the instrument to be moved relative to the orthopedic implant. For example, the orthopedic implant may be advanced a certain distance into the bone of the patient. The advancement of the orthopedic implant may be greater than the distance that is measurable by a single stroke of the displacement sensing arm of the measurement system. As such, the instrument may be disengaged and moved distally relative to the orthopedic implant. The instrument may thereafter reengage the orthopedic implant for continued advancement of the orthopedic implant. In this regard, it may be advantageous to provide efficient engagement and disengagement of the orthopedic implant without requiring external force be applied by the user and while maintaining the orthopedic implant stationary along the working axis. Accordingly, at least some of the embodiments described herein may allow for efficient retraction of the instrument relative to the implant. Such retraction may include disengagement of the chuck from the implant in an ergonomic and efficient manner. Still other embodiments allow for engagement of the implant upon advancement thereof, while allowing for disengagement (e.g., automatically) when the instrument in retracted relative to the implant.

The instrument 10 may include a chuck 20 for engagement of an orthopedic implant 62. The orthopedic implant 62 may comprise a portion of an orthopedic implant assembly 60 that may be specifically adapted for utilization with the measurement system 40 of the instrument 10. For instance, the assembly 60 may include the implant 62 and a correspondingly sized bushing 64 as will be described in greater detail below.

A drive system 30 may be provided that may include a motor 32 and a gearbox 34. In turn, the drive system 30 may engage the chuck 20 to impart rotational motion to the chuck 20 about a working axis 16. That is, the working axis 16 may define an axis of rotation about which the drive system 30 may induce rotation of the chuck 20 and, when engaged therewith, an orthopedic implant 62. In this regard, the orthopedic implant 62 may be advanced into a bone along the working axis 16. Notably, the chuck 20 and drive system 30 maybe cannulated to accept the orthopedic implant 62. Furthermore, the drill housing 12 may also be cannulated such that the orthopedic implant 62 may pass entirely through the body the instrument 10 including the chuck 20, drive system 30, and housing 12. In this regard, the instrument 10 may include a cannulated passage 76 may extend from the proximal portion of the instrument 10 to a distal portion thereof. This cannulated passage may be defined, at least in part, by the chuck 20, the drive system 30, and the housing 12. As such, the chuck 20 may also include a cannulated passage 22. In this regard and as will be described in greater detail below, the cannulated passage 22 of the chuck 20 may be selectively aligned to the cannulated passage 76 of the instrument 10 in embodiments where the chuck 20 selectively removable from the instrument 10 for interchanging of the chuck utilized with the instrument 10.

With continued reference to FIGS. 1-3, an embodiment of a measurement system 40 is shown. The instrument 10 may be adapted for use with an orthopedic implant assembly 60 that may include a bushing 64. The bushing 64 may be correspondingly sized to extend about at least a portion of the orthopedic implant 62 to allow for constrained axial movement of the bushing 64 relative to the orthopedic implant 62. Alternatively, the bushing 64 may be integrally provided with the measurement system 40 as described in greater detail below. The instrument 10 may comprise at least some components of the measurement system 40 within the housing 12 to facilitate operation of the measurement system 40 in connection with the instrument 10. For example, at least a portion of a displacement sensor 42 may be integrated into a housing 12 of the instrument 10. In this regard, the displacement sensor 42 may include a depth sensing arm 44 that is specifically adapted for engagement with the bushing 64 of the orthopedic implant assembly 60 that may be engaged by a chuck 20 of the instrument 10. While the bushing 64 is shown as a discrete part, the bushing 64 may also be provided integrally with the displacement sensing arm 44.

The measurement system 40 may also include a force sensor 50. The force sensor 50 may be disposed relative to the drive system 30. The chuck 20 and drive system 30 may undergo relative movement to the force sensor 50. However, the chuck 20 and drive system 30 may be axially rigid such that an axial force acting on the chuck 20 (e.g., as imparted to the implant 62 upon axial advancement of the orthopedic implant 62 engaged with the chuck 20) may be passed to the chuck 20 and drive system 30 such that the drive system 30 may impinge on the force sensor 50 such that the force sensor 50 may measure the force. Thus, the chuck 20 and drive system 30 may be supported such that the axial movement of the chuck 20 and drive system 30 is limited (e.g., to prevent error in relation to the displacement sensor 42), yet allow for the free transfer of force to the force sensor 50. That is, it is advantageous to reduce the action of errant forces on the chuck 20 and drive system 30 along the working axis 16 to improve the accuracy of the measured force at the force sensor 50. For instance, upon contact of the drive system 30 with the force sensor 50, further axial forces on the drive system 30 may result in minimal deflection (i.e., imperceptibly by the displacement sensor 40) while impinging on the force sensor 50. In this regard, the drive system 30 may be constrained for contacting engagement with the force sensor 50, but otherwise free to deflect along the working axis to achieve an accurate force measurement. As will be appreciated in greater detail below, utilization of an indexed orthopedic implant 62 that is engaged by the chuck 20 may allow for maintaining the orthopedic implant 62 stationary relative to the chuck 20 along the working axis 16 while allowing forces acting on the orthopedic implant 62 to be transmitted in the direction along the working axis 16 such that the force sensor 50 may accurately measure the force imparted onto the orthopedic implant 62 as it is advanced relative to the bone of the patient.

Returning to the description of the displacement sensor 42, the depth sensing arm 44 may be used to establish a reference point from which displacement of an orthopedic implant 62 may be measured. In this regard, as follows herein, a general description of the features and operation of the instrument 10 used in conjunction with the orthopedic implant assembly 60 is provided.

The depth sensing arm 44 may extend from the drill housing 12. For example, the depth sensing arm 44 may extend distally (e.g., from a distal face 14 of the drill housing 12) in a direction corresponding with the direction in which the orthopedic implant 62 extends from the chuck 20 of the instrument 10 for advancement into a bone. At least a portion of the displacement sensing arm 44 may extend from the drill housing 12 parallel to the working axis 16 of the instrument 10. The depth sensing arm 44 may also include a distal portion 46 that is adapted to engage the bushing 64 provided with the orthopedic implant assembly 60. Alternatively, the distal portion 46 may include an integrally provided bushing 64 as described above. As used herein, distal may correspond to a direction toward the leading edge 10a of the orthopedic implant 62 and proximal may correspond to a direction away from the leading edge 10a of the orthopedic implant 62 toward an opposite end of the orthopedic implant 62. In this regard, at least a portion of the depth sensing arm 44 (e.g., the distal portion 46) may be adapted to engage the bushing 64 of the orthopedic implant assembly 60. In any regard, at least a portion of the depth sensing arm 44 may extend into the housing 12.

In an embodiment, the displacement sensor 40 may comprise a linear variable differential transformer (LVDT) sensor that is adapted to sense the position of a core 54 relative to a coil 48. Accordingly, the housing 12 may contain a coil 48. A proximal end 52 of the displacement sensing arm 44 may include the core 54 that may interact with the coil 48 of the displacement sensor 40. Specifically, as shown in FIG. 1, the depth sensing arm 44 is in a retracted position relative to the orthopedic implant 62. For example, this retracted position shown in FIG. 1 may occur when the orthopedic implant 62 is advanced during placement of the orthopedic implant 62 in the bone of a patient (e.g., such that the portion of the orthopedic implant 62 extending beyond the distal edge of the bushing 64 would be disposed in the bone of the patient). In this regard, the proximal end 52 of the displacement sensing arm 44 may be disposed within the coil 48 of the displacement sensor 40. Accordingly, as the proximal end 52 of the displacement sensing arm 44 is moved relative to the coil 48, the location of the core 54 may be determined relative to the coil 48 (e.g., by monitoring the induced current of the coil 48) to provide an output that is indicative of the position of the core 54, and in turn the position of the displacement sensing arm 44 relative to the drill housing 12. That is, the depth sensing arm 44 may be displaceable relative to the coil 48 such that the displacement sensor 42 may be operable to sense a change in position of the depth sensing arm 44 and output a measure of the displacement that may be used in determining a depth of penetration of the orthopedic implant 62 relative to a bone in which the implant 62 is inserted. In an embodiment, the total measurable travel of the core 54 relative to the coil 48 may be at least about 2.5 in (6.4 cm). Furthermore, the resolution of the output of the displacement sensor 42 may be about 0.1% (e.g., about 0.002 inches (0.06 mm) for a sensor having a total measureable travel of 2.5 inches (6.4 cm)).

While a LVDT displacement sensor is shown and described in relation to the instrument 10 shown in the accompanying figures, it may be appreciated that other types of displacement sensors may be provided. For instance, the sensor may provide for the absolute or relative measurement of the position of the distal end 46 of the displacement sensing arm 44 to provide a displacement measure. For instance, in another embodiment, an optical displacement sensor may be provided. Other types of displacement sensors are also contemplated such as, for example, a capacitive displacement sensor, ultrasonic sensors, Hall effect sensors, or any other sensors known in the art capable of outputting an absolute or relative position measure. In any regard, the use of the bushing 64 that is engaged with the displacement sensing arm 44 may allow for a reference point to be established using the bushing 64 resting external to the substrate into which the orthopedic implant 62 is advanced. For instance, a controller (described in greater detail below) may receive an input to reset or "zero" the measure of the displacement sensor 42 when the bushing and leading edge 10a of the implant 62 are in contact with an exterior surface of the bone into which the implant 62 is to be advanced. Accordingly, any relative movement of the orthopedic implant 62 relative to the bushing 64 may be measured to determine the depth of penetration of the leading edge 10a of the orthopedic implant 62 as it is advanced into a substrate (e.g., a patient's bone).

A biasing member 58 (e.g., a coil spring) may be provided relative to the proximal end 52 of the displacement sensing arm 44. In this regard, the biasing member 58 may act on the proximal end 52 of the displacement sensing arm 44 to bias the displacement sensing arm 44 distally. This may assist in maintaining the bushing 64 in contact with the bone to increase the accuracy of the displacement sensor 42.

In an embodiment, the displacement sensing arm 44 may include features that selectively prevent ejection of the displacement sensing arm 44 from the instrument in the distal direction when the displacement sensing arm 44 is distally biased. For example, the displacement sensing arm 44 may include at least one flat portion 66 that extends along a portion of the displacement sensing arm 44. At the proximal and distal extents of the flat 66, the displacement sensing arm 44 may include shoulders 68 that project from the flat 66. As such, a selectively displaceable stop 70 (best seen in FIGS. 2 and 3) may be disposed relative to the flat portion 66 such that the flat portion 66 may move distally and proximally relative to the stop 70. However, the stop 70 may interfere with the shoulder 68 defined in the displacement sensing arm 44 to prevent passage of the shoulders 68 beyond the stop 70. That is, a distal shoulder 68 may limit proximal movement of the displacement sensing arm 44 beyond the stop and a proximal shoulder 68 may limit distal movement of the displacement sensing arm 44 beyond the stop 70. In this regard, the length of the displacement sensing arm 44 along which the flat portion 66 extends may be moveable relative to the stop 70 between the distal and proximal shoulders 68 defined at the ends of the flat portion 66.

However, the stop 70 may be displaceable by, for example, depressing a button 72 provided on an exterior of the housing 12. Thus, upon depressing the button 72, the stop 70 may be displaced away from the displacement sensing arm 44 to allow the shoulder 68 to pass by the stop 70 such that the displacement sensing arm 44 may be removed from the instrument 10. Additionally, the distal end of the flat 66 may include a detent 74 that may be engageable with the stop 70 so as to maintain the displacement sensing arm 44 in a proximally disposed, retracted position relative to the housing 12 such as that shown in FIG. 1. Once the button 70 is depressed and released, the detent 74 at the proximal end of the flat portion 66 may be released by the stop 70 and the displacement sensing arm 44 may move proximally (e.g., under influence of the biasing member 58). The displacement sensing arm 44 may move proximally until the shoulder 68 at the distal end of the flat 66 are engaged to prevent further distal movement of the displacement sensing arm 44. Accordingly, the displacement sensing arm 44 may be retained in a retracted position (e.g., for improved visibility of the distal end of the orthopedic implant 62 or to stow the displacement sensing arm 44 when not in use). However, the displacement sensing arm 44 may be released to be moveable relative to the housing 12. Moreover, the displacement sensing arm 44 may be removable altogether from the housing 12.

In the latter regard, removal of the displacement sensing arm 44 and biasing member 58 from the instrument 10 may allow for separate cleaning (e.g., in an autoclave) of those members. Additionally, removal of the displacement sensing arm 44 may allow for a cleaning apparatus (e.g., a brush or the like) to be passed through the instrument 10 to facilitate cleaning thereof.

As referenced above, in an embodiment the distal portion 46 of the displacement sensing arm 44 may be adapted to engage the orthopedic implant assembly 60 (e.g., a bushing 64 thereof) that is correspondingly adapted for use with the instrument 10. In this regard, the orthopedic implant assembly 60 may include the implant 62 and the bushing 64. The bushing 64 may be adapted for movement along the implant 62 relative to the working axis of the implant 62. The displacement sensing arm 44 may engage the bushing 64 such that movement of the bushing 64 relative to the implant 62 may also cause relative movement of the displacement sensing arm 44 relative to the implant 62. The displacement sensing arm 44 may generally be linear along a proximal portion 52 of the displacement sensing arm 44. In this regard, the proximal portion 52 may be adapted to be parallel with the cannulated passage 76 that extends along the working axis 16.

Furthermore, the distal portion 46 of the displacement sensing arm 44 (e.g., the portion distal to the linear portion of the displacement sensing arm 44) may extend from the linear portion of the displacement sensing arm 44 toward the orthopedic implant assembly 60 that may be engaged by the chuck 20 of the instrument 10. In this regard, the linear portion of the displacement sensing arm 44 may be substantially parallel to and offset from the working axis 16. The distal portion 46 may extend from the linear portion in a direction corresponding with the offset such that the distal portion 46 extends toward the orthopedic implant assembly 60. This may facilitate engagement between the displacement sensing arm 44 and the bushing 64 of the orthopedic implant assembly 60 (e.g., using a post and hole as described in U.S. Pat. No. 9,370,372, which is incorporated by reference herein in its entirety).

The distal portion 46 may be an at least partially arcuate member extending along a radius of curvature toward the orthopedic implant assembly 60. However, the distal portion 46 may be shaped differently (e.g., the distal portion 46 may be a linear portion extending at an angle or perpendicularly from the proximal portion 52 toward the orthopedic implant assembly 60). The configuration and operation of the measurement system 40 of the instrument 10 may be as described in any of the embodiments in U.S. Pat. Nos. 6,665,948, 9,370,372, or U.S. Patent Pub. No. 2016/0128704, all of which are incorporate by reference herein in their entireties. Moreover, operation of the bushing 64 in relation to the displacement sensing arm 44 may be according to any of the foregoing documents incorporated by reference. In this regard, the bushing 64 may interact with the orthopedic implant 62 in a manner similar to that described in relation to the bushing interacting with the drill bit or other instrument working portion described in the foregoing documents incorporate by reference.

Figure 4:
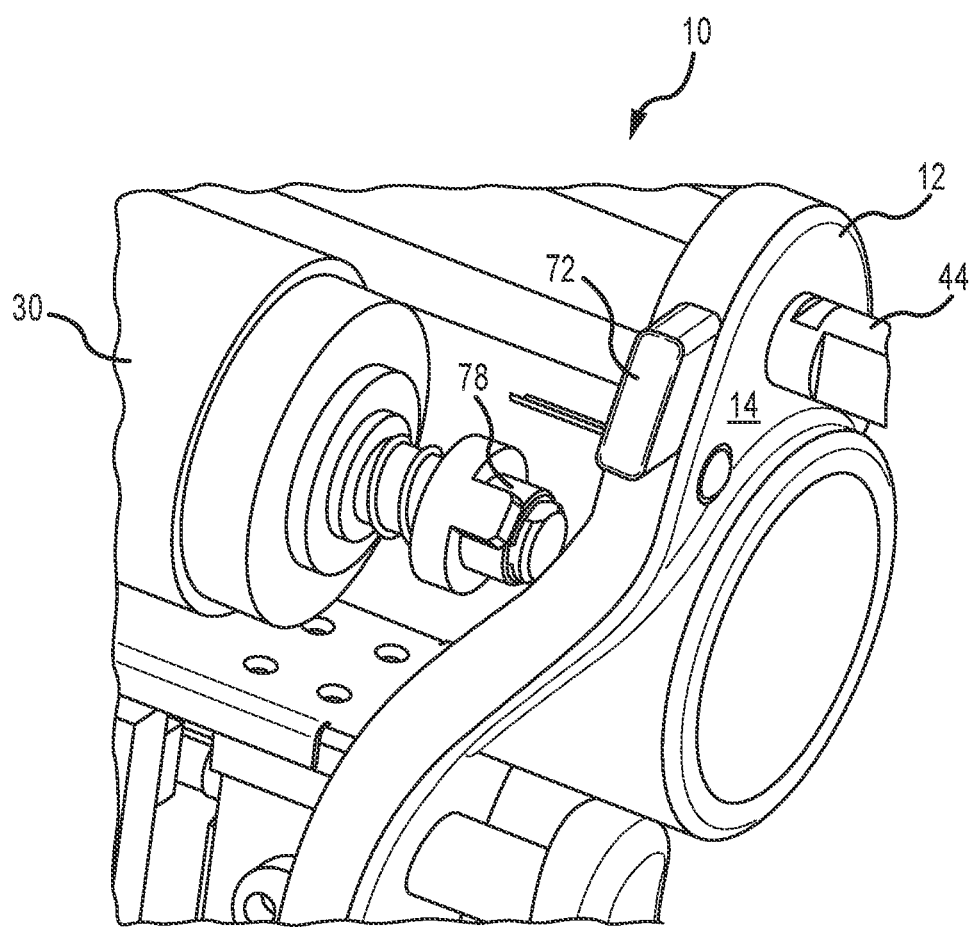
FIG. 4 depicts a partial cutaway view of an embodiment of a distal portion of an instrument for engagement with an interchangeable chuck.

As described briefly above, the chuck 20 may be selectively engageable and disengageable with the instrument 10. In this regard, various different chucks may be selectively utilized in conjunction with the instrument 10. To facilitate the different chucks, the instrument 10 may provide a standardized chuck engagement format to engage the various different potential embodiments of chucks 20 that may be utilized with the instrument 10. In this regard, as may be appreciated in FIG. 4, the instrument 10 may include a corresponding chuck drive coupling 78 that engages with a chuck 20 to impart rotational motion from the drive system 30 to the chuck 20. In this regard, the chuck 20 may be detachable from the drill 50. The chuck drive coupling 78 may be in operative communication with the drive system 30 such that the drive system 30 rotates the drive coupling 78. In turn, the chuck drive coupling 78 may engage with the chuck 20 to rotate at least a portion thereof. Furthermore, any chuck 20 configured for engagement with the instrument 10 may include a cannulated passage 22 that is alignable with the cannulated passage 76 of the instrument when the chuck 20 is engaged therewith.

Figure 5:
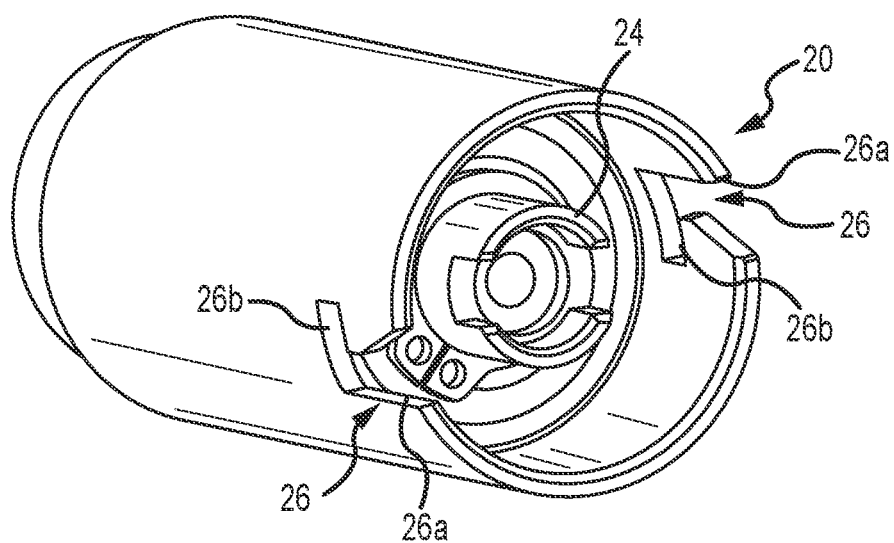
FIG. 5 depicts an embodiment of a chuck for engagement with an instrument.
Figure 6:
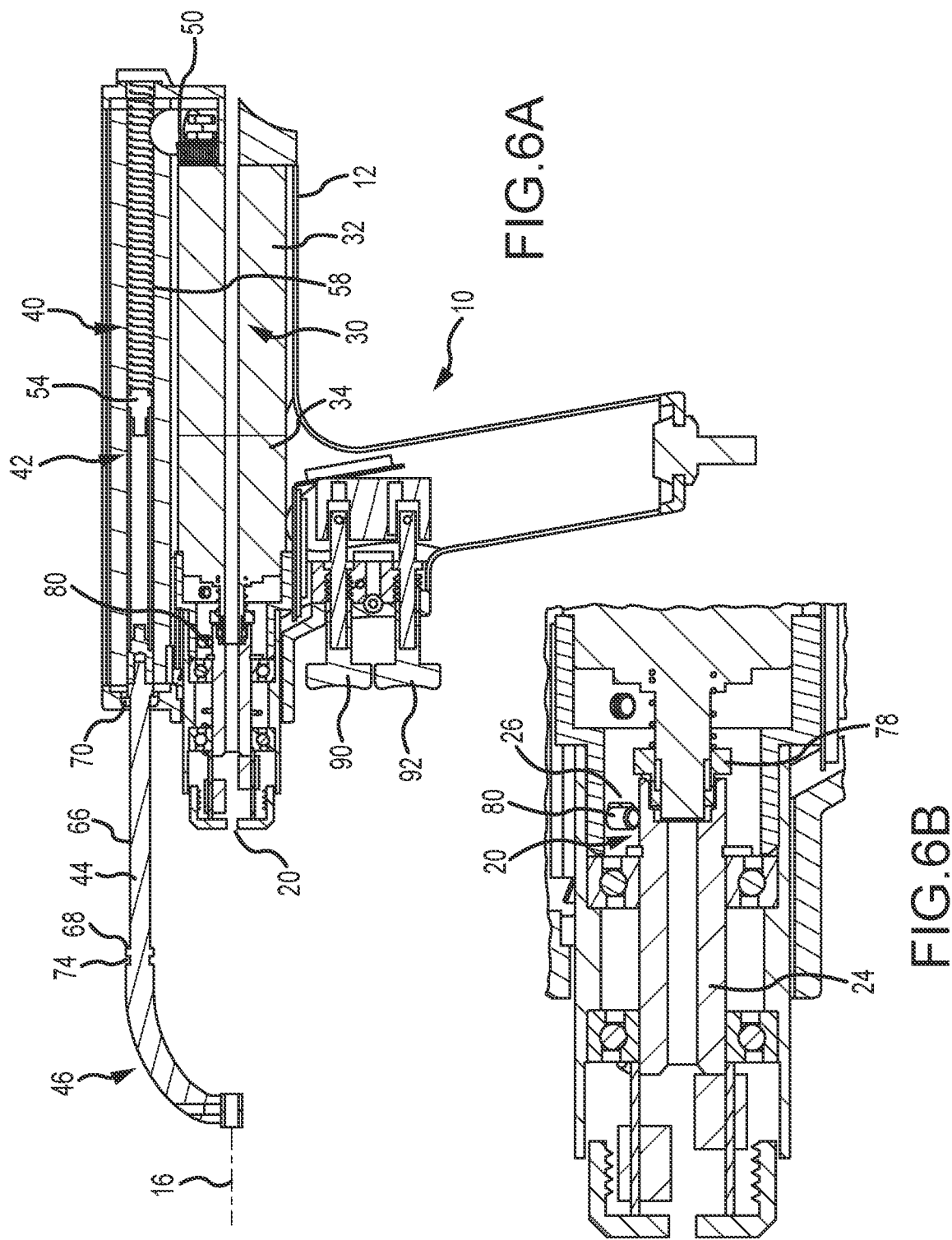
FIG. 6A depicts a cross sectional view of an embodiment of an instrument and interchangeable chuck as assembled.
FIG. 6B depicts a detail view of the embodiment depicted in FIG. 6A at an interface of the chuck with the instrument.

With further reference to FIG. 5, the proximal end of the chuck 20 may include a chuck drive shaft 24 disposed relative to slots 26. The slots 26 may coordinate with corresponding tabs 80 provided with the instrument 10 adjacent to the chuck drive coupling 78 (best seen in FIG. 6B) to retain the chuck 20 relative to the instrument 10. In turn, the chuck drive shaft 24 may be keyed or otherwise configured such that the chuck shaft 24 engages the chuck drive coupling 78 of the instrument 10. In turn, the chuck drive coupling 78 may impart rotational motion to the chuck drive shaft 24 to rotate an orthopedic implant 62 engaged with the chuck 20. The slots 26 may coordinate with the tabs 80 so as to allow the chuck 20 to be quickly attached and/or released from the instrument 10 by engagement of the slots 26 with the tabs 80. This may be appreciated from FIG. 5, where it is illustrated that the slots 26 may include a first portion 26a that extends parallel to the working axis 16.

The chuck may be advanced toward the chuck drive coupling 78 along the working axis 16 such that the tabs 80 travel along the first portion 26a to the distal end thereof. The slots 26 may also include a second portion 26b that extend circumferentially about the chuck 20. As such, once the tabs 80 abut the distal end of the first portion 26a, rotation of the chuck 20 may move the second portion 26b such that the tabs 80 extend into the second portion 26b, thus restricting the chuck 20 from movement relative to the working axis 16. That is, when the tabs 80 are disposed in the second portion 26b, the second portion 26b may be sized as to engage the tabs 80 to limit axial movement of the chuck 20 relative to the working axis 16 (e.g., to allow the chuck 20 to travel relative to the force sensor 50 for transferring force thereto, but to disallow the chuck 20 from moving distally from the instrument 10). Further locking mechanisms may be provided to prevent the chuck 20 from rotating relative to the working axis 16 when engaged so that the tabs 80 do not slip from the second portion 26b. For example, a release may be provided to lockingly maintain the chuck 20 in position to the instrument 10 such that the chuck 20 is only released for removal upon actuation of the release. Thus, the chuck 20 may be quickly and efficiently attached and detached from the instrument 10.

With further reference to FIGS. 6A and 6B, cross sectional views of the instrument 10 with orthopedic implant assembly 60 engaged therewith are shown. As may be appreciated, the chuck shaft 24 may engage the chuck drive coupling 78. As may also be appreciated, the chuck 20 may be operatively engaged with the instrument 10 such that the slots 26 of the chuck 20 are engaged with the tabs 80 to maintain the chuck 20 in engagement with the drive system 30. As will be appreciated in the following discussion, any or all of the chuck embodiments described below may have a similar engagement structure for selective engagement with the instrument 10. In this regard, any of the following embodiments of chucks may be interchangeably engaged with the instrument 10 for utilization with the instrument in a manner described below.

Figure 7:
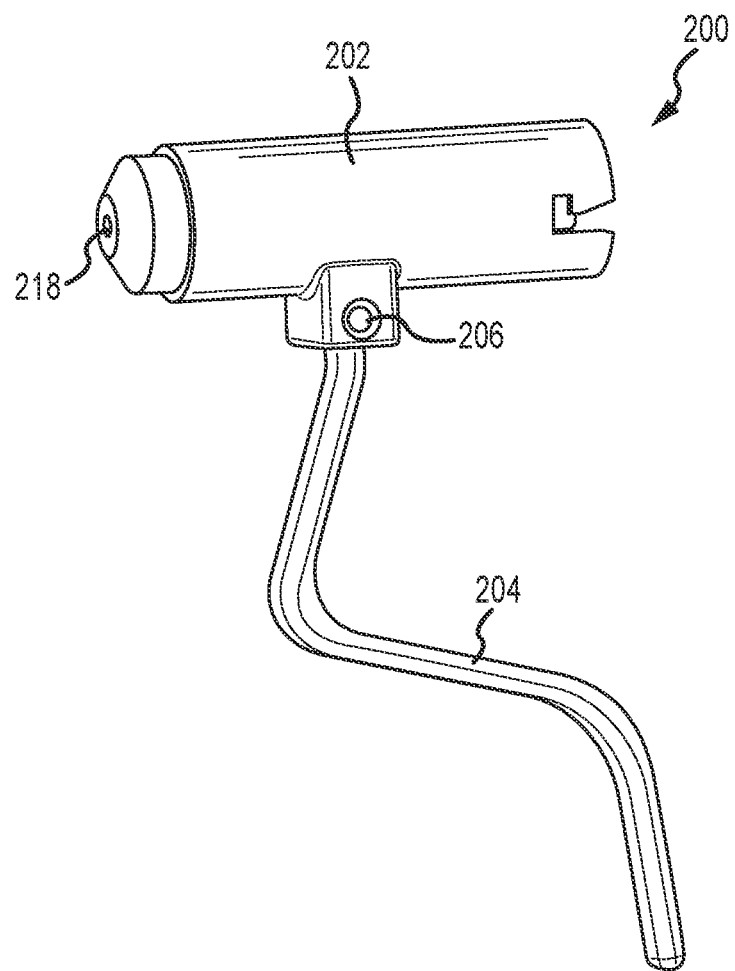
FIG. 7 depicts an embodiment of a chuck that may be used to retain an orthopedic implant.

For instance, FIG. 7 depicts an embodiment of a chuck 200. The chuck 200 may be utilized to engage a smooth-walled orthopedic implant such as a K-wire, IM pin, or other orthopedic implant to be placed utilizing the instrument 10. The chuck 200 generally includes a chuck body 202 that may include a proximal portion having engagement features such as slots 26 described above for attachment to the instrument 10. The chuck 200 may include an actuation lever 204 extending from the chuck body 202. During operation, a user may grasp the actuation lever 204 to engage the orthopedic implant with the chuck 200. In this regard, the actuation lever 204 may be contoured so as to dispose a free end of the actuation lever 204 adjacent to a handle of the instrument 10 such that the user may easily grasp the actuation lever 204 when holding the instrument 10. However, a user may be required to maintain a force or the activation lever 204 to engage an orthopedic implant 62 with the chuck 200.

Figure 8:
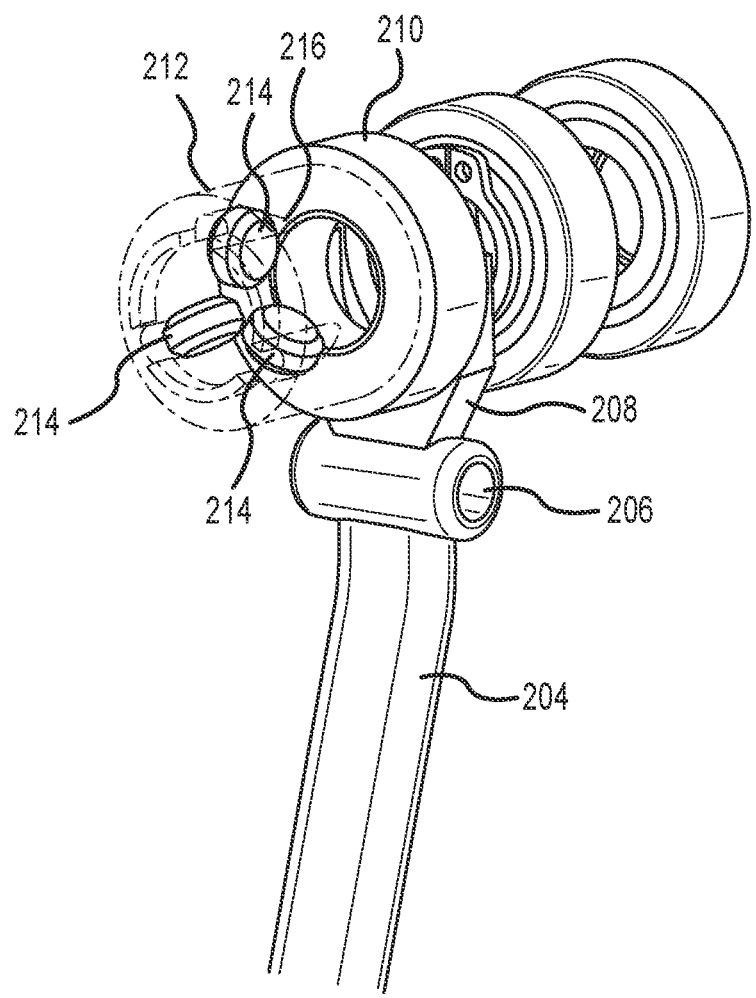
FIG. 8 depicts the embodiment of the chuck of FIG. 7 with an exterior portion thereof not shown for clarity.
Figure 9:
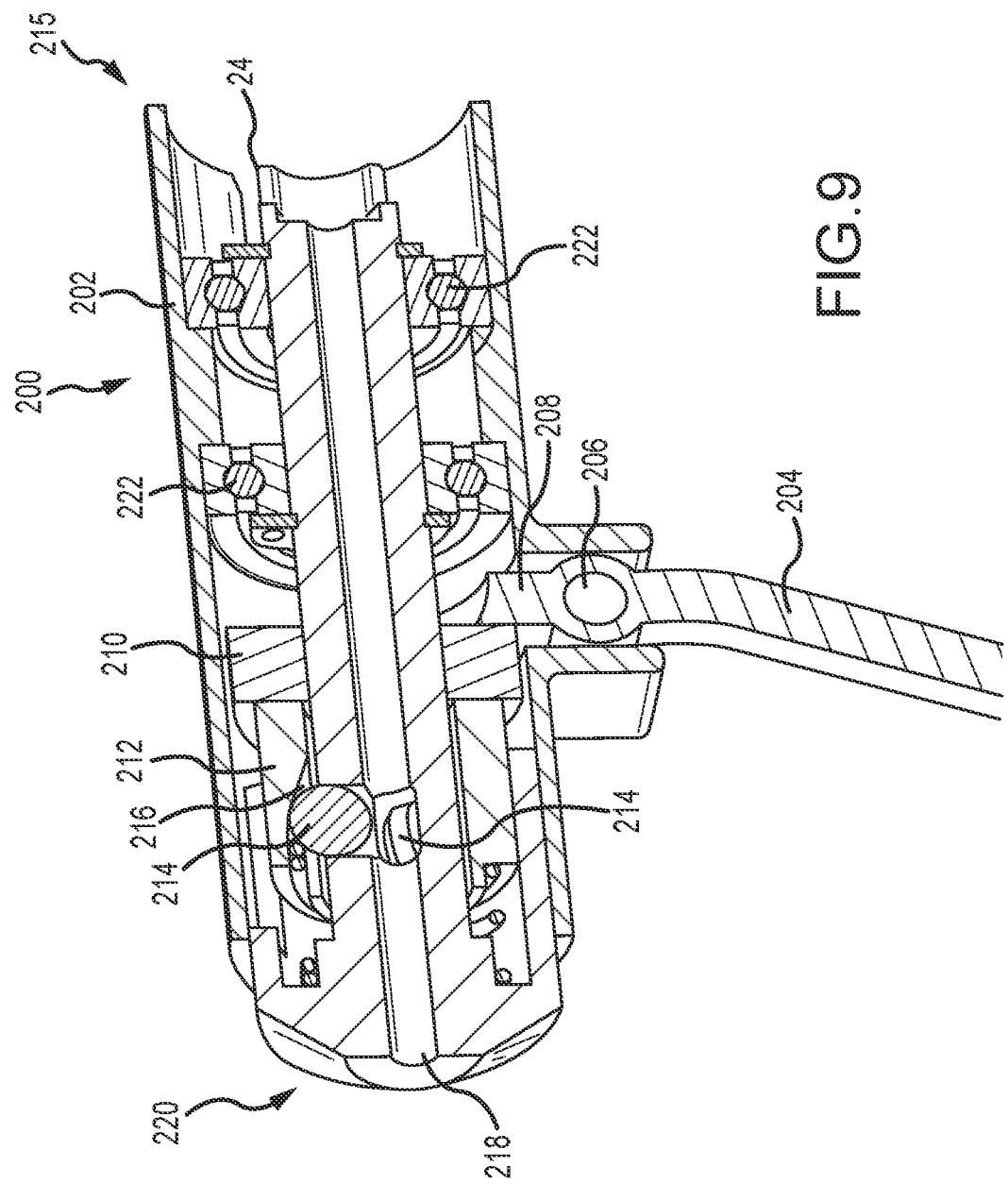
FIG. 9 depicts the embodiment of the chuck of FIG. 7 in cross section along a working axis of the chuck.

With further reference to FIGS. 8 and 9, the internal components of the chuck 200 are depicted. As such, in FIG. 8, the chuck body 202 is not shown for clarity. FIG. 9 is a cross sectional view of the chuck 200 taken along a plane in which the working axis 16 lies. The actuation lever 204 may be engaged with the chuck body 202 at a pivot 206. In turn, upon movement of the actuation lever 204 by the user (e.g., by squeezing of the actuation layer 204 by the user of the instrument 10), the actuation lever 204 may move about the pivot 206. A fork 208 may be disposed opposite the pivot 206 from the lever arm 204. The fork 208 may engage a collar 210 disposed within the chuck body. The collar 210 may comprise or be in contact with a cam member 212. The cam member 212 and collar 210 may be biased toward the proximal portion 215 of the chuck body 202 (i.e., toward the engagement portion of the chuck 200 that interfaces with the instrument 10). The cam member 212 may define cam surfaces 216 that engage locking rollers 214 that may be disposed about the working axis 16. The locking rollers 214 may comprise jaw members that engage the orthopedic implant. The cam surfaces 216 may be configured such that when the cam member 212 is biased proximally (e.g., when the user is not grasping the actuation lever 204), the cam surfaces 216 allow the locking rollers 214 to be displaced away from the working axis 16. In turn, an orthopedic implant 62 may be freely passed into the cannulated passage 218 of the chuck 200. The locking rollers 214 may be displaced away from the cannulated passage 218 to accommodate movement of the orthopedic implant in the cannulated passage 218 in a direction along the working axis 16.

Upon placement of the orthopedic implant 62 at the desired location within the cannulated passage 218, the user may grasp the actuation lever 204. This may cause the fork 208 to advance distally toward the distal end 216 of the chuck 200 as the actuation lever 204 is moved proximally toward the handle of the instrument 10. The distal movement of the fork 208 may overcome the bias force applied to the collar 210 and cam member 212, thus moving the cam member 212 distally. The distal movement of the cam member 212 may advance the cam surfaces 216 relative to the locking rollers 214. The cam surfaces 216 may be contoured such that upon distal advancement of the cam member 212, the locking rollers 214 are urged radially toward the working axis 16. As the locking rollers 214 may be advanced toward the working axis 16, an orthopedic implant disposed in the cannulated passage 218 may be gripped by the locking rollers 214 that are urged toward the working axis 16. In turn, grasping of the actuation lever 204 by the user may result in the locking rollers 214 being urged by the cam surfaces 216 of the cam member 212, thus forcing the locking rollers 214 radially toward the orthopedic implant contained within the cannulated passage 218 prevent axial movement of the orthopedic implant within the cannulated passage 218.

The chuck 200 may also include a chuck drive shaft 24 engageable with the chuck drive coupling 78 to be rotated by the drive system 30. In turn, radial bearings 222 may be provided to support the rotational movement of the chuck drive shaft 24 and/or limit axial movement thereof. The chuck drive shaft 24 may be engaged with the cam member 212 such that rotational movement of the chuck drive shaft 24 also rotates the cam member 212. As such, when the cam member 212 is engaged with an orthopedic implant via the locking rollers 214, the orthopedic implant may also be rotated about the working axis 16.

Figure 10:
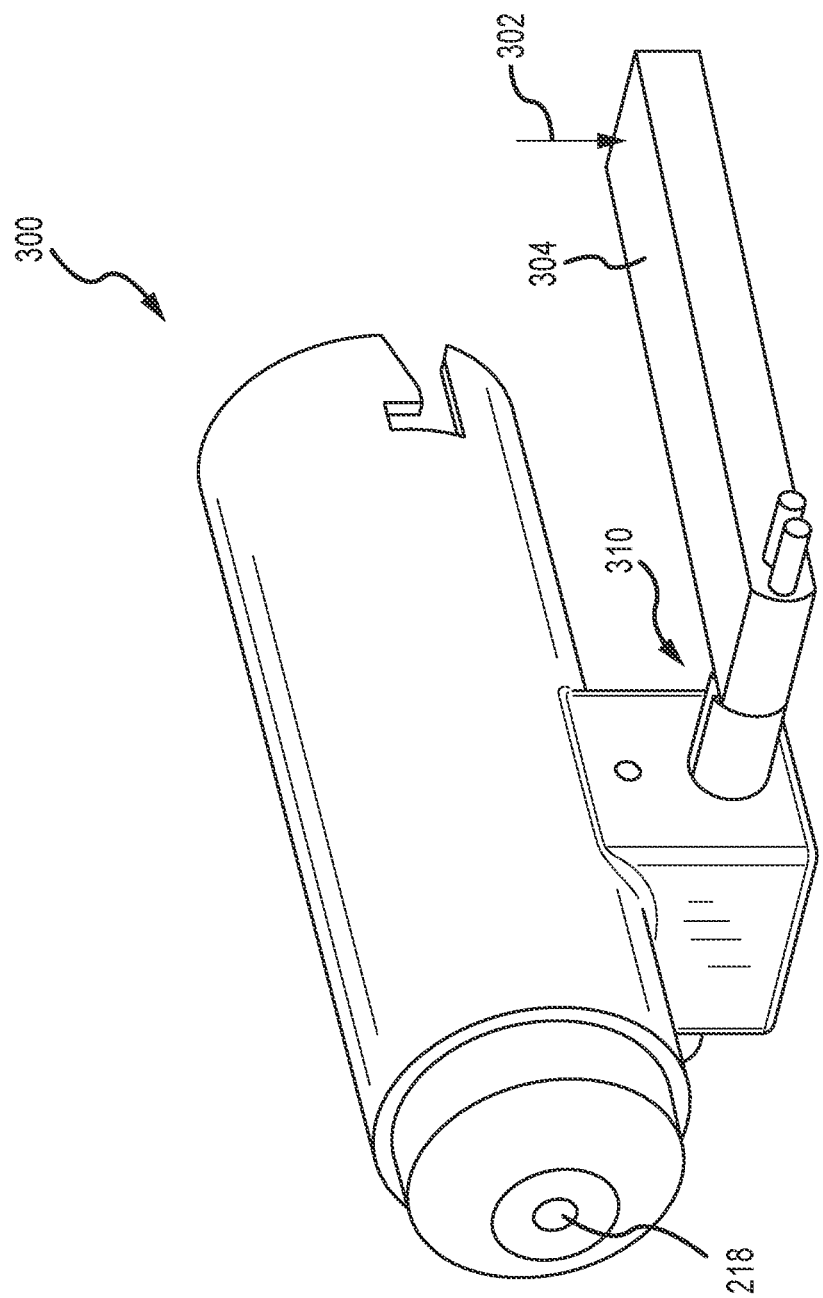
FIG. 10 depicts an embodiment of a chuck that may be used to retain an orthopedic implant.
Figure 11:
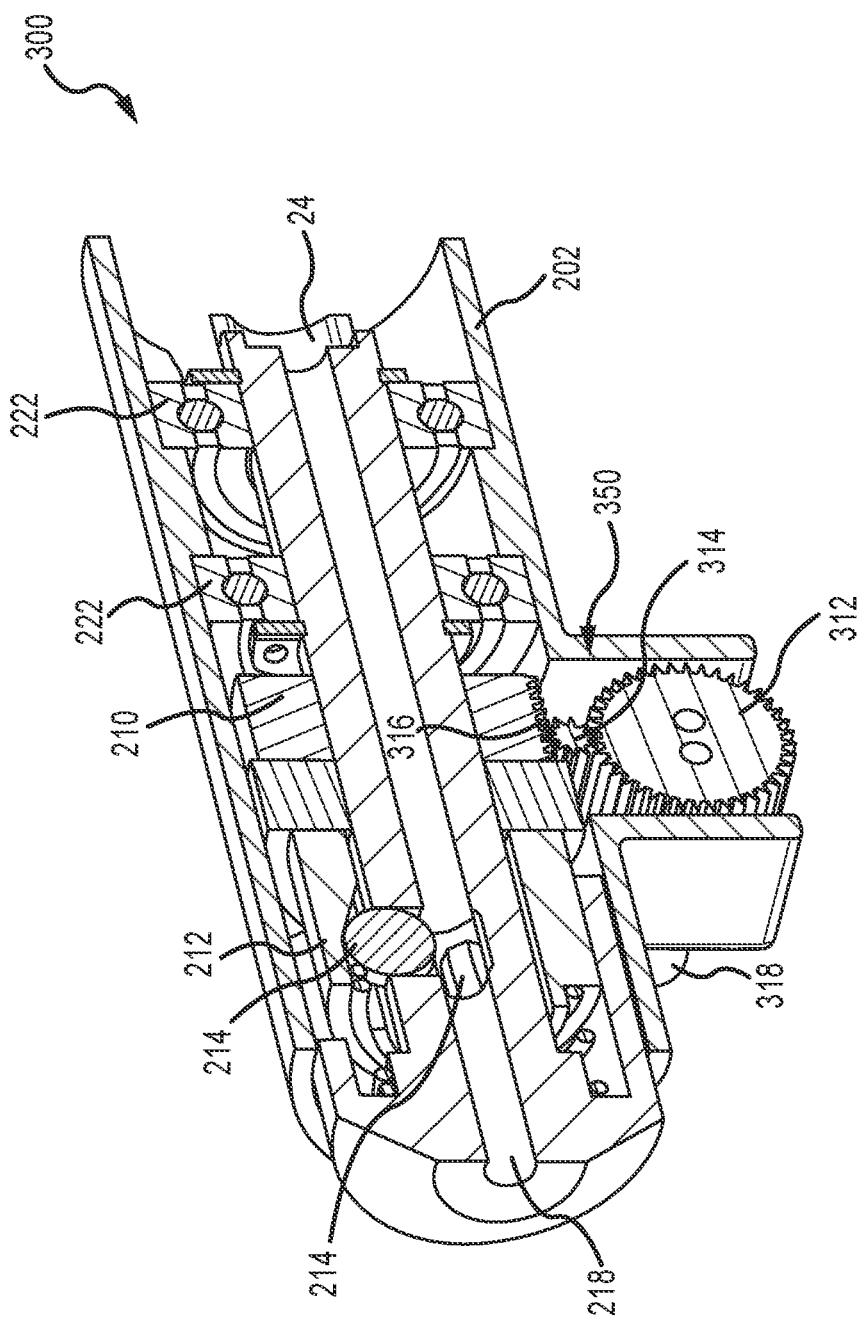
FIG. 11 depicts a cross sectional view of the chuck of FIG. 10 along a working axis of the chuck.

With further reference to FIGS. 10 and 11, another embodiment of a chuck 300 is depicted. The chuck 300 may include an arrangement including a collar 210, cam member 212, and locking rollers 214 similar to that described above in relation to the embodiment 200. However, positioning of the collar 210 and cam member 212 to engage and disengage the locking rollers 214 may be controlled by a rack and pinion mechanism 310. The rack and pinion mechanism 310 may include an actuation lever 304. The actuation lever 304 may be within reach of the user of the instrument 10 when the chuck 300 is engaged therewith. For example, the actuation lever 304 may be reached by a thumb of the user to apply force to the actuation lever 304 when the user utilizes the instrument 10. In this regard, the actuation lever 304 may be placed on either side of the chuck 300 for ambidextrous use by a surgeon.

The actuation lever 304 may be operatively engaged for co-rotation with a gear 312. As such, a force acting in the direction of the arrow 302 in FIG. 10 may cause clockwise rotation of the gear 352 as viewed in FIG. 11. The gear 312 may be meshed with a pinion gear 314 that may engage a rack 316 disposed on the collar 210. In turn, upon application of the force 302, the gear 352 may be urged into clockwise motion, thus urging the pinon gear 314 into counterclockwise motion. This may act upon the rack 316 of the collar 210 to induce movement of the collar 210 distally to position the cam member 212 for selective engagement of the locking rollers 214 with the orthopedic implant disposed in the cannulated passage 218 of the chuck 300. The rack 316 may be locked in this engaged position by a locking member 318. As may be appreciated, upon release of the force 302 (and/or release by the locking member 318), the actuation lever 304, gear 312, and pinion gear 314 may be relaxed or allowed to pivot such that the biasing of the cam member 312 and collar 310 disengages the locking wheels 214 from the orthopedic implant. The locking member 318 may engage when the actuation lever 304 is moved into a position to engage the orthopedic implant 62. In this regard, the locking member 318 may include a locking clutch that prevents rotation of the gear 312 in a direction corresponding to release of the orthopedic implant 62. The locking clutch may be released by movement of the lever actuator 304 in a direction along an axis about which the gear 312 rotates. For instance, the lever actuator 304 may be moved in a direction toward or away from the gear 312 to release the locking clutch to allow the lever actuator 304 to be moved in a direction corresponding to release of the orthopedic implant 62. In other embodiments, the locking member 318 may comprise a pin to fix the gear 312 and/or a fixed gear that is introducible in meshed engagement with the gear 312 to prevent movement thereof.

Figure 12:
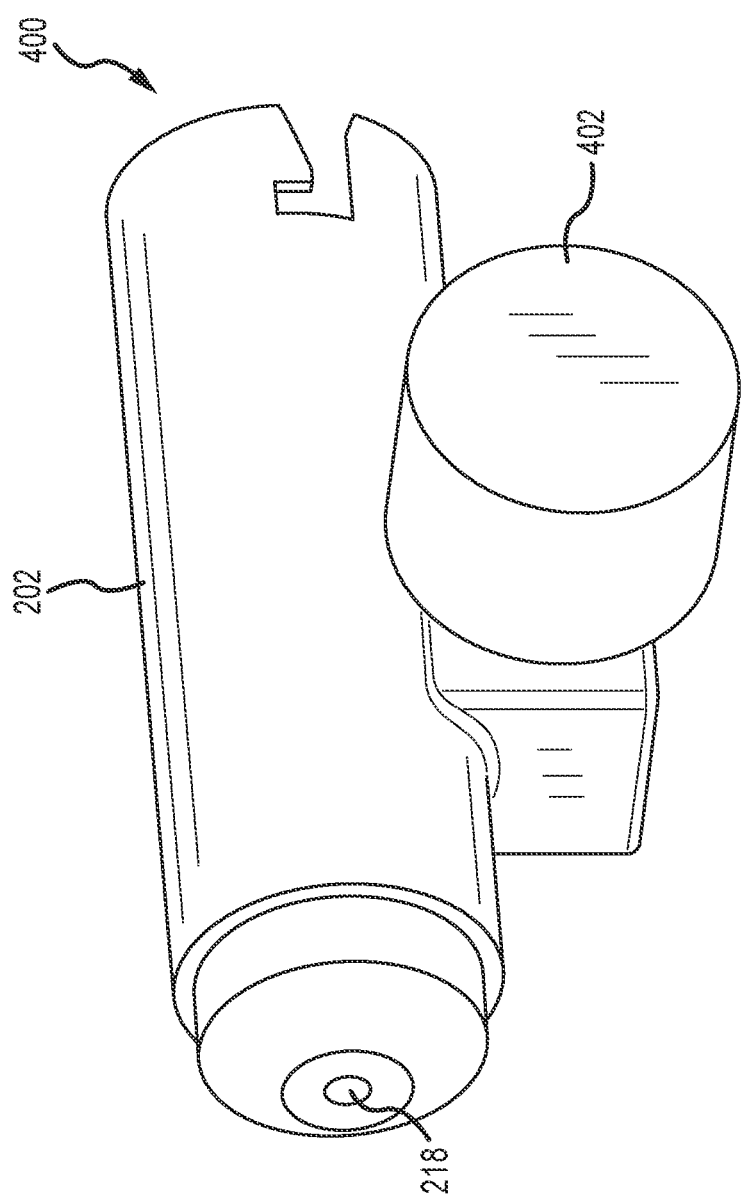
FIG. 12 depicts an embodiment of a chuck that may be used to retain an orthopedic implant.
Figure 13:
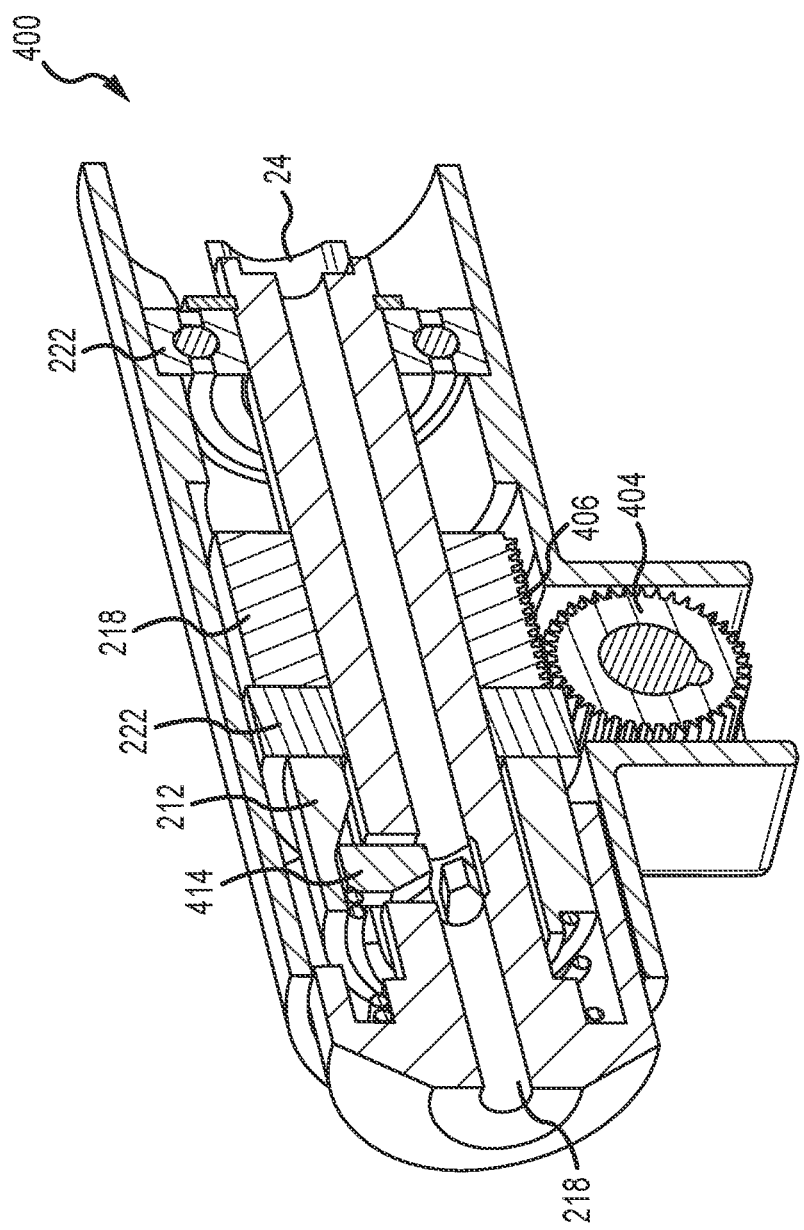
FIG. 13 depicts a cross sectional view of the chuck of FIG. 12 along a working axis of the chuck.

FIGS. 12 and 13 depicted another embodiment of a chuck 400. The chuck 400 may include structure similar to that described in relation to the chuck 300 with the exception that the actuation lever 304 may be replaced with a wheel 402 that may be rotatable for rotation of a gear 404. The gear 404 may be directly engaged with a rack 404 disposed on the collar 210. In turn, movement of the collar 210 to urge the cam member 212 may result from rotation of the wheel 402.

Also, the embodiment of the chuck 400 may include cam blocks 414 rather than locking wheels 212. The cam blocks 414 may still interact with the cam surfaces 216 of the cam member 212 such that the cam blocks 414 engage and disengage an orthopedic implant with distal and proximal movement of the cam member 212, respectively. In this regard, the cam blocks 414 may comprise jaw members of the chuck 400.

Figure 14A:
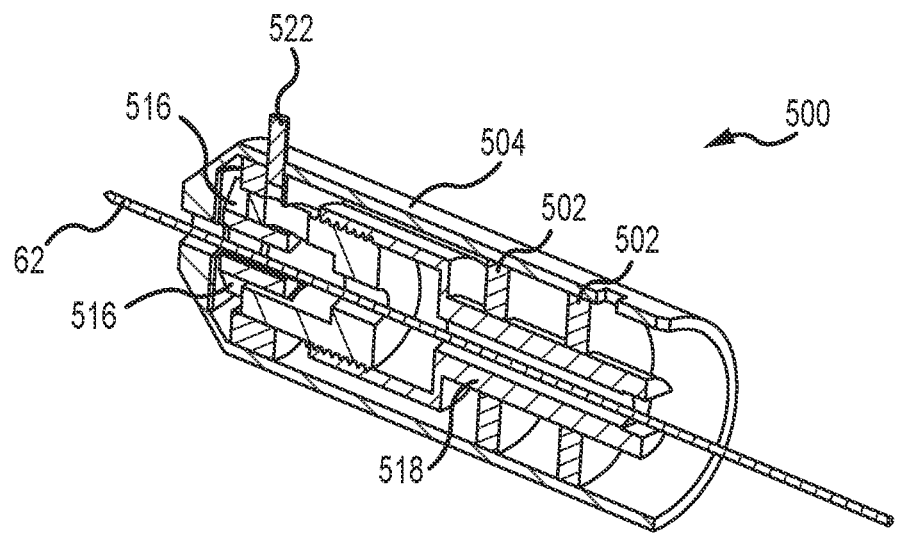
FIGS. 14A and 14B depict an embodiment of a chuck that may be used to retain an orthopedic implant that is shown in cross section along a working axis of the chuck.
Figure 14B:
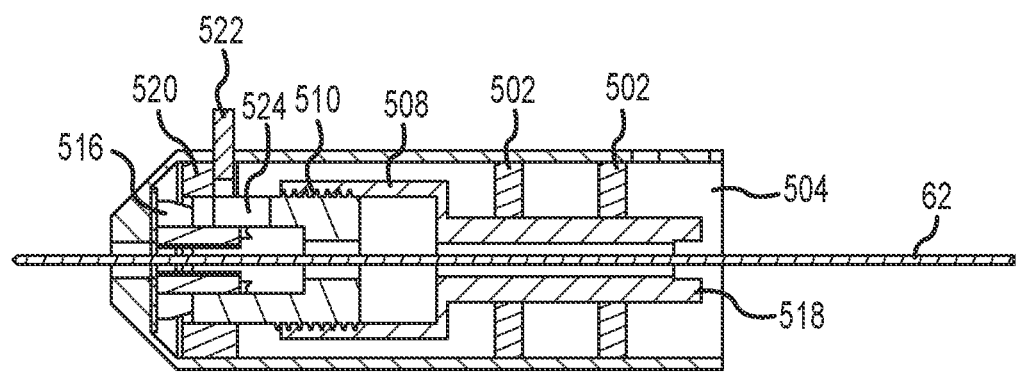
Figure 15:
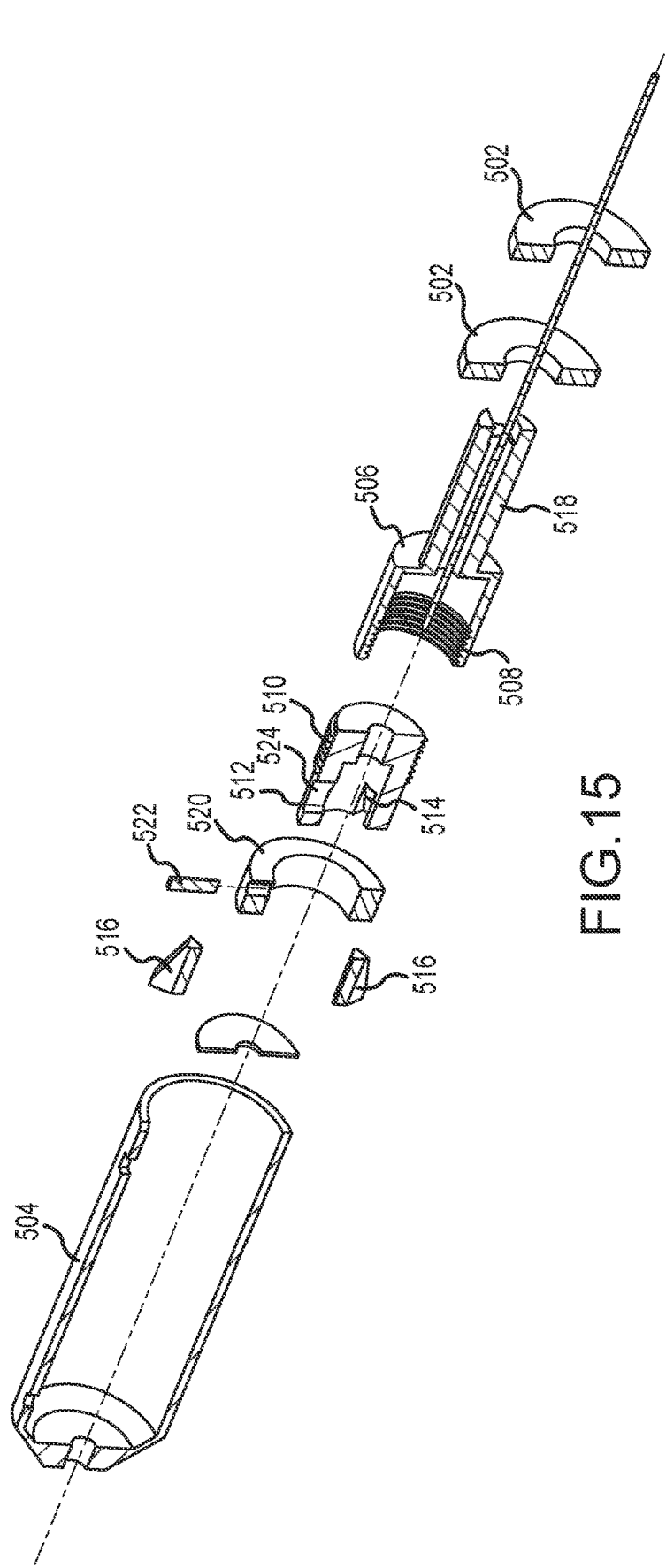
FIG. 15 depicts an exploded view of the chuck of FIG. 14.

FIGS. 14A, 14B, and 15 depict another embodiment of a chuck 500 may be utilized to engage an orthopedic implant 62 disposed within a cannulated passage 518 defined by the chuck 500. The chuck 500 may include a plurality of bearings 502 disposed within a chuck housing 504. The bearings 502 may support a chuck driveshaft 506. The chuck driveshaft 506 may be adapted for engagement with the chuck engagement coupling 78 of the instrument 10. That is, the instrument may impart rotational movement of the chuck driveshaft 506. Chuck driveshaft 506 may include a threaded surface 508. The threaded surface 508 may be threadably engageable with a threaded portion 510 of a cam member 512. In this regard, the cam member 512 may be threadably engaged with the threaded surface 508 of the chuck driveshaft 506. As such, relative rotational motion between the cam member 512 and the chuck driveshaft 506 may cause relative axial movement between the cam member 512 and the chuck driveshaft 506 as the threads engage and disengage with motion. The cam member 512 may include cam surfaces 514. The cam surfaces 514 may contact chuck blocks 516. In this regard, the cam blocks 516 may be maintained against the cam surfaces 514 of the cam member 512 such that the cam blocks 516 are urged radially toward the working axis 16 upon distal movement of the cam member 512 as described above. The chuck blocks 516 may comprise jaw members of the chuck 500.

The cam member 512 may be aligned with an annular support 520 that may be disposed within the cam body 504. The annular support 520 may include a rod 522 that may extend externally to the cam body 504. The rod 522 may be supported by the annular support 520 and be biased in a direction radially away from the working axis 16. The cam member 512 may comprise a slot 524 that may be alignable with the rod 522 supported by the annular support 520. As such, when the slot 524 and the rod 522 are aligned, the rod 522 may be displaced from the externally extending portion of rod 522 extending outside the cam body 504 such that the rod 522 may be advanced radially toward the working axis 16 beyond the annular support 520 and into the slot 524. The slot 524 may be dimensioned to allow for axial movement of the cam member 512 when the rod 522 is disposed in the slot 524, but the rod 522 may engage the cam member 512 to prevent rotation of the cam member 512 about the working axis 16. That is, advancement of the rod 522 into the slot 524 of the cam member 512 may cause the cam member 512 to be locked relative to radial rotation about the working axis 16. In turn, continued operation of the instrument 10 to induce rotation of the cam driveshaft 504 may result in relative rotation between the driven cam driveshaft 506, which rotates, and the locked cam member 512, which is prevented from rotation by the rod 522. In turn, the relative rotational movement between the internally threaded surface 508 and the threaded portion of the cam member 512 may induce relative axial movement between the cam member 512 and the chuck driveshaft 506. This relative axial movement may cause the cam member 512 to be moved distally to engage the cam blocks 516 such that the cam blocks 516 are urged by the cam surfaces 514 of the cam member 512 to move the cam blocks 516 radially toward the axis 16 to engage the orthopedic implant 62.

In turn, the rotational motion imparted by the instrument 10 may be utilized to engage and disengage the orthopedic implant 62 of the chuck 500 when the rod 522 is depressed into the slot 524. That is, upon normal operation where the rod 522 may be biased radially away from the axis 16 such that the slot 524 of the cam member 512 is not engaged by the rod 522, the cam member 512 may co-rotate with chuck driveshaft 506 for normal operation. As the cam member 512 may engage an orthopedic implant 62, the orthopedic implant may also be rotated when engaged by the cam member 512. Upon engagement of the rod 522 with the slot 524 such that the rod 524 prevents radial movement of the cam member 512, continued operation of the instrument 10 may result in relative rotational motion of the chuck driveshaft 506 and the cam member 512. As such, the instrument 10, upon engagement of the rod 522 with the slot 524 of the cam member 512, may be utilized to advance and retract the chuck blocks 516 to engage and disengage the orthopedic implant 62.

With further reference to FIGS. 50-56 another embodiment of a chuck 550 is depicted. Like a number of the chucks described above, the chuck 550 may allow for engagement of an orthopedic implant 62 (not shown in FIGS. 50-56) without requiring external force be applied by a user of the instrument. In this regard, the chuck 550 may be utilized in conjunction with an instrument 10 having a measurement system 40 as described. Because the chuck 550 may not require application of an external force to the chuck 550 to maintain engaged with the orthopedic implant, the chuck 550 may provide more precise and accurate measurements resulting from the measurement system 40. Moreover, as may be appreciated from the discussion to follow, the chuck 550 may allow for engagement of an orthopedic implant when the chuck 550 is moved in a direction to advance the orthopedic implant 62 relative to the bone of the patient. However, the chuck 550 may, in at least some states, allow for retraction of the chuck 550 relative to the orthopedic implant such that the chuck 550 disengages automatically upon retraction of the chuck 550 from the orthopedic implant. In this regard, the chuck 550 may be utilized such that the chuck 550 engages the orthopedic implant 62 upon a motion tending to advance the orthopedic implant 62 linearly relative to the bone of the patient. Additionally, the chuck 550 may be readily retracted relative to the orthopedic implant such that repeated advancement in retraction may be accomplished without requiring the user to take additional action to engage and disengage the chuck 550 with the orthopedic implant other than merely advancing and retracting the chuck 550 relative to the orthopedic implant.

Figure 50:
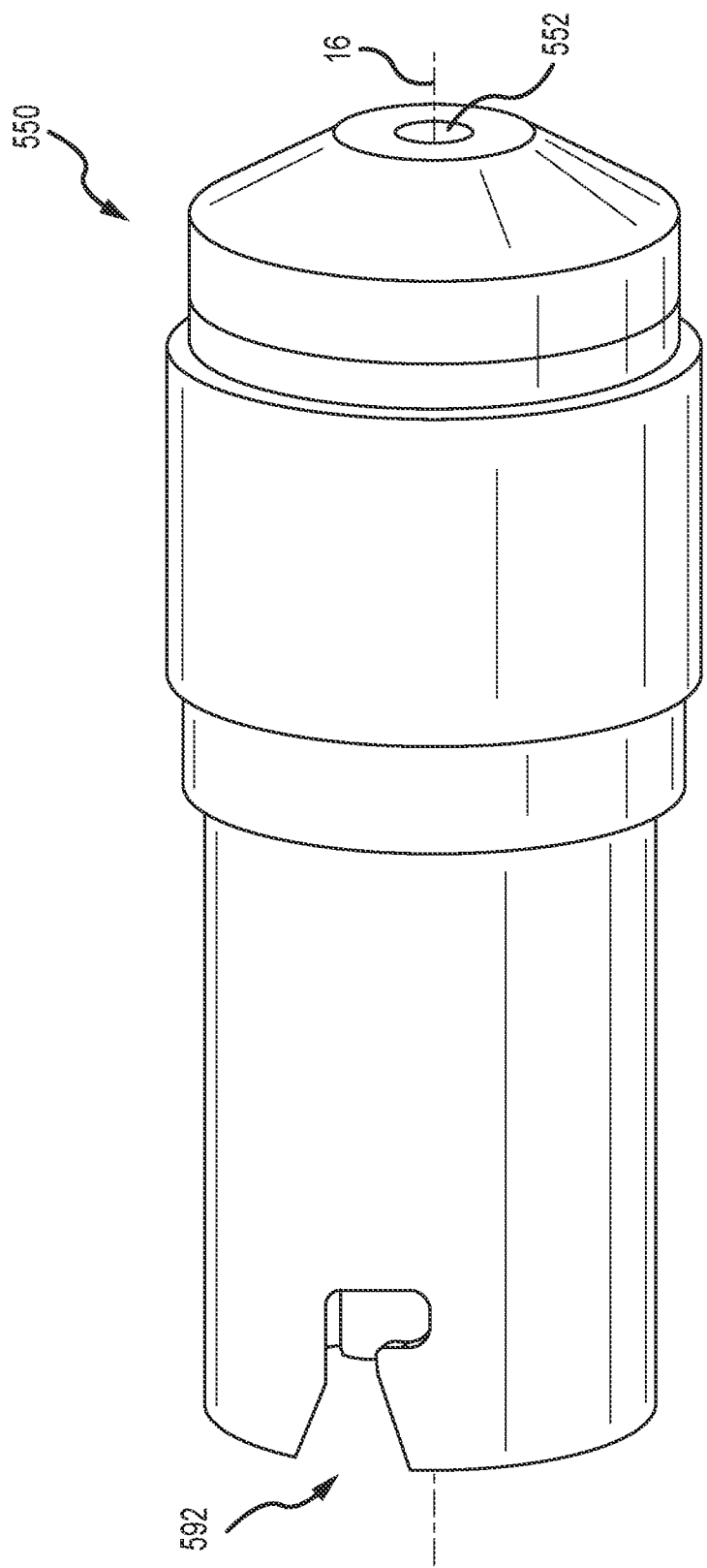
FIG. 50 depicts an embodiment of a chuck.

With specific reference to FIG. 50, the chuck 550 may include a cannulated passage 552 that generally extends along a working axis 16 of the chuck 550. Specifically, the cannulated passage 552 may be aligned with the cannulated passage 76 of the instrument 10 to accept an orthopedic implant 62 relative to the cannulated passage 76 and the cannulated passage 552. In this regard, the chuck 550 may include an engagement portion 592 at a proximal end thereof that may engage the instrument 10 in the manner described in relation to FIGS. 5-6B above. In this regard, the chuck 550 may be used interchangeably with the instrument 10 as described above.

Figure 51:
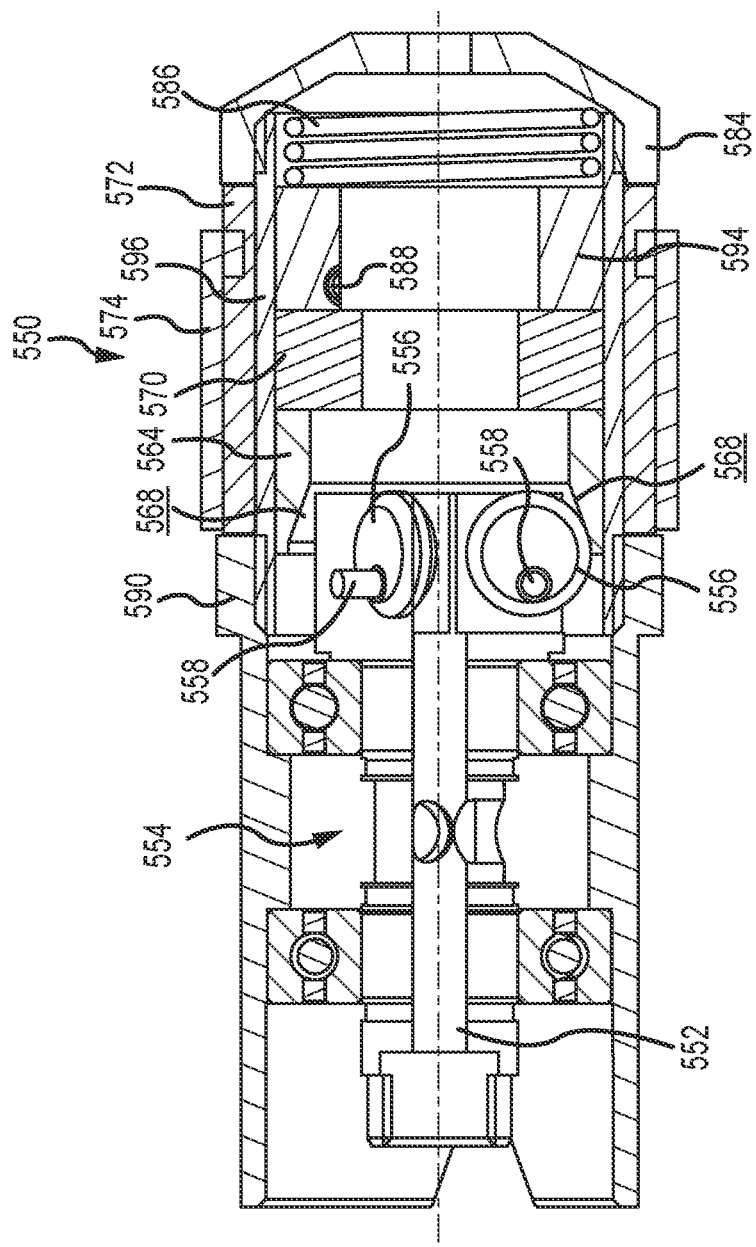
FIG. 51 depicts the embodiment of the chuck of FIG. 50 in a cross-sectional view taken along the working axis of the chuck.
Figure 52:
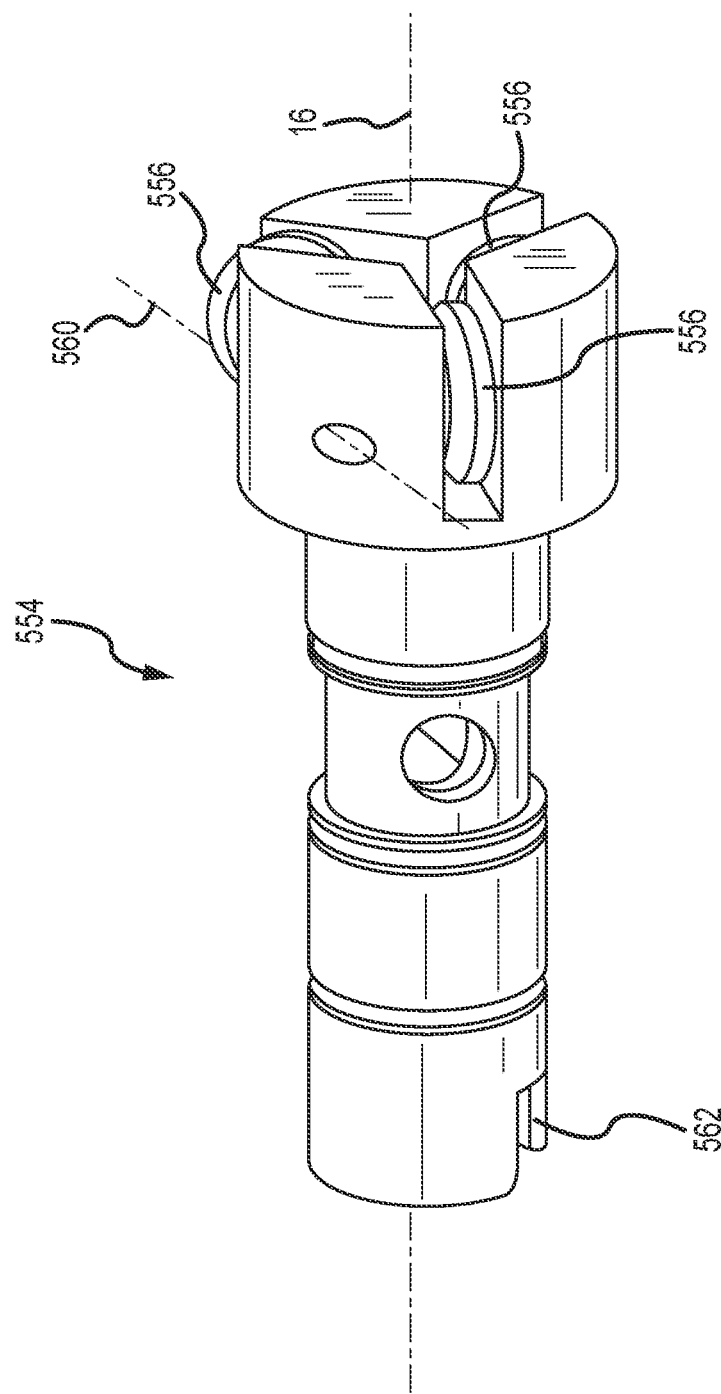
FIG. 52 depicts an orthopedic implant engagement portion of the embodiment of the chuck of FIG. 50 in isolation.
Figure 53:
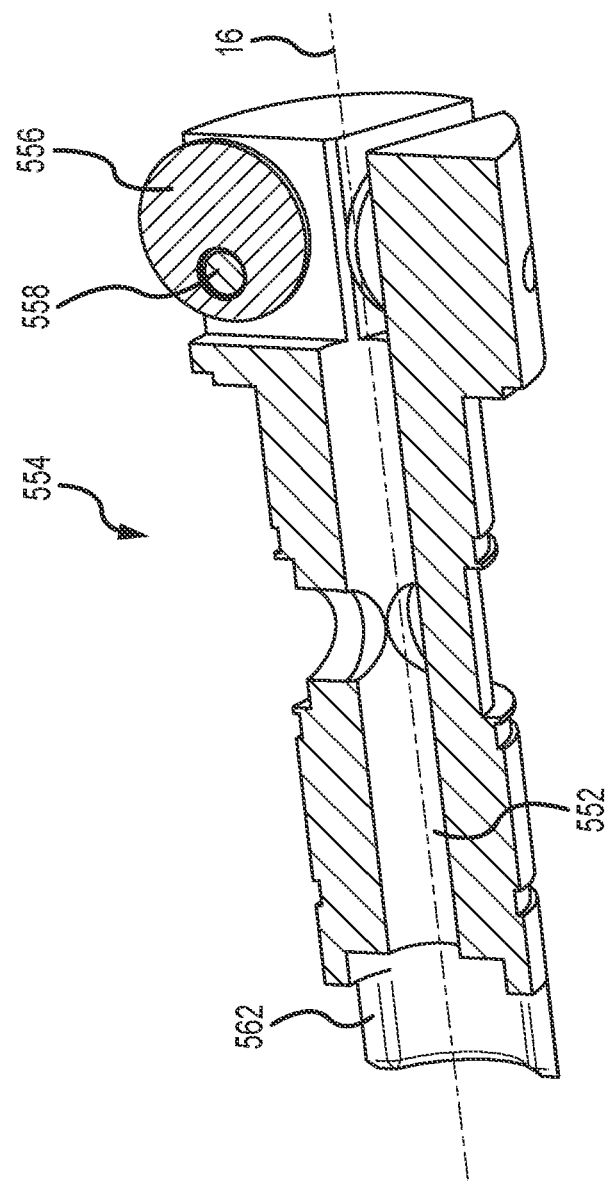
FIG. 53 depicts the implant engagement portion of FIG. 52 in cross section along the working axis of the chuck.

FIG. 51 depicts a cross-sectional view of the chuck 550 taken along the working axis 16. The chuck 550 may include an orthopedic implant engagement portion 554. With additional reference to FIGS. 52 and 53, the orthopedic implant engagement portion 554 is shown in isolation. The orthopedic implant engagement portion 554 may include a drive shaft 562 that may engage a chuck drive coupling 78 as described above. In this regard, the instrument 10 may be operative to impart rotational motion to the orthopedic implant engagement portion 554 when the engagement portion 592 is engaged with the instrument 10.

The orthopedic implant engagement portion 554 may also include a plurality of roller members 556. The roller members 556 may be disposed radially about the cannulated passage 552. The roller members 556 may comprise a plurality of jaw members that are used to engage an orthopedic implant disposed in the cannulated passage 552. While three roller members 556 are shown, additional or fewer roller members may be provided. As shown, the roller members 556 may be disposed about the working axis 16 such that the rollers 556 are disposed at various radial positions about the cannulated passage 556. The roller members 556 may be evenly spaced about the cannulated passage 556. While not shown, the roller members 556 may be provided in opposing pairs such that each roller member 556 may have a coordinating roller member 556 spaced opposite the cannulated passage 556. This arrangement may assist in imparting a clamping force to an orthopedic implant as described in greater detail below.

The roller members 556 may be engaged with the orthopedic implant engagement portion 554 such that the roller members 556 are pivotal about an axle member 558. The axle member 558 may define a pivot axis 560. Specifically, the pivot axis 560 may be orthogonal to the working axis 16 and offset there from. In turn, the roller members 556 may be operative to pivot toward or away from the working axis 16 upon pivotal movement about the axle 558. With specific reference to FIG. 53, it may be appreciated that upon clockwise rotation of the roller member 556 shown in cross-section in FIG. 53, the roller member 556 may pivot toward the working axis 16. In turn, clockwise rotation of the roller member 556 may result in the roller member 556 engaging an orthopedic implant disposed within the cannulated passage 552.

Figure 54:
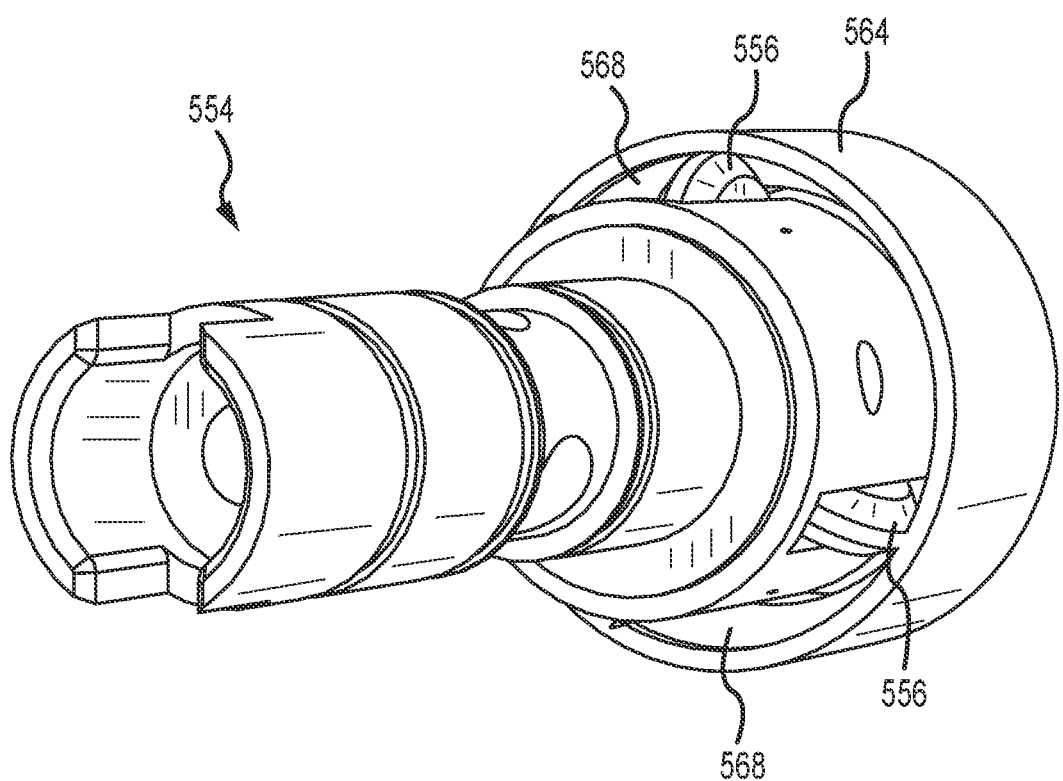
FIG. 54 depicts the implant engagement portion of FIG. 52 and a rear perspective view depicting engagement of the jaw members with an arcuate ramp surface.

With further reference to FIG. 54, the orthopedic implant engagement portion 554 is shown in relative position with a cam member 564, which is also depicted in FIG. 51. Specifically, the cam member 564 may include an annular ramp surface 568 that may be disposed so as to contact the roller members 556 of the orthopedic implant engagement portion 554 on a side of the roller members 556 opposite the side adjacent to the working axis 16. With returned reference to FIG. 51, the cam member 564 may be abutted distally with a bearing 570 that is in turn distally abutted by a drive ring 594. A biasing member 586 may be deposed distally to the drive ring 594 and between the drive ring 594 and an endcap 584 of the chuck 550. The biasing member 586 may serve to bias the drive ring 594, bearing 570, and cam member 564 proximally such that the ramped surface 568 engages with and urges the roller members 556 toward the working axis 16.

Accordingly, it may be appreciated that when an orthopedic implant is disposed in the cannulated passage 552, the roller members 556 may be biased into contactable engagement with the orthopedic implant upon influence by the ramp surface 568 of the cam member 564, which is biased proximally by the biasing member 586. Additionally, the axle 558 may engage the roller member 556 in an eccentric manner relative to the roller member 556. In turn, the pivotal axis 560 of the roller member 556 may be located proximally relative to the center of the roller member 556. In this regard, as the chuck 550 is advanced distally relative to the orthopedic implant 62, the roller member 556 may contact the orthopedic implant. The frictional engagement between the roller member 556 and the orthopedic implant may cause the roller member to experience a moment acting on the roller member 556 that tends to pivot the roller member 556 about the axle 558, thus driving the roller member 556 toward the working axis 16. That is, as the chuck 550 is advanced distally relative to an orthopedic implant with which the roller member 556 is in contact, the roller member 556 is further urged into engagement with the orthopedic implant such that the orthopedic implant engagement portion 554 clampingly engages the orthopedic implant.

However, upon a motion to retract the chuck 550 relative to the orthopedic implant, the frictional engagement between the orthopedic implant in the roller member 556 may cause the roller member to undergo pivotal rotation about the axle 558 in a direction opposite of that when the chuck 550 is advanced. The motion to retract the chuck 550 may result in the roller member 556 being frictionally engaged to induce a moment on the roller member 556 that rotates the roller member 556 in a direction opposite of that when the chuck 550 is advanced such that the roller member 556 is displaced away from the working axis 16. In turn, the roller member 556 may bear against the ramp surface 558 causing the cam member 564, bearing 570, and drive ring 594 to move distally against the force of the biasing member 586. In turn, the roller member 556 may be displaced away from the orthopedic implant, thus allowing the chuck 550 to be withdrawn proximally relative to the orthopedic implant. However, upon further advancement of the chuck 550 distally relative to the orthopedic implant, the roller member 556 may again be pivoted about the axle 558 in a direction tending to rotate the roller member 556 in a direction towards the working axis 16 to again clampingly the orthopedic implant disposed within the cannulated passage 552.

Figure 55:
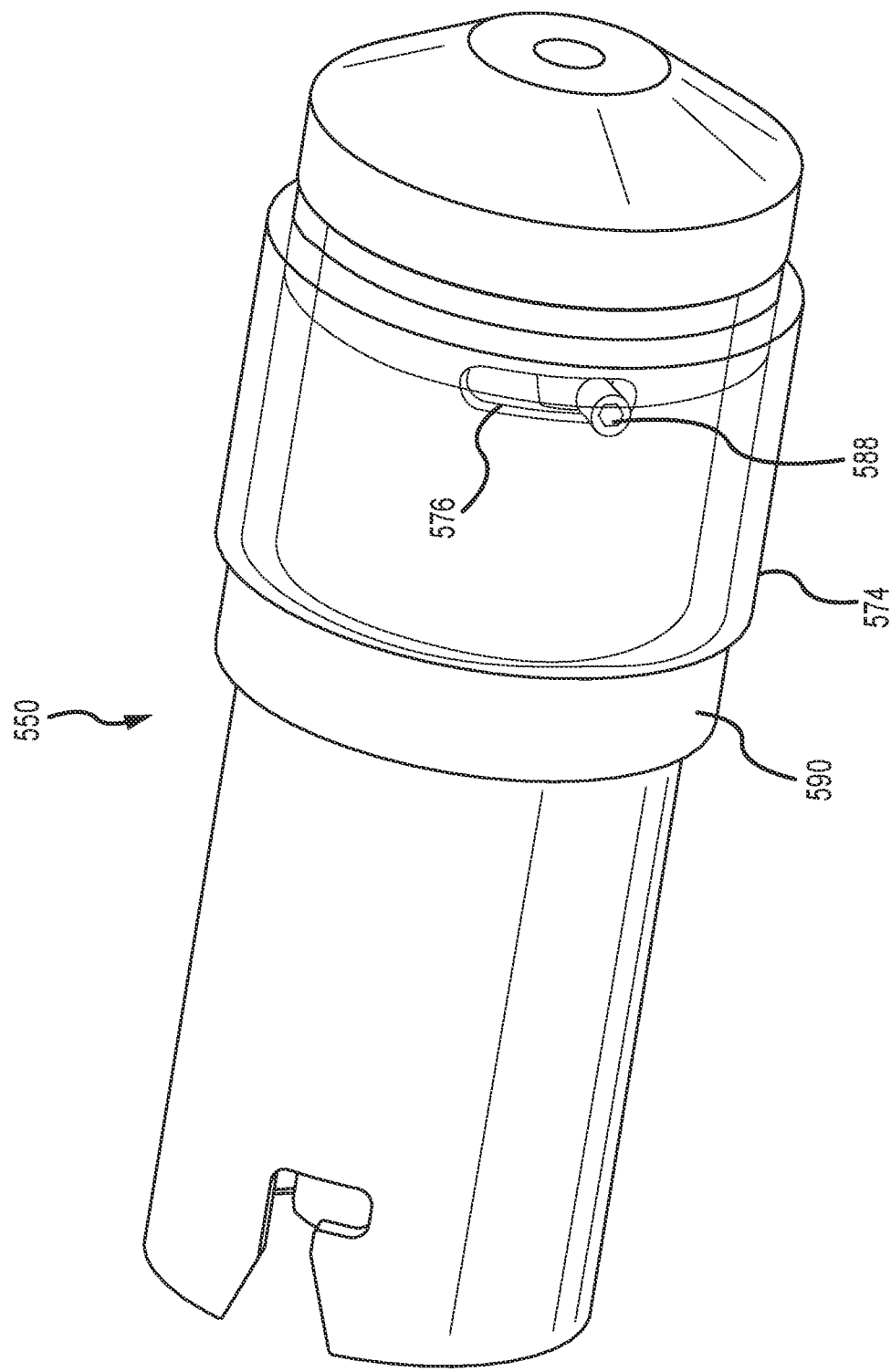
FIGS. 55-56 depict the chuck of FIG. 50 with portions thereof shown in phantom to illustrate utilization of a control ring of the chuck for disposing the chuck between various states of engagement of the orthopedic implant.
Figure 56:
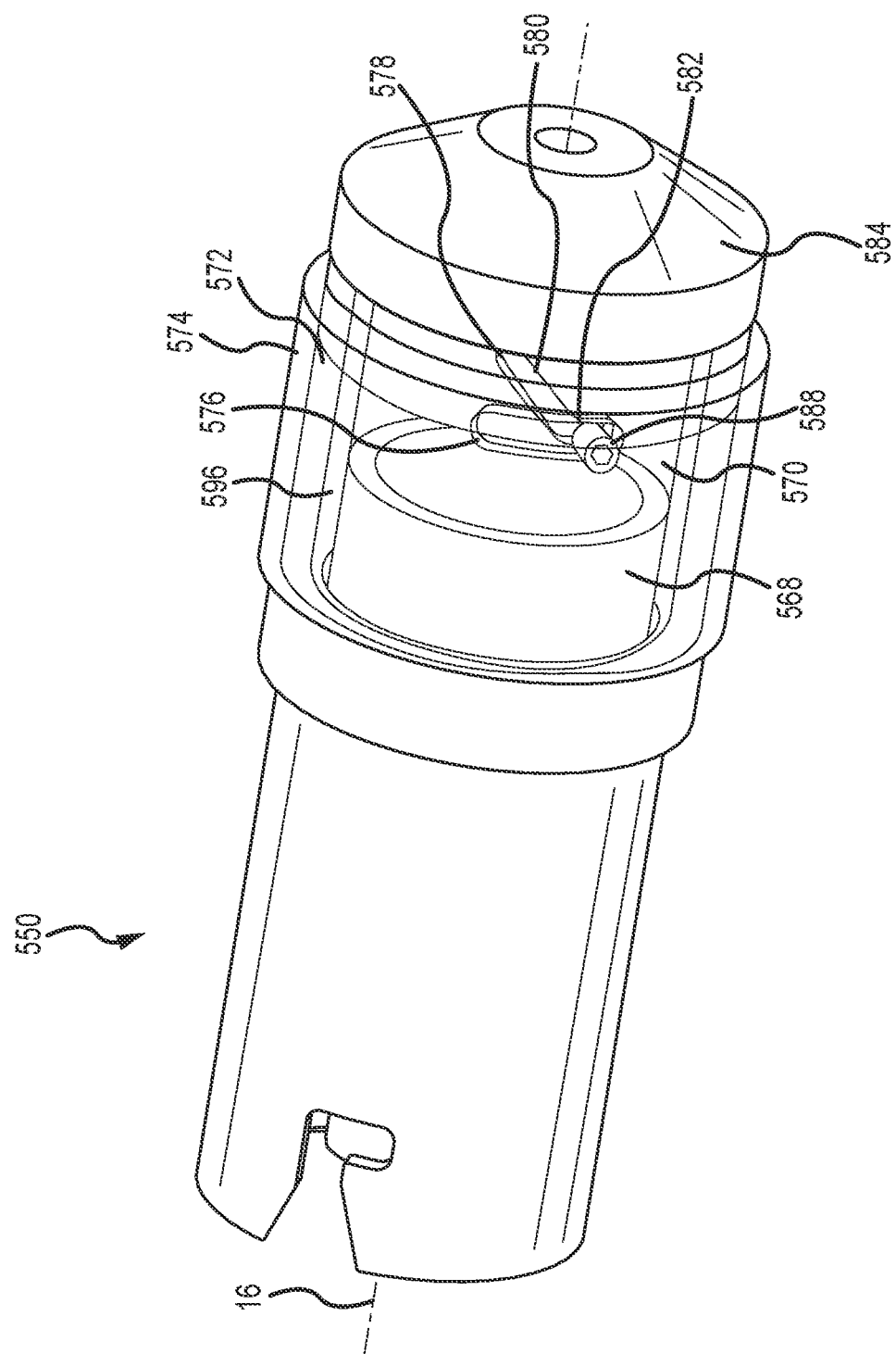

Thus, the operation of the chuck 550 may include a biased state wherein the chuck 550 may clampingly engage an orthopedic implant upon a linear motion of advancement of the chuck 550 relative to the orthopedic implant. Such engagement of the orthopedic implant upon the motion of linear advancement of the chuck 550 may result from the biasing force imposed by the biasing member 586 on the cam member 564 such that the ramp 568 causes the roller members 556 to contact the orthopedic implant disposed within the cannulated passage 552 of the chuck 550. However, the chuck 550 may also be disposed in a number of alternative states, namely a locked open and a lock closed state. The various states of the chuck 550 may be controlled by operation of a control ring 572. Namely, the control ring 572 may have a set screw 588 engaged with the control ring 572 and extending radially toward the working axis 16. The set screw 588 may extend through a side wall 596 of the chuck 550 and be disposed within a slot 580 that is provided in the drive ring 594 as best seen in FIGS. 55-56.

The slot 580 may include an angled portion 578 extending relative to the ring member 594. When the set screw 588 is disposed in the angled portion 578 of the slot 580, the control ring 572 and set screw 588 may allow the drive ring 594 to freely move relative to the set screw 588. That is, movement of the drive ring 594, and in turn the cam member 564, may be unrestrained for proximal and distal axial movement with concurrent movement of the set screw 588 relative to the angled portion 578 of the slot 580. In turn, upon influence of the biasing member 586 and in response to the influence of the roller members 556 on the ramp surface 568, the ring member 594 may be allowed to freely move when the set screw 588 is disposed within the angled portion 578 of the angled slot 580. In addition to the slot 580, a guide slot 576 may be defined in the chuck sidewall 596. The set screw 588 may also pass through the guide slot 576 of the chuck sidewall 596. The guide slot 576 may extend circumferentially along a portion of the circumference of the chuck sidewall 596 that corresponds to the circumferential extent of the slot 580. In turn, as the set screw 588 traverses along the angled portion 578 of the slot 580, the set screw 588 may also move relative to the guide slot 576. In this regard, the control ring 572 may rotate circumferentially upon movement of the drive ring 594 in a proximal or distal axial direction.

Additionally, the angled slot 580 may include a flat portion 582 that extends circumferentially. When the control ring 572 is rotated so as to disposed the set screw 588 in the flat portion 580, the ring member 594 may be prevented from moving axially. Specifically, the flat portion 582 may be at the proximal end of the angled slot 580. In this regard, when the set screw 588 is disposed in the flat portion 582, the ring member 594 may be disposed in a locked axial position that is a distal position, thus locking the ring member 594 distally against the influence of the biasing member 586 such that the cam member 564 and ramp surface 568 do not bear upon the roller members 556. Accordingly, motion of the roller member 556 in either movement of advancement or retraction relative to an orthopedic implant disposed within the cannulated portion 552 may not result in sufficient frictional engagement between the roller member 556 and the orthopedic implant to result in movement of the roller member 556. In turn, when the set screw 588 is disposed within the flat portion 582 of the angled slot 580, the ring member 594 may be locked distally such that the chuck 550 is in a locked open state and the chuck 550 does not engage the orthopedic implant whether moved in a linear motion of advancement or retraction relative to the orthopedic implant.

Additionally, the chuck 550 may be also disposed in a lock closed state. In this regard, a threaded sleeve 574 may be disposed on the control ring 572. The threaded sleeve 574 may be threadably engaged with the control ring 572. In turn, the threaded sleeve 574 may be moved in threaded engagement relative to the control ring 572 such that the threaded sleeve 574 abuts a bulkhead 590 of the chuck 550. In turn, when the threaded sleeve 574 is tightened against the bulkhead 590, any rotation of the control ring 572 may be prevented. As such, the set screw 588 may not be allowed to traverse within the guide slot 576. In this regard, the set screw 588 may also prevent distal movement of the drive member 594, bearing 570, and cam member 564. In this regard, the roller members 556 may be locked into engagement with an orthopedic implant disposed within the cannulated passage 552. In this regard, even upon a motion of retraction of the chuck 550 relative to the orthopedic implant 62, the roller member 556 may not be allowed to displace the cam member 564 such that the roller member 556 remains engaged with the orthopedic implant even upon retraction.

FIGS. 57-66 illustrate a further embodiment of a chuck 950 may be utilized to engage an orthopedic implant (not shown) upon relative motion of the chuck 950 relative to the orthopedic implant. In contrast to the embodiment of the chuck 550 described above, the chuck 950 may have a state in which the chuck 950 may engage the orthopedic implant upon relative rotational motion of the chuck 950 in relation to the orthopedic implant. In this regard, upon rotation in a first direction (e.g., clockwise), the chuck 950 may be operative to engage the orthopedic implant for advancement thereof. However, counter rotation (e.g., counterclockwise) of the chuck 950 relative to the orthopedic implant may allow for the orthopedic implant to be disengaged by the chuck 950. In turn, upon the counter rotation of the chuck 950 relative to the orthopedic implant, the chuck 950 may be retracted relative to the orthopedic implant. Upon further rotation of the chuck 950 relative to the orthopedic implant, the orthopedic implant may be again engaged for further advancement thereof. In this regard, the embodiment of the chuck 950 depicted in FIGS. 57-66 may allow for selective engagement and disengagement of the orthopedic implant of the chuck 950 without requiring a user to actively interface with the chuck 950 for engagement and disengagement of the chuck 950 with the orthopedic implant. In addition, the chuck 950 may engage the chuck upon linear advancement of the chuck 950 as described above in relation to the embodiment of the chuck 550.

Figure 57:
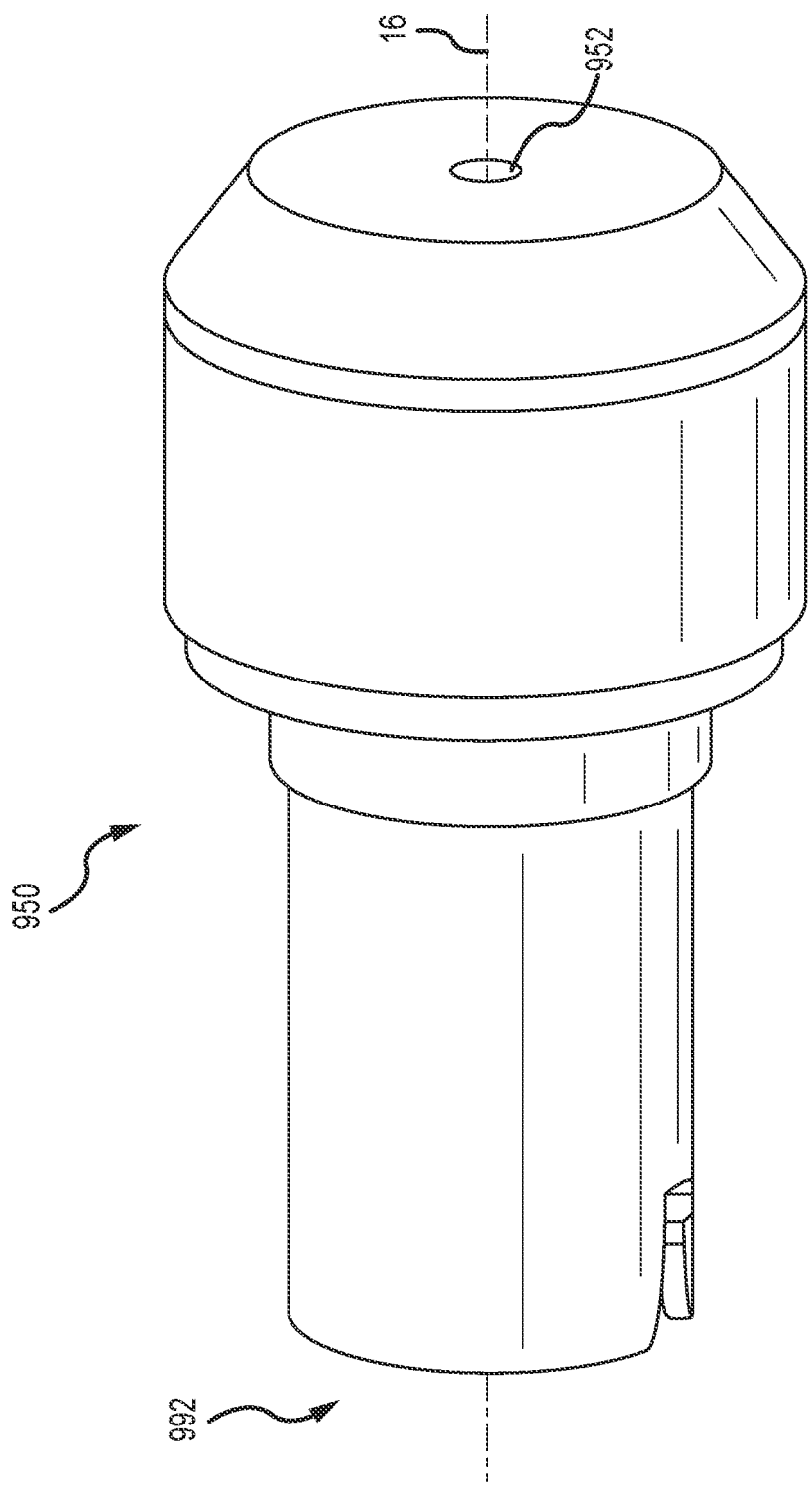
FIG. 57 depicts an embodiment of a chuck.

With initial reference to FIG. 57, the chuck 950 may include a cannulated passage 952 that generally extends along a working axis 16 of the chuck 950. Like the cannulated passage 552 described above in relation to chuck 550, the cannulated passage 952 may be alignable with a cannulated passage 76 of an instrument 10 to accept an orthopedic implant 62 (not shown in FIGS. 57-66) in the cannulated passage 76 and cannulated passage 952. The chuck 950 may also include an engagement portion 952 at the proximal end thereof that may engage the instrument 10 in the manner described in relation to FIGS. 5-6B above. Accordingly, the chuck 950 may also be interchangeable with the instrument 10 in a manner as described above.

Figure 58:
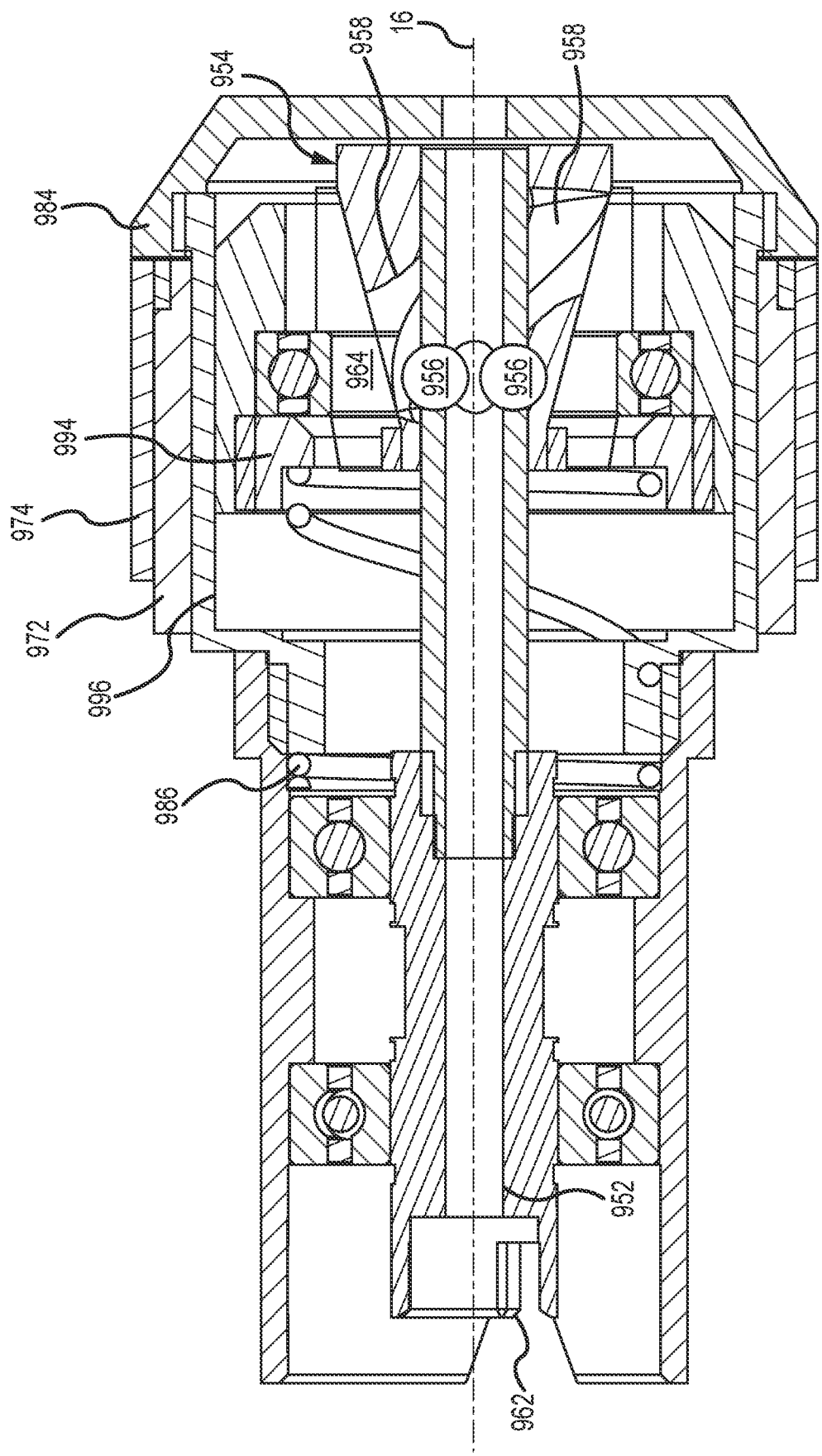
FIG. 58 depicts the embodiment of the chuck of FIG. 57 in a cross-sectional view taken along the working axis of the chuck.
Figure 59:
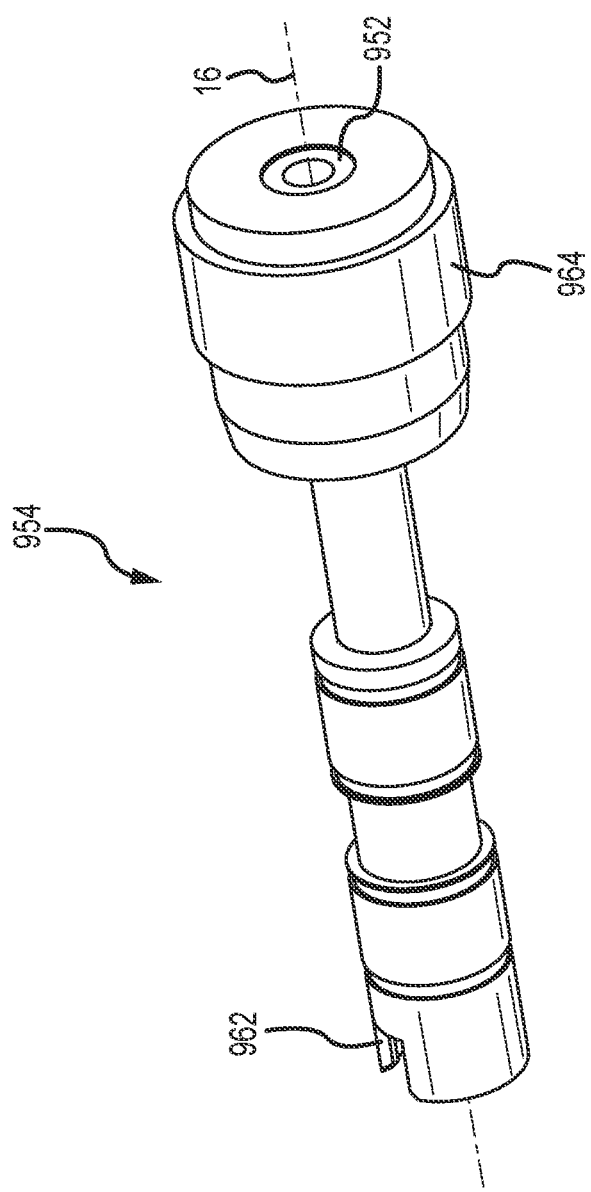
FIG. 59 depicts an orthopedic implant engagement portion of the embodiment of the chuck of FIG. 57 in isolation.
Figure 60:
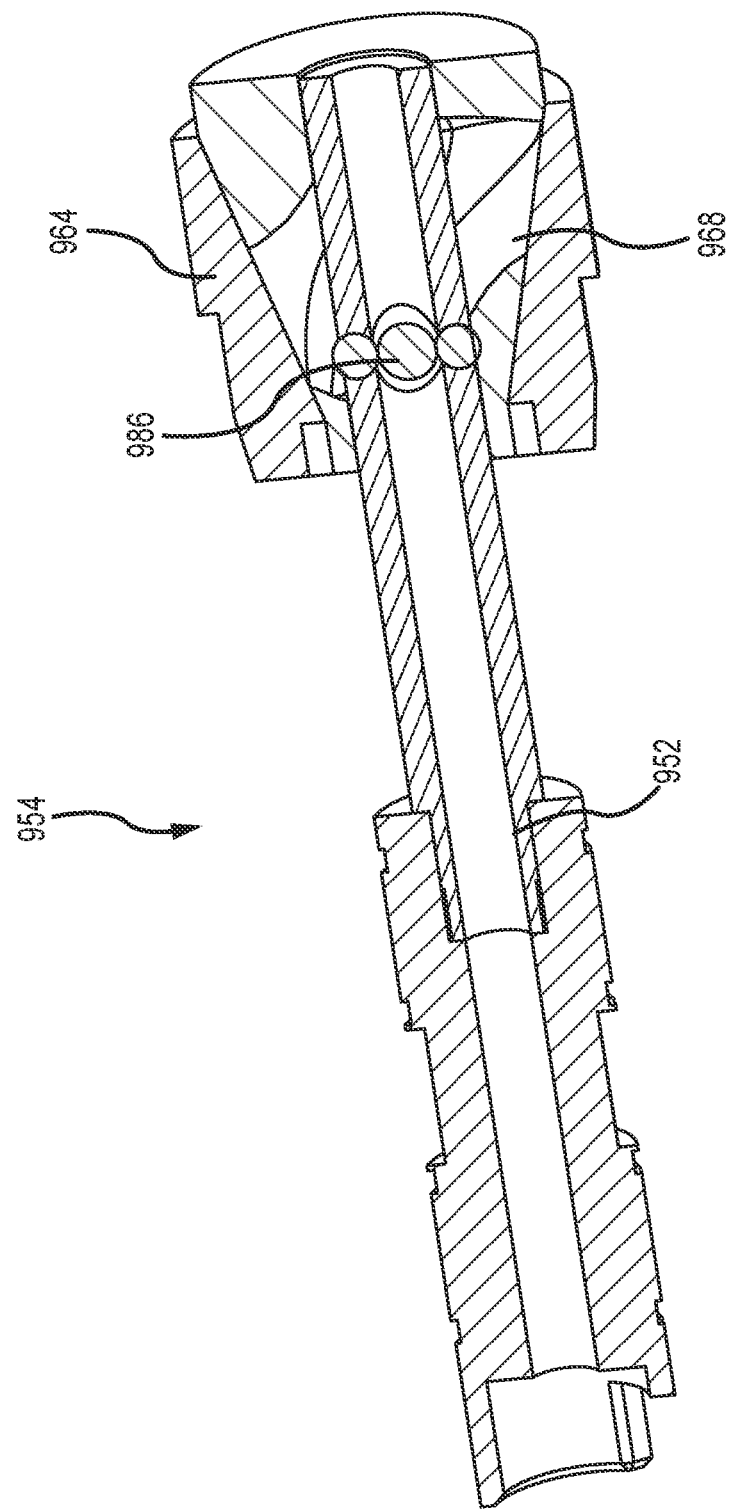
FIG. 60 depicts the orthopedic implant engagement portion of the embodiment of the chuck of FIG. 57 in a cross-sectional view taken along the working axis of the chuck.
Figure 61:
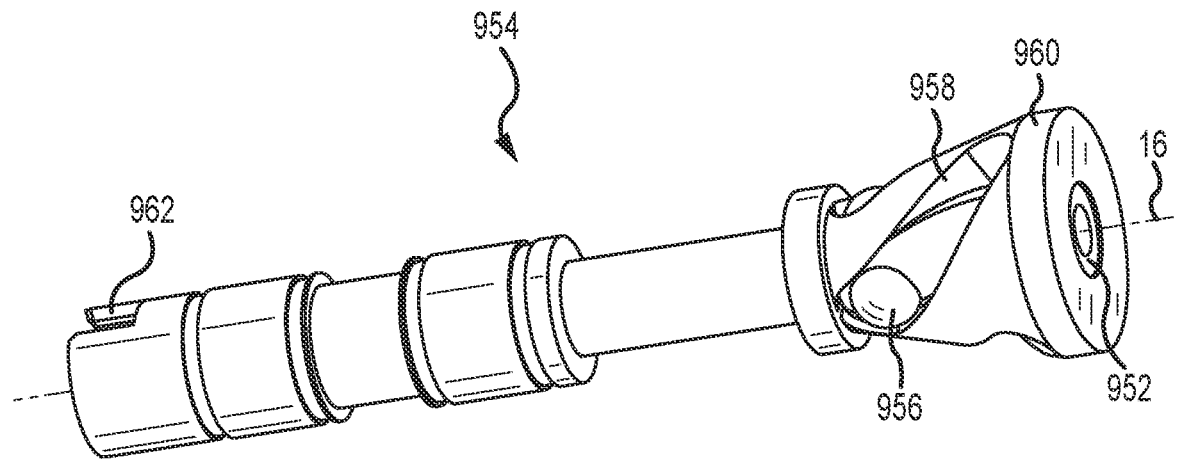
FIGS. 61-62 depicts the orthopedic implant engagement portion of the embodiment of the chuck of FIG. 57 with a ramp member thereof not shown for clarity.
Figure 62:
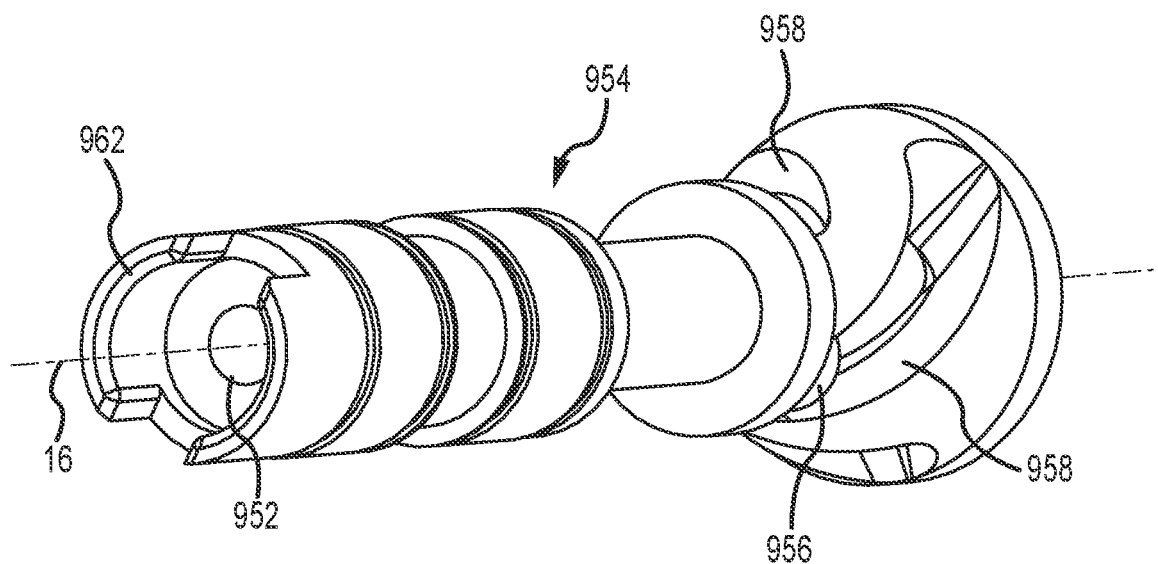
Figure 63:
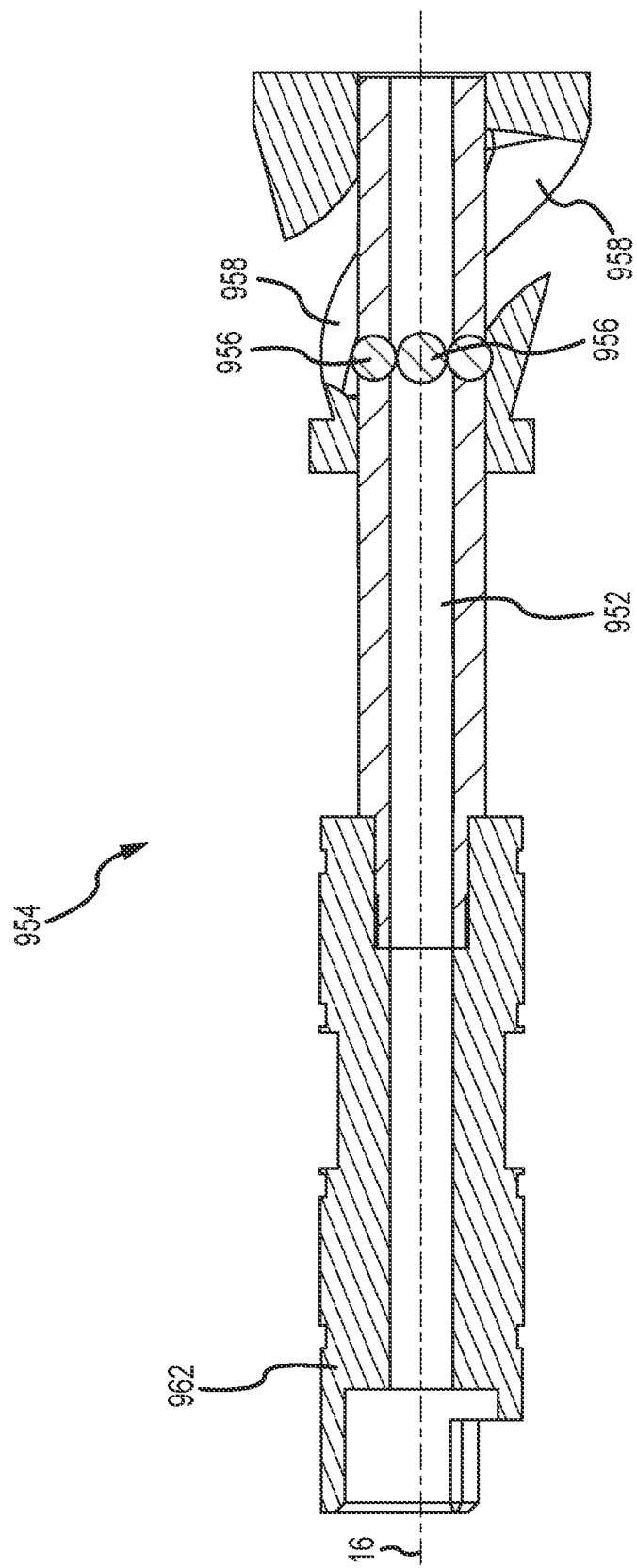
FIG. 63 depicts the orthopedic implant engagement portion of the embodiment of the chuck of FIG. 57 and cross-sectional view taken along the working axis of the chuck.

FIG. 58 depicts a cross-sectional view of the chuck 950 taken along the working axis 16. The chuck 950 may also include an orthopedic engagement portion 954 which is shown in isolation and FIGS. 59-63. The orthopedic implant engagement portion 954 may include a driveshaft 962 that may engage a chuck drive coupling 78 as described above. Accordingly, the instrument 10 may be operative to impart rotational motion to the orthopedic implant engagement portion 954 when the engagement portion 992 is engaged with the instrument.

As can be appreciated in FIGS. 59-63, the orthopedic implant engagement portion 954 may include a plurality of spherical members 956 that are disposed within helical channels 958 of the orthopedic implant engagement portion 954. Specifically, the spherical members 956 may extend into the cannulated passage 952. Accordingly, the spherical members 956 may comprise jaw members for clampingly engaging an orthopedic implant disposed within the cannulated passage 952. The helical channels 958 may be defined in a slide member 960. As may be appreciated, the slide member 960 may move axially relative to the cannulated passage 592. When the slide member 960 is moved proximally, the spherical members 956 may be allowed to move away from the working axis 16. That is, the helical channels 958 may be shaped such that the distal portions thereof allow movement of the spherical members 956 away from the working axis 16. However, when the slide member 960 is moved distally, the spherical members 956 may be moved proximally relative to the helical channels 958, which may constrict such that the spherical members 956 are urged towards the working axis 16.

A cam member 964 having a ramp surface 968 may be provided in position relative to the slide member 960. The cam member 964 may urge the slide member 960 distally under influence of a biasing member 986 as best seen in FIG. 58. Moreover, the helical channels 958 may be arranged such that rotation in a first direction may further urge the spherical members 956 towards a proximal portion of the helical channels 958, thus causing the spherical members 956 to be urged towards the working axis 16. In contrast, rotation in a second direction opposite the first direction may tend to cause the helical channels 958 to urge the slide member 960 proximally against the force imparted by the biasing member 986 such that the spherical members 956 may move distally relative to the helical channels 958, thus allowing the spherical members 956 to move away from the working axis 16.

Accordingly, rotation in the first direction (e.g., a direction tending to induce advancement of an orthopedic implant) may cause the slide member 960 to move distally such that the spherical members 956 are urged towards a proximal portion of the helical channels 958 such that the spherical members 956 are urged toward the working axis 16 to clampingly engage an orthopedic implant disposed within the cannulated passage 952 of the chuck 950. In contrast, counter rotation of the chuck 950 in a direction opposite the first direction may result in the spherical members 956 acting on the helical channels 958 to cause the spherical members 956 to move distally relative to the helical channels 958, thus causing proximal motion of the slide member 960 against the force imparted by the biasing member 986 allowing the spherical members 956 to move away from the working axis 16. That is, rotation of the first direction may cause the spherical members 956 to clampingly engage an orthopedic implant disposed in the cannulated passage 952 and rotation in the second direction may cause the spherical members 956 to release the orthopedic implant.

Figure 64:
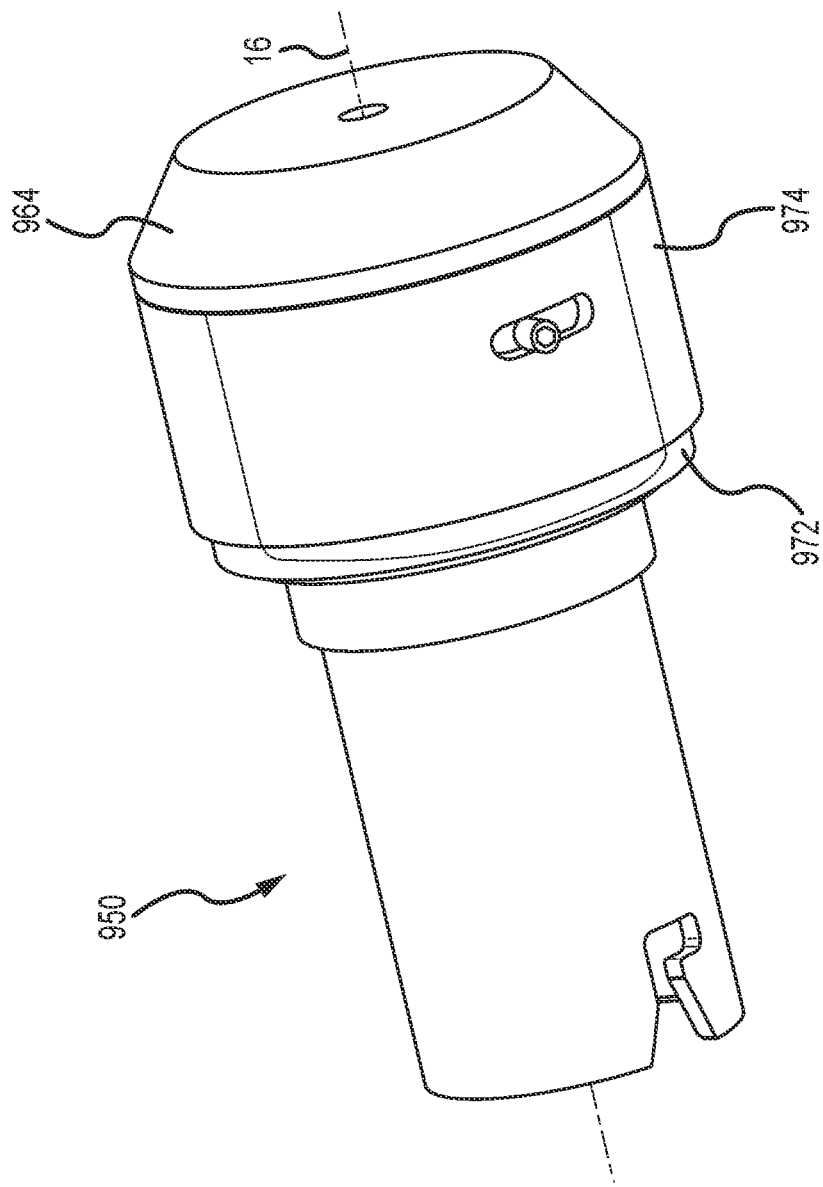
FIGS. 64-66 depict the chuck of FIG. 57 with portions thereof shown in phantom to illustrate utilization of a control ring of the chuck for disposing the chuck between various states of engagement of the orthopedic implant.
Figure 65:
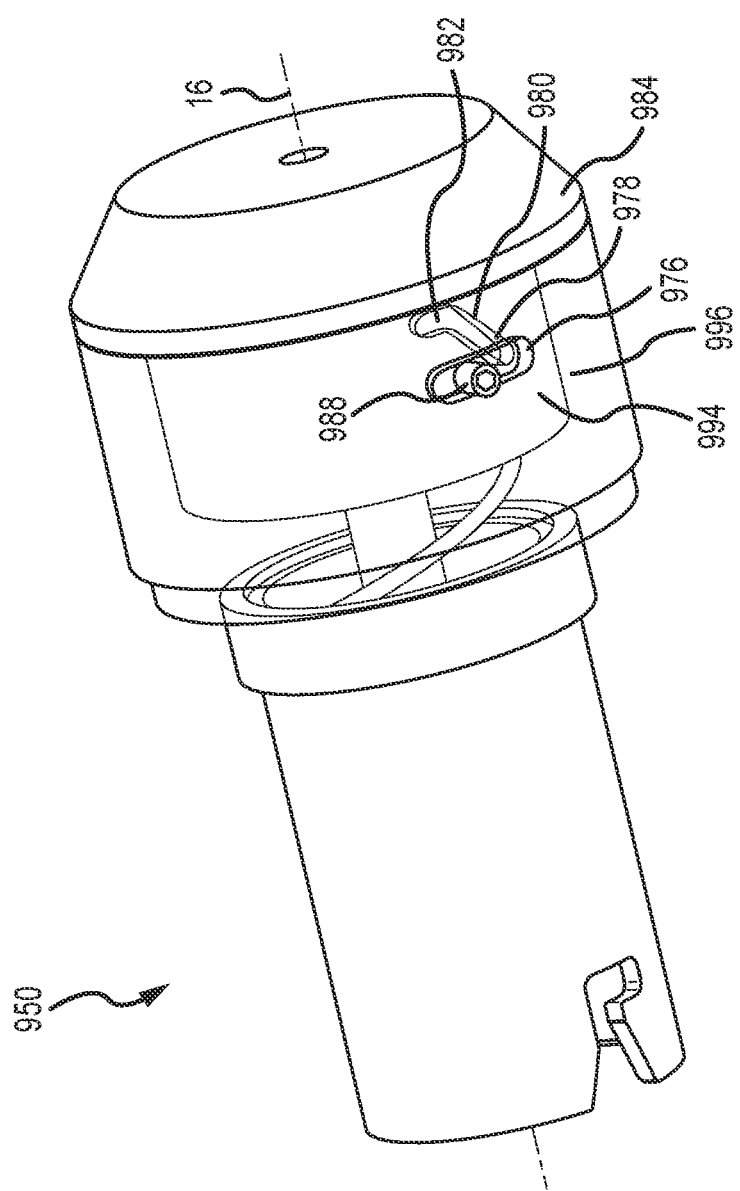
Figure 66:
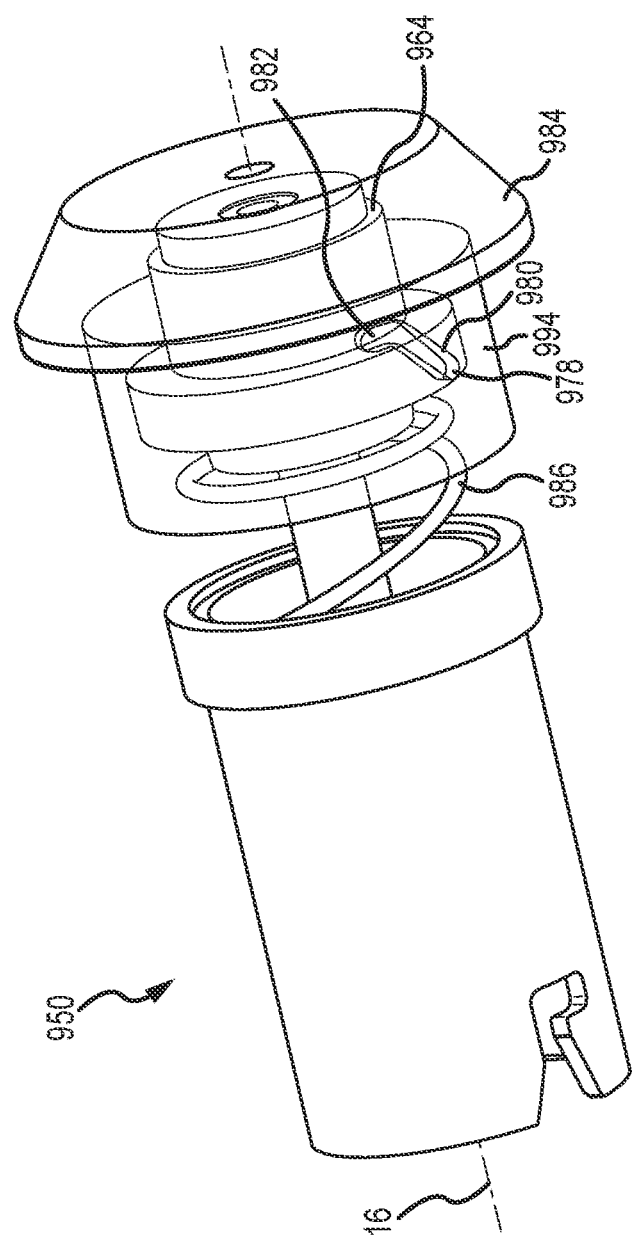

With returned reference to FIG. 58 and with further reference to FIGS. 64-66, the chuck 950 may include features that, like the chuck 550, allow the chuck to be disposed between a biased state, a locked open state, and a lock closed state. The chuck 950 may include a control ring 972 that includes a set screw 988 engaged therewith such that the set screw 988 extends radially towards the working axis 16. Specifically, the set screw 988 may pass through a guide slot 976 and a side wall 996 of the chuck 950. The set screw 988 may also engage a slot 980 disposed in a drive ring 994. The drive ring 994 may be constrainedly engaged with the cam member 964 for co-movement therewith. In turn, when the set screw 988 is disposed in an angled portion 978 of the slot 980, the drive ring 994 may be allowed to move proximally or distally based on the movement of the cam member 964 under the influence described above in relation to rotation of the orthopedic engagement portion 954. That is, when the set screw 988 is disposed in the angled portion 978 of the slot 980, the set screw 988 may be allowed to move within the guide slide 976 such that the drive ring 994 may be moved proximally in distally. The drive ring 994 may be biased to a distal position by the biasing member 986. Thus, the chuck 950 may engage and disengage an orthopedic implant based on induced rotation of the orthopedic implant engagement portion 954 as described above.

However, the chuck 950 may also be disposed in a locked open state. Specifically, the control ring 972 may be rotated such that the set screw 988 engages a flat portion 982 of the slot 980 that extends circumferentially relative to the working axis 16. In this regard, when the set screw 988 is disposed in the flat portion 982 of the slot 980, the drive ring 994 may not be allowed to move axially. As the flat portion 982 may be disposed at a distal end of the slot 980, the drive ring 994 may be locked in a proximal position against the influence of the biasing member 986. In this regard, the cam member 964 may also be moved proximally relative to the slide member 960 such that the spherical members 956 are allowed to move away from the working axis 16 by moving into the distal portions of the helical channels 958. In turn, when the set screw 988 is disposed in the flat portion 982 of the slot 980, the chuck 950 may be in a locked open state such that the spherical members 956 did not engage the orthopedic implant regardless of whether rotated in the first direction and a second rotation.

The chuck 950 may also be disposed in a lock closed state. The control ring 972 may have a threaded lock ring 974 in threaded engagement with the control ring 972. In this regard, when the set screw 988 is disposed in the angled portion 978 of the slot 980 and the spherical members 956 are disposed in clamping engagement with the orthopedic implant in the cannulated passage 952, the lock ring 974 may be advanced distally relative to the control ring 972 until the lock ring 974 abuts the end 984. In turn, the lock ring 974 may be tightened against the endcap 984 by further distal advancement of the lock ring 974 relative to the control ring 972 by threaded engagement therebetween. In turn, the control ring 972 may be prevented from undergoing further rotation such that the set screw 988 may be disposed in a set position and the angled portion 978 such that the cam member 964 is locked in a distal position, thus causing the spherical members 956 to be maintained in a position towards the working axis 16 such that the orthopedic implant is engaged regardless of the direction of rotation of the chuck 950.

The foregoing embodiments of chucks may be utilized to engage traditional orthopedic implants (e.g., smooth walled implants). Accordingly, these chuck embodiments may, in at least some applications, be utilized during traditional operations where the measurement system 40 of the instrument 10 may not be utilized. As such, the components of the measurement system 40 (e.g., the displacement sensing on 44 and particularly the distal portion 46 of the displacement sensing arm 44) may not be utilized. In one embodiment, the structure of the displacement sensing arm 44 described above allows the distal portion 46 to be maintained in a stowed, proximal position relative to the orthopedic implant 62. That is, the detent 74 on the displacement sensing arm 44 may be engaged by the stop 70 such that the displacement sensing arm 44 is retained in the proximal, stowed position. This may be utilized to maintain the displacement sensing on 44 in a position that reduces interference of the components of the measurement system 40 with traditional implant placement operations.

Figure 16:
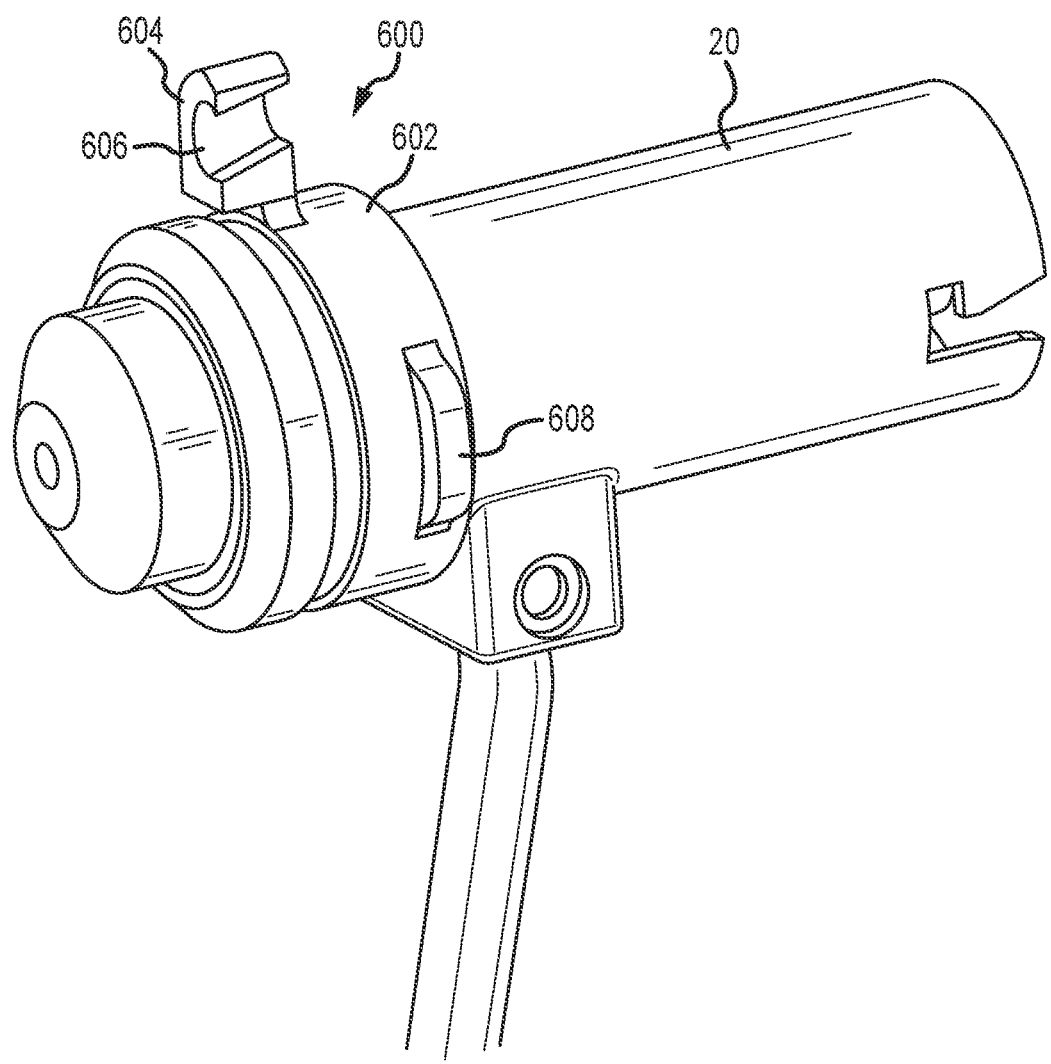
FIG. 16 depicts an embodiment of a chuck with a displacement sensing arm retention member for retaining a displacement sensing arm of an instrument with which the chuck is engaged where the displacement sending arm retention member is in an engaged position.
Figure 17:
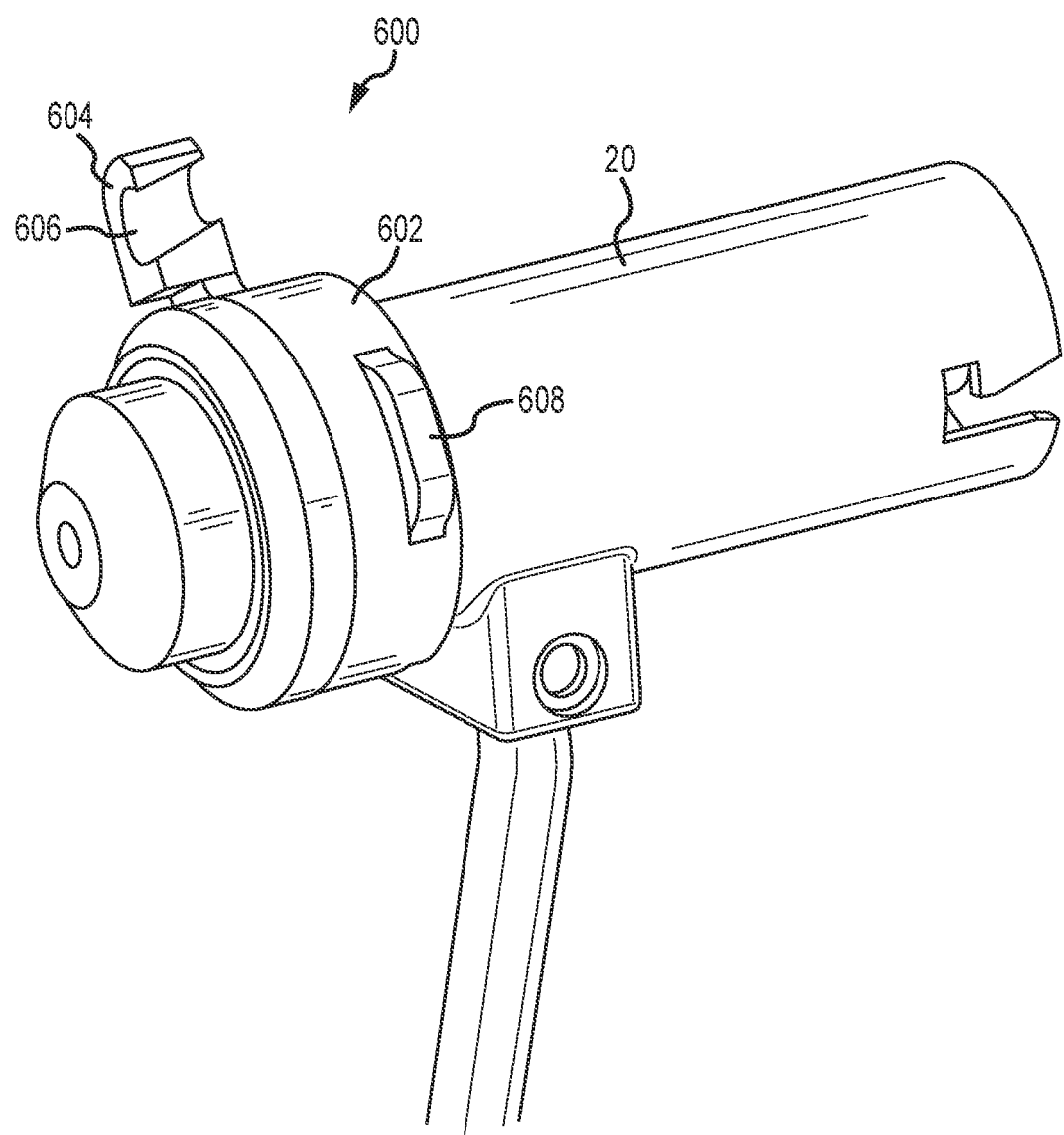
FIG. 17 depicts an embodiment of a chuck with a displacement sensing arm retention member for retaining a displacement sensing arm of an instrument with which the chuck is engaged where the displacement sending arm retention member is in a disengaged position.

FIGS. 16 and 17 depict another embodiment of a mechanism for maintaining the displacement sensing arm 44 in a stowed position relative to the orthopedic implant engaged by the chuck 20 when the placement sensing on 44 is not utilized. The embodiment described in FIGS. 16 and 17 may be utilized in place of or in addition to the structure of the displacement sensing arm 44 described above for maintaining the displacement sensing on 44 and a proximately biased position. FIGS. 16 and 17 depict an embodiment of a displacement sensing arm retention member 600. The retention member 600 may include a clasp 604 adapted to engage the displacement sensing arm 44 of the instrument 10. Specifically, the clasp 604 may include a contoured pocket 606. The contoured pocket 606 may be shaped to accommodate the distal portion 46 of the displacement sensing arm 44. Specifically, the contoured pocket 606 may be shaped to accommodate the portion of the distal portion 46 of the displacement sensing arm 44 that is aligned with the clasp 604 when the displacement sensing arm 44 is arranged in a proximal, stowed position such as that shown in FIG. 1.

The clasp 604 may be displaceable relative to the displacement sensing arm 44 so as to allow the clasp 604 to be moved to allow the displacement sensing arm 44 to move while displacement sensing on 44 is placed into the proximal, stowed position shown in FIG. 1. Once the displacement sensing arm 44 is in place, the clasp 604 may be moved to engage the displacement sensing arm 44 such that the contoured pocket 606 is provided about at least a portion of the distal portion 46 of displacement sensing arm 44. The engagement of the displacement sensing arm 44 by the contoured pocket 606 may limit the distal movement of the displacement sensing arm 44 such that the displacement sensing arm 44 is maintained in the proximal position.

The clasp 604 may be mounted on a ring 602 that extends about the chuck 20. In this regard, the ring 602 may be rotated about the working axis 16 so as to move the clasp 604 between the engaged position shown in FIG. 16 and the disengaged position shown in FIG. 17. The ring 602 may also include a lug 608 to help assist manipulation of the ring 602 to move the clasp 604 between the engaged position and the disengaged position. As such, the retention member 600 may be utilized to maintain the displacement sensing arm 44 in the proximal, stowed position shown in FIG. 1 was to reduce interference of the displacement sensing arm 44 with the orthopedic implant 62 when the instrument 10 is utilized. While the retention member is shown in relation to the embodiment of the chuck 200 having a lever arm 204, it may be appreciated that the retention member may be provided with any of the other chuck embodiments described above or other chuck embodiments without limitation.

There may also be times in which an orthopedic implant may be disposed in a chuck, but not engaged by locking rollers, cam blocks, or other jaw structures of a chuck. However, the surgeon may want the orthopedic implant to remain in its place relative to a chuck absent movement of the orthopedic implant manually by the surgeon. For example, prior to engagement of the orthopedic implant by the jaws of the chuck, the surgeon may place the orthopedic implant in the cannulated passage in a specific position. The surgeon may then move the surgical instrument without engaging an actuation lever or otherwise closing a jaw structure of a chuck. When the surgeon then actuates the actuation lever, it is desirable that the orthopedic implant be in the original position that the orthopedic implant was placed in.

Figure 45:
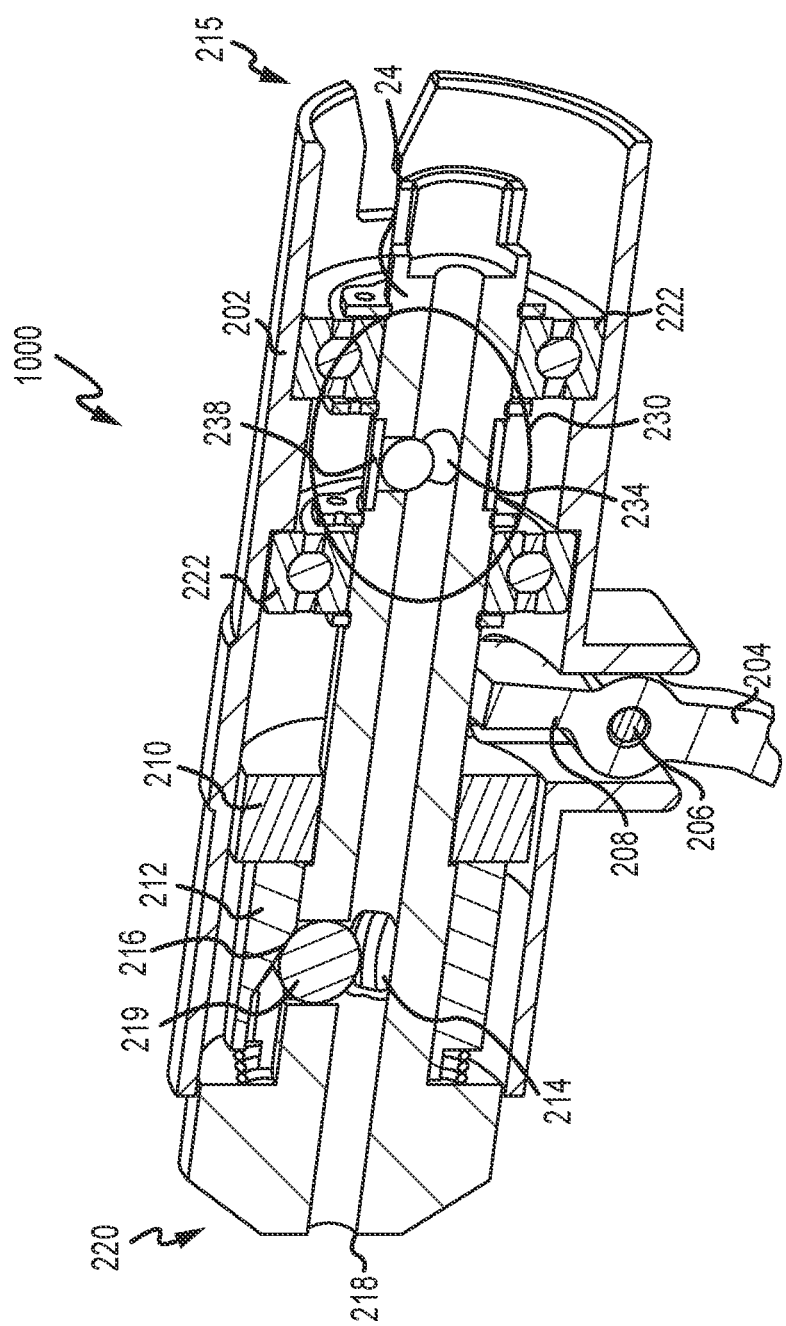
FIG. 45 depicts an embodiment of a chuck in cross section along the working axis thereof that includes an implant holder utilized to maintain the position of the orthopedic implant and a second cannulated passage of the chuck even when the chuck jaws are not engaged with the orthopedic implant.
Figure 46:
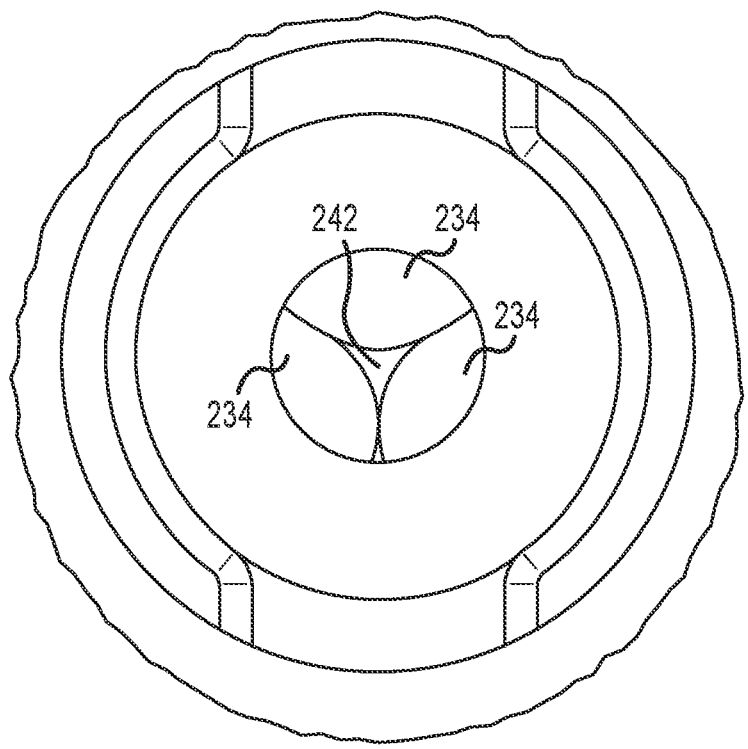
FIG. 46 depicts the implant holder of the embodiment of the chuck of FIG. 45 in cross section perpendicular to a working axis of the chuck.

As such, FIGS. 45 and 46 depict another embodiment of a chuck 1000. The chuck 1000 may include features that facilitate holding an orthopedic implant 62 even when a chuck jaw member (i.e., locking roller 214) is disengaged from the orthopedic implant 62. In this regard, a force by the surgeon that is manually applied to the orthopedic implant 62 to move the orthopedic implant 62 along or about the axis may be facilitated by, but absent an external force by the user, the orthopedic implant 62 remains stationary. For instance, the force of gravity may not cause the orthopedic implant 62 to slide in the cannulated passage 218. As such, the chuck 1000 may include an implant holder 230 for retaining the orthopedic implant 62 without requiring any force by the user. Upon placement of the orthopedic implant 62 inside the cannulated passage 218, the implant holder 230 may retain the orthopedic implant 62 to help prevent axial or rotational movement of the orthopedic implant 62 relative to the chuck 1000 during use when not engaged by the actuation lever 204 of the chuck or otherwise closing the locking rollers 214. In one configuration, at least one gripper 234 (e.g., ball bearings, rollers, etc.) may be biased toward the center of the cannulated passage 218 by a spring 238 (e.g., a constant force spring). When the orthopedic implant 62 is inserted into the cannulated passage 218 and contacts the grippers 234, the grippers 234 overcome the spring 238 bias and are radially displaced away from the working axis 16. When the grippers 234 are displaced, the spring 238 maintains its bias on the grippers 234 and the grippers 234 on the orthopedic implant 62.

It can be appreciated that use of ball bearing as grippers 234 allows for axial translation or rotation of the orthopedic implant 62 in relation to the chuck 1000. Ball bearings allow for the coefficient of friction to be relatively easy to overcome yet still is high enough to retain the orthopedic implant 62 in place when external forces are not applied. The force required by the surgeon to rotate or slide the orthopedic implant 62 about or along the axis may be equal. Alternatively, rollers may be used as grippers 234. Use of rollers as grippers 234 allows for ease of movement upon application of an external force by a surgeon in one direction, however, it may require more force to move the orthopedic implant 62 in an another direction. For example, if rollers are oriented in a chuck such that the axis which the rollers rotate about is perpendicular to the axis of the cannulated passage 218, the force required to move the orthopedic implant 62 axially may be less than that required to rotate the orthopedic implant 62. Alternatively, if the axis of rotation of the rollers is oriented parallel to the cannulated passage 218 then the force required to move the orthopedic implant 62 along the axis of the cannulated passage 218 may be higher than the force required to rotate the orthopedic implant 62.

FIG. 46 depicts a cross-section of the implant holder 230 in the normally closed position. When the orthopedic implant 62 is inserted into the cannulated passage 218, the diameter of the orthopedic implant 62 may be greater than spacing 242 created by the shape of the grippers 234. If ball bearing type grippers 234 are used the diameter of the ball bearings may be adjusted to accommodate a narrower orthopedic implant 62. Additionally, the implant holder 230 may retain any diameter orthopedic implant 62 up to the diameter of the cannulated passage 218.

In this regard, it can be appreciated that though the implant holder 230 is only shown in FIGS. 45 & 46, it may be implemented in any of the chucks discussed herein (including those used with traditional smooth walled implants and indexed implants discussed below). Furthermore, though the implant holder 230 shown in FIGS. 45 & 46 includes a spring 238 biasing grippers 234 toward the working axis 16, any device for retaining the orthopedic implant 62 which allows motion upon application of external force is suitable. Further, an elastic strip or collar may be used instead of a spring to bias the grippers 234 toward the working axis.

As briefly described above, use of the measurement system 40 to place an orthopedic implant may result in a number of benefits. Namely, a user may not be required to guess or rely on "feel" alone in placement of the implant. Rather, the measurement system may allow for selection of various modes to allow for different placements of the orthopedic implant such that the position of the implant is automatically determined based on the sensors of the measurement system 40. This may allow the implant to be placed more reliably and more efficiently. As such, the complexity, risk, cost, and time of operations may be reduced.

While some of the foregoing embodiments allow for engagement of an orthopedic implant without requiring application of an external force to the chuck, other embodiments may be provided that may also assist in reducing the potential for slippage between the implant and the chuck so as to accurately measure a displacement of the instrument and/or and accurate force measure.

In turn, an embodiment of an orthopedic implant is provided herein that may include a plurality of indexing features disposed along at least a portion of the length of the orthopedic implant relative to the working axis 16. In this regard, a corresponding chuck 20 may be provided to engage one or more of the plurality of indexing features of the orthopedic implant. In turn, the orthopedic implant may be engaged without an external force acting on the chuck such that the orthopedic implant is maintained stationary along the working axis. Also, the chuck described herein may provide for efficient engagement and disengagement of the orthopedic implant for efficient operation of the chuck. For instance, the chuck may be manipulated by a single hand of the user for engagement and disengagement of the orthopedic implant.

Figure 18:
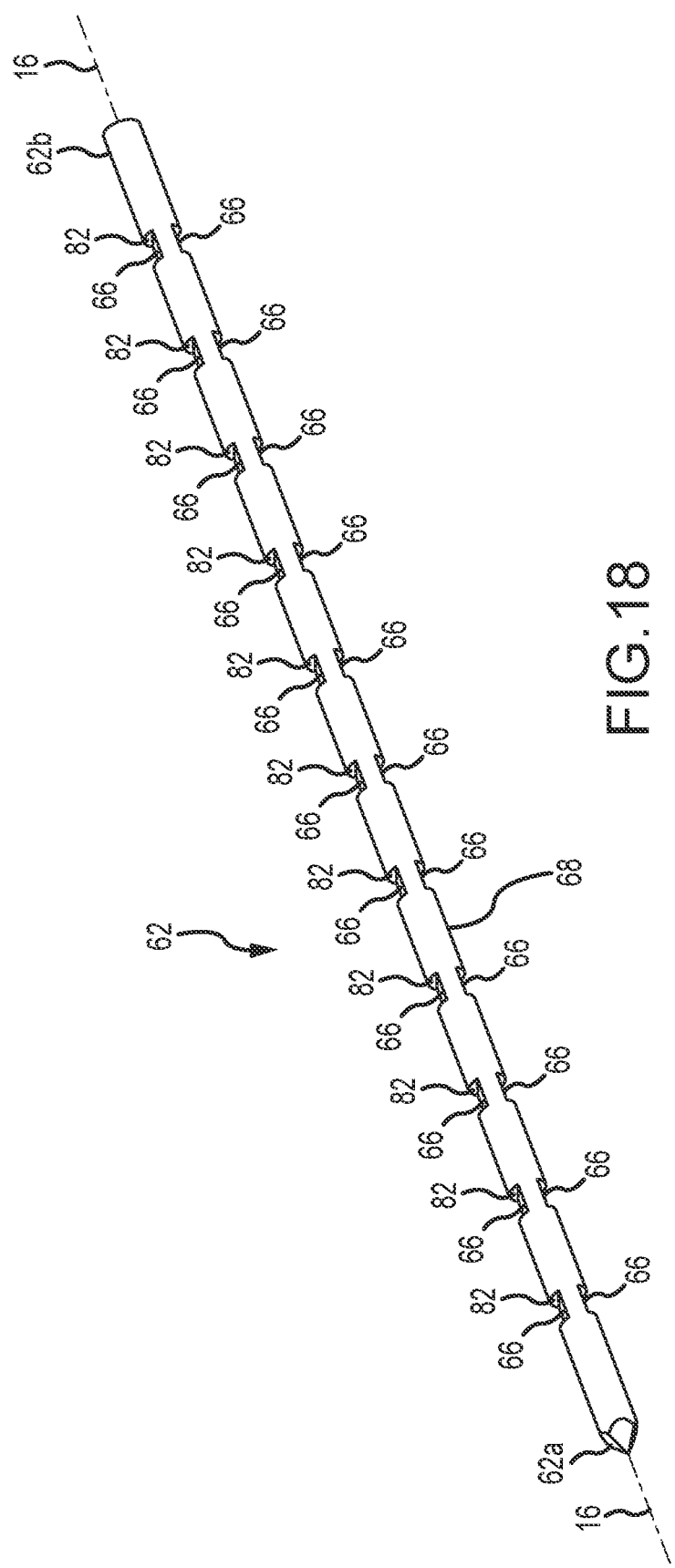
FIG. 18 depicts an embodiment of an orthopedic implant having indexing features.

With further reference to FIG. 18, one embodiment of an orthopedic implant 62 comprising a plurality of indexing features 66 is shown. The indexing feature 66 may comprise a notch or indentation on the exterior surface of the orthopedic implant 62. The orthopedic implant 62 may include a distal portion 62a that is advanced into the bone of the patient and a proximal portion 62b disposed on a side of the orthopedic implant 62 opposite the proximal portion 62a. In at least some embodiments, the proximal portion 62a and the distal portion 62b may be identical such that either end may comprise a feature to allow for advancement of the implant into the bone of a patient. For instance, either or both ends may include a sharpened end, a threaded portion, flutes or other feature that assists in advancement of the proximal portion 62a into the bone of the patient. The orthopedic implant 62 may include a cylindrical body member 68 extending between the proximal portion 62a and the distal portion 62B. In this regard, the indexing feature 66 may include an inset engagement surface 82 that is inset relative to the cylindrical body 68. For instance, the surface 82 may extend along a cord length relative to the circular cross-section of the cylindrical body 68. In an embodiment shown in FIG. 18, the indexing features 66 may include corresponding opposing surfaces 82 that are coextensive relative to a length extending along the working axis 16. That is, the indexing features 66 may include offset notches with opposing engagement surfaces 82 that occupy the same length along the working axis 16.

Figure 19:
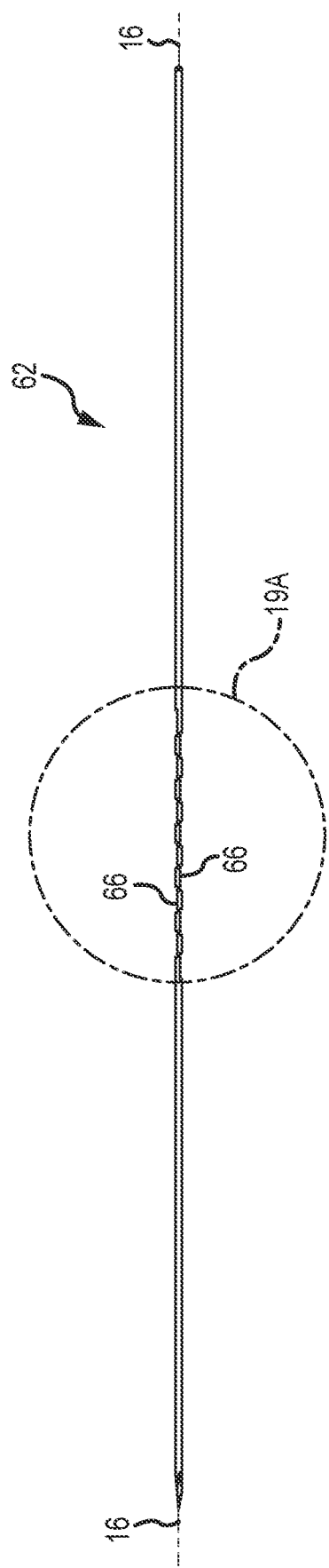
FIG. 19 depicts an embodiment of an orthopedic implant having indexing features.
Figure 19A:
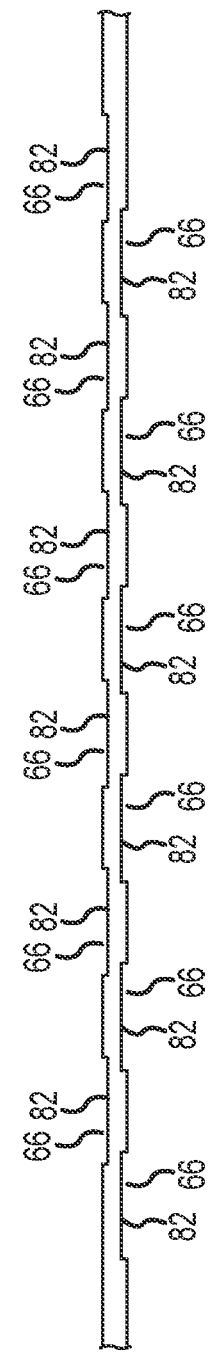
FIG. 19A depicts a detail of the embodiment of the orthopedic implant of FIG. 19.

In contrast, FIG. 19 and FIG. 19A (which provides a detailed view of the engagement features 66 of the embodiment depicted in FIG. 19) depict an alternative embodiment of an orthopedic implant 62 whereby the indexing features 66 may comprise offset opposing engagement surfaces 82 that are offset relative to a length corresponding to the working axis 16. That is, each given engagement surface 82 corresponding to the inset portion of the indexing feature 66 may be disposed between adjacent engagement surfaces 82 provided on an opposite portion of the implant 62 (e.g., opposite meaning disposed roughly 180° about the working axis 16). In this regard, the indexing member 66 comprise staggered offset opposing engagement surfaces 82 where adjacent opposing engagement surfaces 82 are staggered along a length corresponding to the working axis 16. With further reference to FIG. 20, another embodiment is shown whereby the opposing engagement surfaces 82 may be alternating such that no portion of the opposing engagement surfaces 82 overlap in a length corresponding to the working axis 16.

Figure 21:
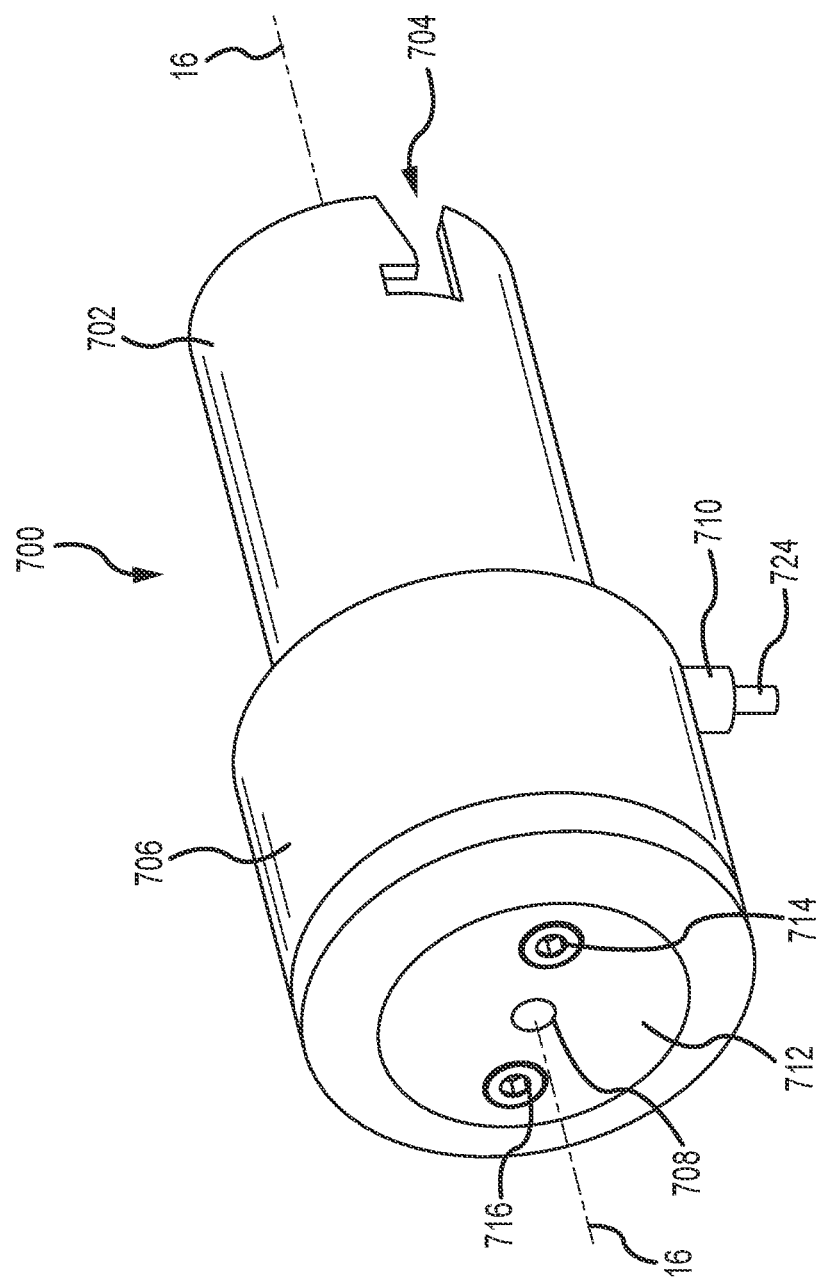
FIG. 21 depicts an embodiment of a chuck adapted for engagement of an orthopedic implant having indexing features.

With further reference to FIG. 21, an embodiment of a chuck 700 is depicted that may be used to selectively engage an orthopedic implant 62 having a plurality of indexing features as described above. The use of a chuck 700 that engages an indexed orthopedic implant may provide the ability to utilize the measurement system 40 of the instrument 10 such that no external forces are required to engage the implant, yet the implant is securely engaged and easily engaged/disengaged.

Specifically, the instrument 10 may include a force sensor 50 capable of outputting a signal indicative of the force acting axially on the leading edge 10a of the orthopedic implant 62 as it is advanced through the bone of the patient. The force sensor 50 may be disposed proximally relative to the drive system 30. In this regard, the drive system 30, chuck 20, and engaged implant 62 may be axially rigid such that a force acting on the leading edge 10a of the orthopedic implant 62 may cause the force to be transmitted through the implant 62, chuck 20, and drive system 30 to act on the force sensor 50. As addressed above, relying on external forces to engage the implant 62 may result in inaccuracies of the measurement system 40.

However, the coordination of the chuck 700 with an orthopedic implant such as those described above having a plurality of index features 66 may allow for the orthopedic implant 62 to be axially fixed relative to the chuck 20 allow for free transmission of force from the orthopedic implant 62 to the chuck 20 and to the drive system 30 for accurate measurement at the force sensor 50 without inducement of additional or different forces resulting from the engagement of the orthopedic implant 62 by the chuck 20.

With further reference to the chuck 700 depicted in FIG. 21-30, the chuck 700 may include a chuck body 702. The chuck body 702 may comprise an engagement portion 704 at the proximal end of the chuck 700 that, as described above, may be used to interface with the instrument 10. The chuck 700 may also include an engagement control member 706. A cannulated passage 708 may be provided into which an orthopedic implant 62 may be provided as shown in various ones of FIGS. 21-30. As we discussed in greater detail below, the engagement control number 706 may correspond to a control ring that is rotatable relative to the chuck body 702 to control engagement and disengagement of the orthopedic implant 62. In this regard, the chuck 700 may also include a button 710 may be depressed to allow for immobilization of a chuck drive shaft to allow for relative movement between the engagement control number 706 and a chuck drive shaft described in greater detail below.

Figure 22:
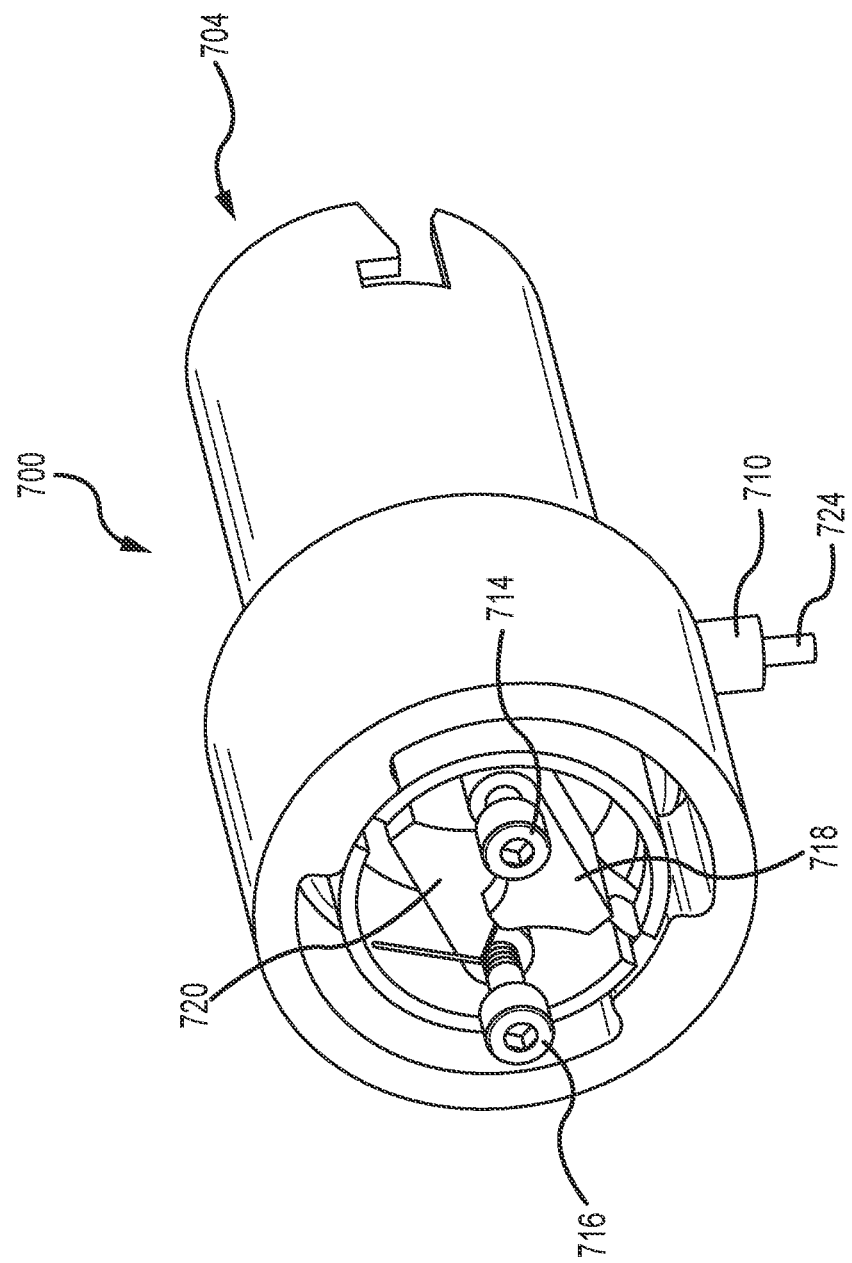
FIG. 22 depicts the embodiment of the chuck of FIG. 21 with a distal plate thereof removed for purposes of illustration of jaw members disposed therein.
Figure 23:
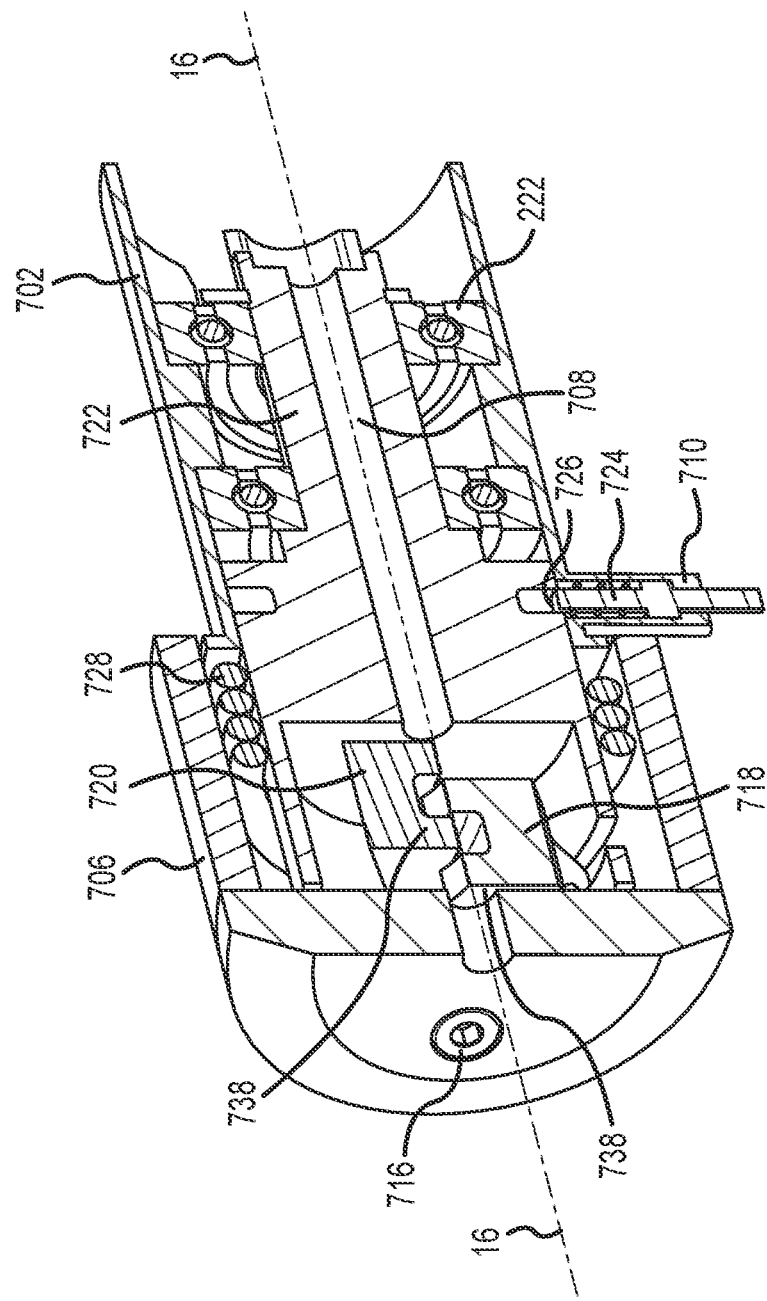
FIG. 23 depicts the embodiment of the chuck of FIG. 21 in cross section along a working axis of the chuck.

The chuck 700 may include a distal plate 712. The distal place 712 may be secured to a chuck drive shaft 722. For instance, the distal plate 712 may be bolted to the chuck drive shaft 722 by pivot members 714 and 716. For instance, the pivot members 714 and 716 may comprise threaded portions engaged with the chuck drive shaft 722. With further reference to FIG. 22 where the distal plate 712 has been removed for illustration purposes, the pivot members 714 and 716 may include bearing surfaces (i.e., non threaded portions) that may support a first jaw member 718 and a second jaw member 720, respectively. The first jaw member 718 may be disposed for relative movement about a first axis defined by pivot member 714. The second jaw member 720 may be disposed for relative movement about a second axis defined by the pivot member 716. As may be appreciated in FIG. 23, the first jaw member 718 and second jaw member 720 may be disposed relative to the cannulated passage 708 such that the jaw members 718 and 720 may be moved radially toward and away from the working axis 16 to engage the orthopedic implant 62.

The chuck driveshaft 722 may engage with the chuck drive coupling 78 of the instrument 10. In this regard, upon operation of the drive system 30, the chuck driveshaft 722 may be rotated. As described above, the pivot member 714 and 716 may be engaged with the chuck driveshaft 722. As such, upon rotation of the chuck drive shaft 722, the pivot members 714 and 716 may also be rotated as are the first jaw member 718 and second jaw member 720 supported by the pivot members 714 and 716, respectively. In turn, when the jaw members 718 and 720 are engaged with an orthopedic implant 62, rotational motion is also imparted to the orthopedic implant 62.

The button 710 may include a displaceable rod 724. A corresponding pocket 726 may be provided on the chuck driveshaft 722. In this regard, the pocket 726 may be aligned with the button 710 such that when the button 710 is displaced, the rod 724 may extend into the pocket 726. This may rotationally lock the chuck driveshaft 722 relative to the chuck body 702. In turn, the engagement control member 706 may be rotated relative to the chuck drive shaft 722. The engagement control member 706 may be biased by a biasing member 728. The biasing member 728 may bias the engagement control member 706 into a position that also biases the first jaw member 718 and the second jaw member 720 toward the working axis 16.

Figure 28:
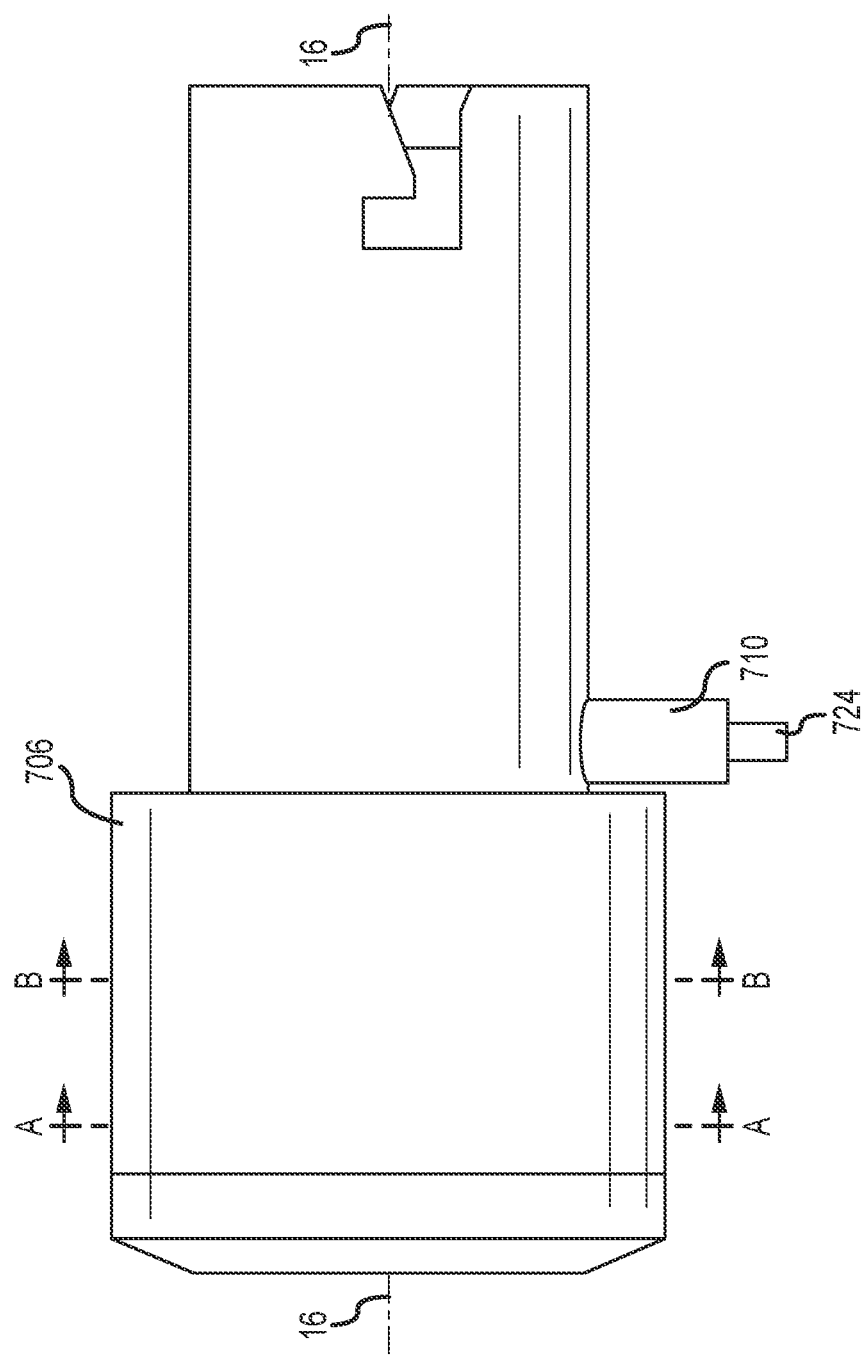
FIG. 28 depicts a side view of the embodiment of the chuck of FIG. 21.
Figure 29:
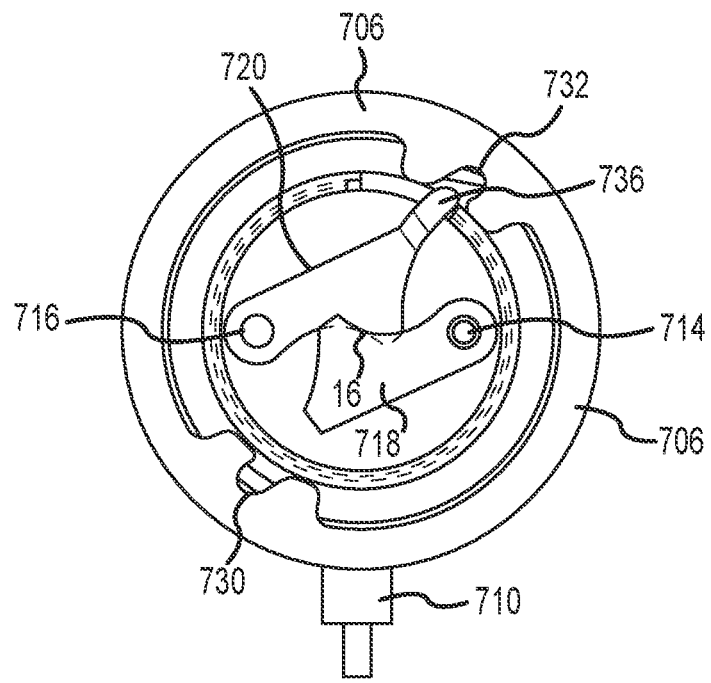
FIG. 29 depicts a front view of the embodiment of FIG. 21 in cross section along line A-A of FIG. 28.
Figure 30:
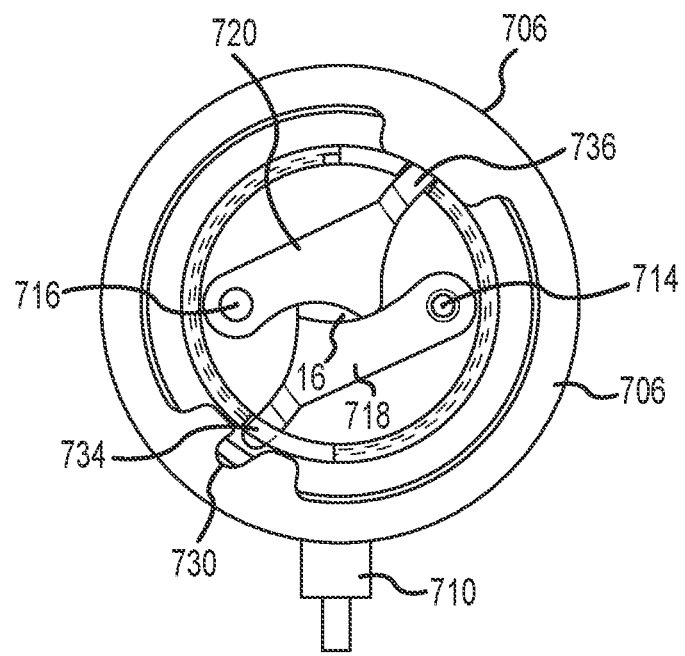
FIG. 30 depicts a front view of the embodiment of FIG. 21 in cross section along line B-B of FIG. 28.
Figure 31:
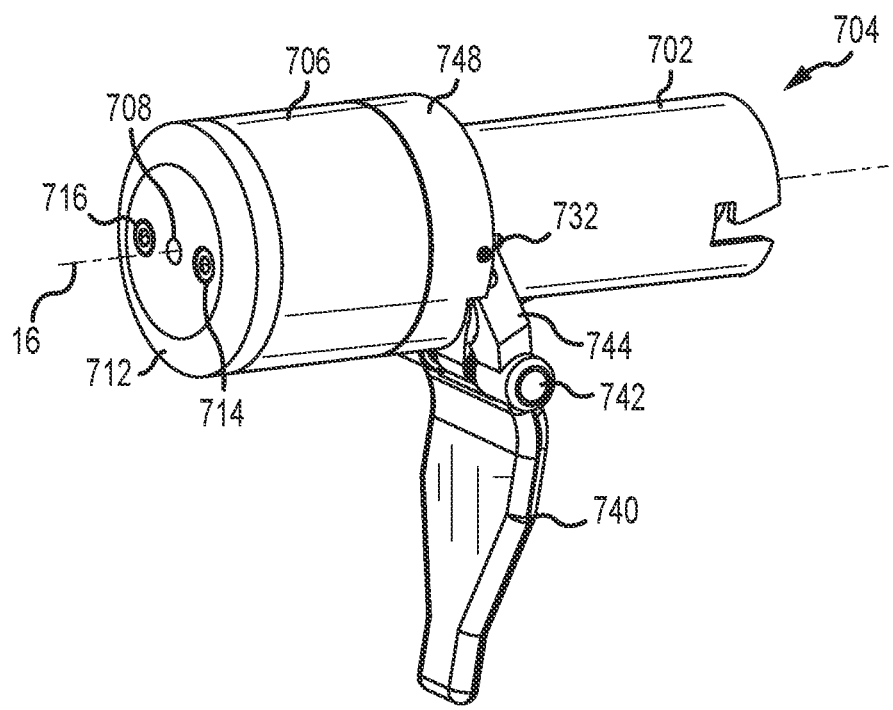
FIG. 31 depicts an embodiment of a chuck adapted for engagement of an orthopedic implant having indexing features.
Figure 32:
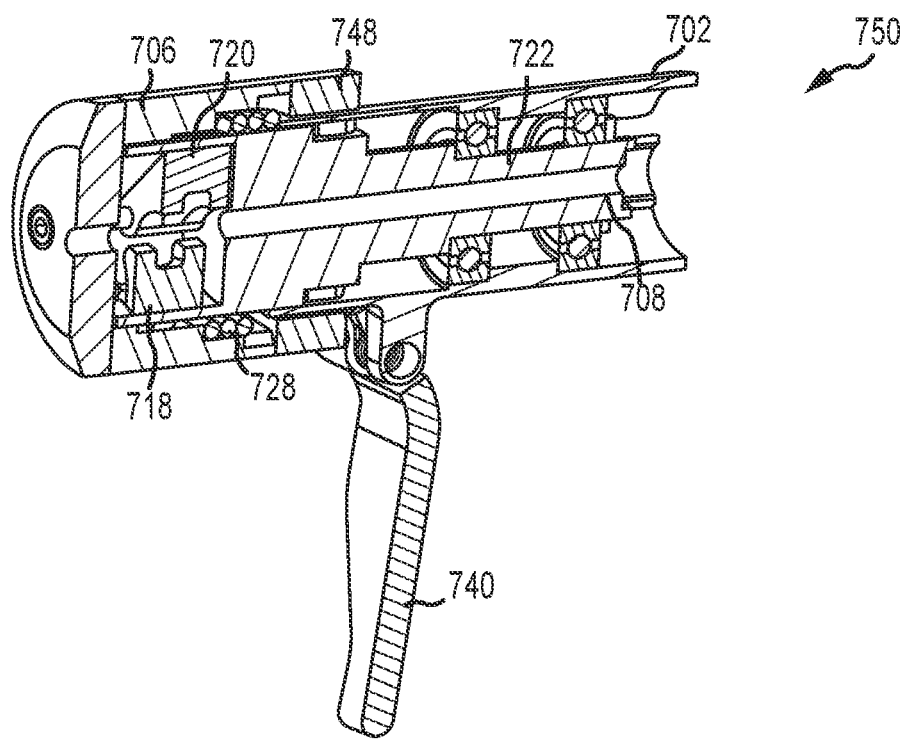
FIG. 32 depicts the embodiment of the chuck of FIG. 31 in cross section along a working axis thereof.
Figure 33:
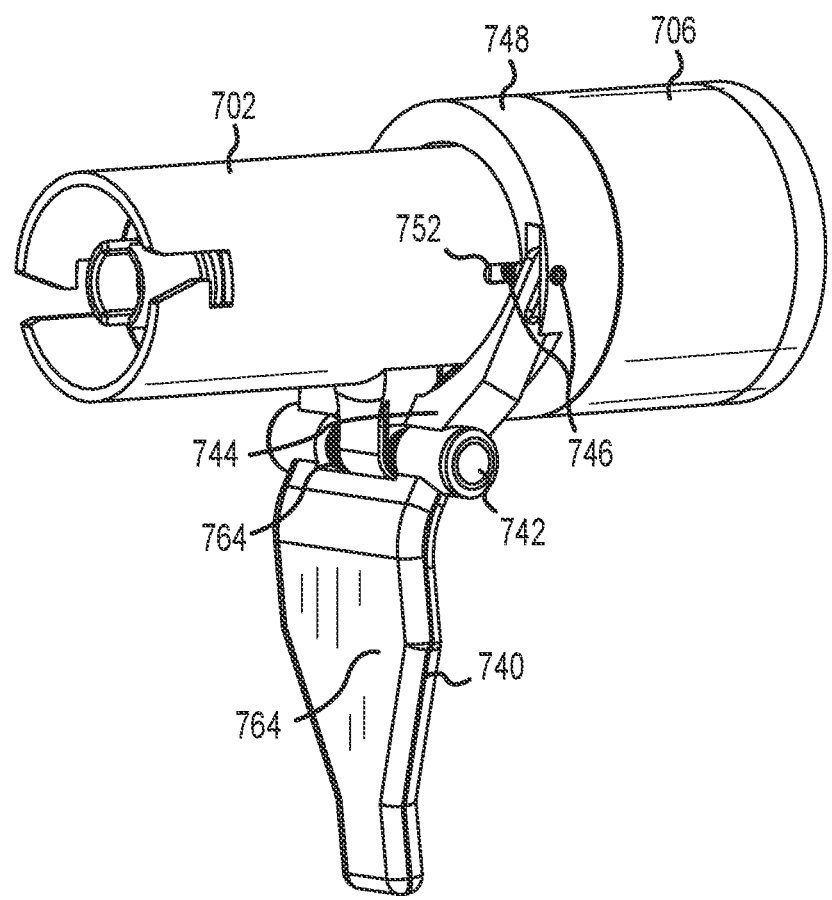
FIG. 33 depicts a rear perspective view of the embodiment of the chuck of FIG. 31.

With further reference to FIGS. 28, 29, and 30, the engagement control member 706 is shown relative to the first jaw member 718 and the second jaw member 720 at two locations along the working axis 16. The first jaw member 718 may include a first follower portion 734 disposed relative to a first cam surface 730 of the engagement control member 706. That is, the engagement control member 706 may define a first cam surface 730 with which the first follower portion 734 is engaged. The second jaw member 720 may include a second follower portion 736 arranged relative to a second cam surface 732 defined by the engagement control member 706. Accordingly, upon rotation of the engagement control member 706, (e.g., against the biasing force induced by the biasing member 728), the first cam surface 730 and the second cam surface 732 may be moved relative to the first and second jaw members 718 and 720 such that the first follower portion 732 and the second follower portion 734 are engaged by the respective cam surface 734 or 746. Upon rotation of the engagement control member 706, the first follower portion 734 and the second follower portion 736 may be engaged so as to induce rotation of the first jaw member 718 about the first pivot member 714 and the second jaw member 716 about the second pivot member 716. As the respective follower portion 734 or 736 is disposed opposite the corresponding pivot member 714 or 716, rotation of the engagement control member 706 may act on each respective jaw member 718 or 720 to lever the jaw member 718 or 720 away from the working axis 16. This pivotal motion of the jaw members 718 and 720 relative to the pivot members 714 and 716 may result in the jaw members being radially moved away from the working axis 16.

Figure 24:
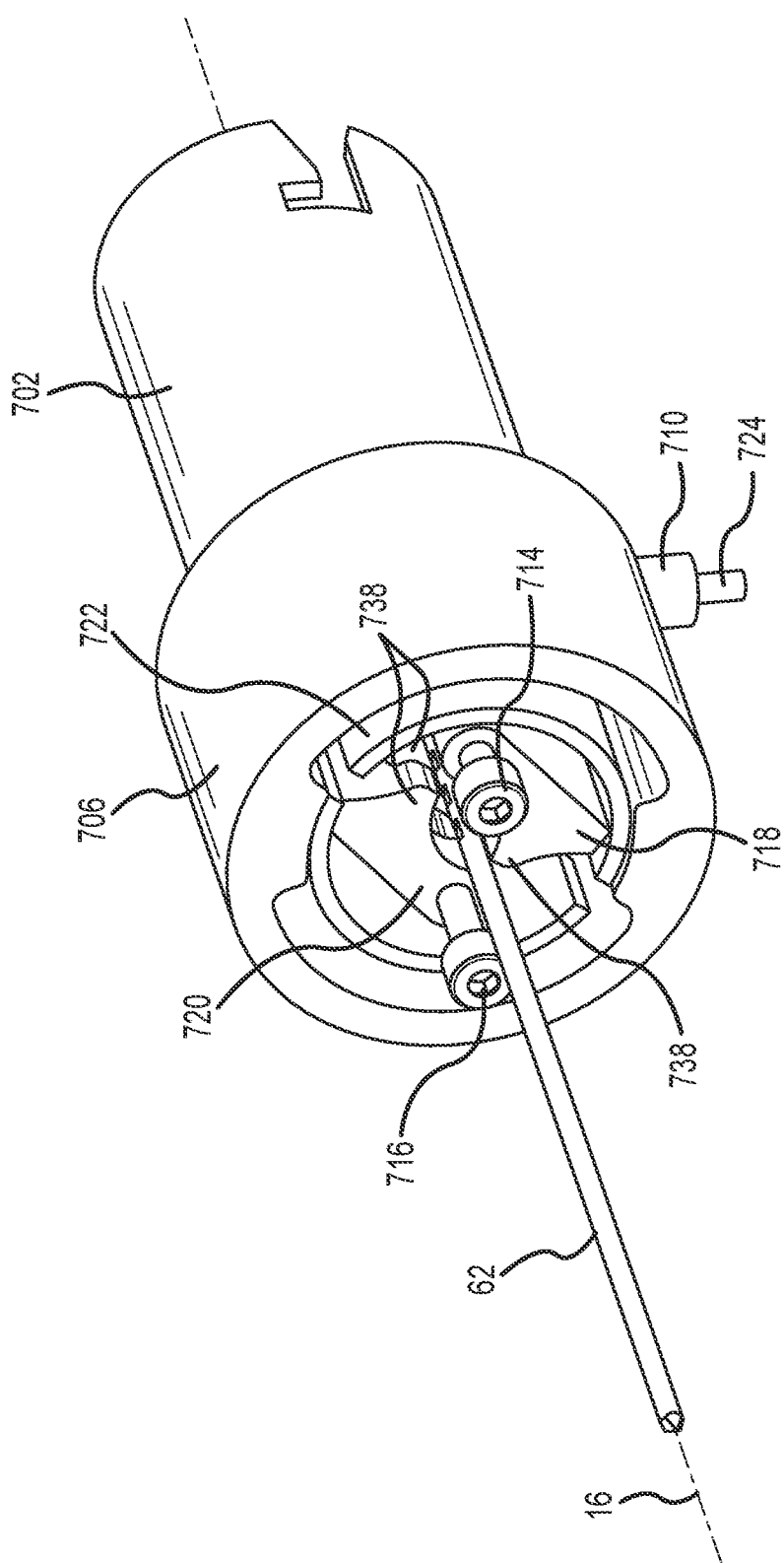
FIG. 24 depicts the embodiment of the chuck of FIG. 21 with a distal plate thereof removed to show positioning of the orthopedic implant relative to the chuck for purposes of illustration of jaw members disposed therein.
Figure 25:
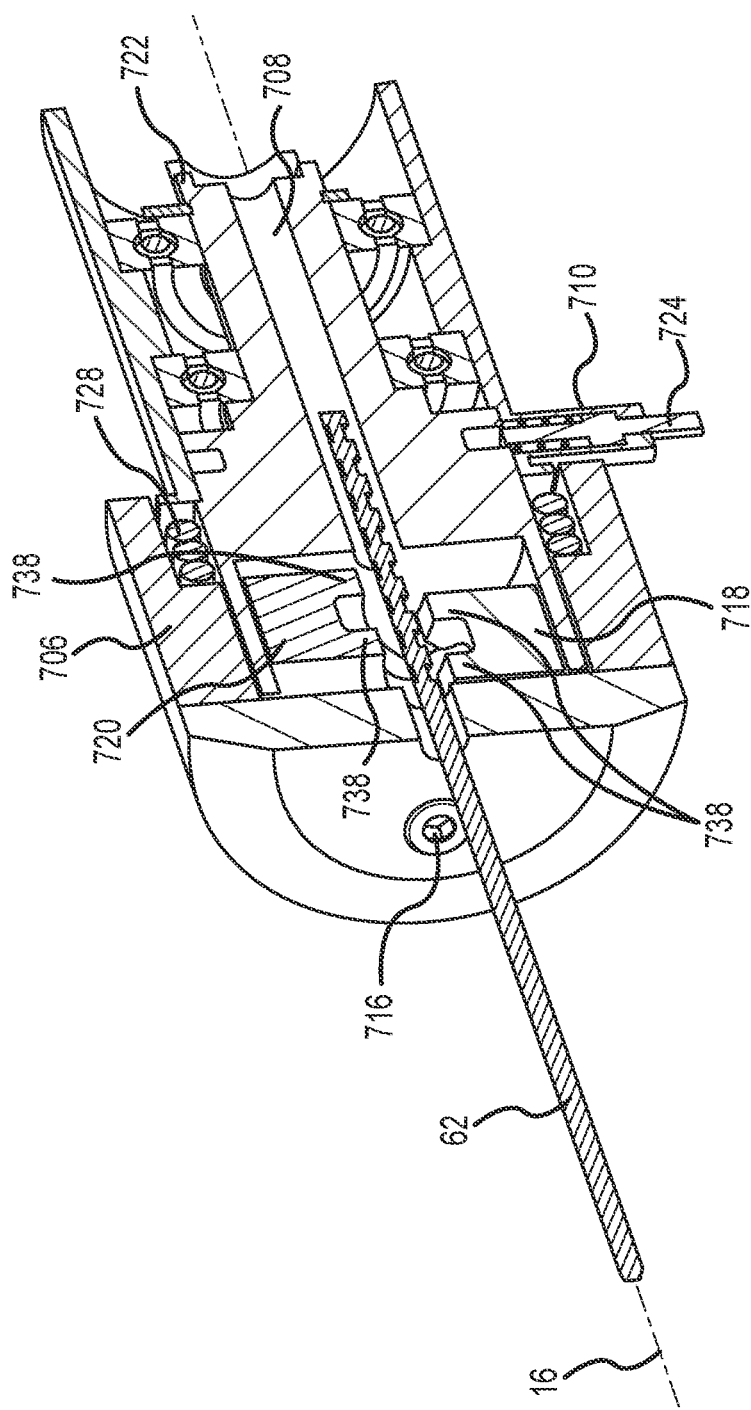
FIG. 25 depicts the embodiment of the chuck of FIG. 21 in cross section along a working axis thereof with an orthopedic implant placed relative to the chuck.
Figure 26:
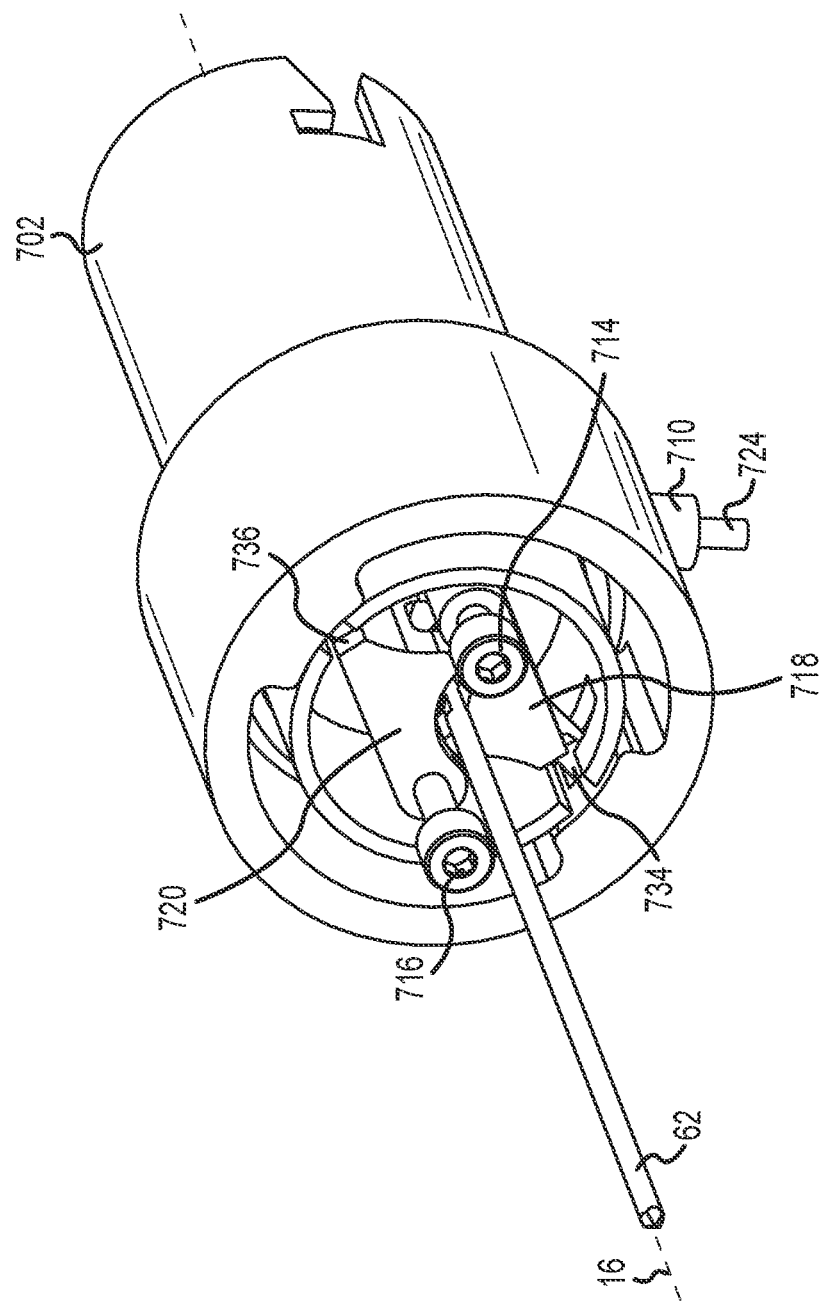
FIG. 26 depicts the embodiment of the chuck of FIG. 21 with a distal plate thereof removed to show an orthopedic implant engaged with jaw members of the chuck.
Figure 27:
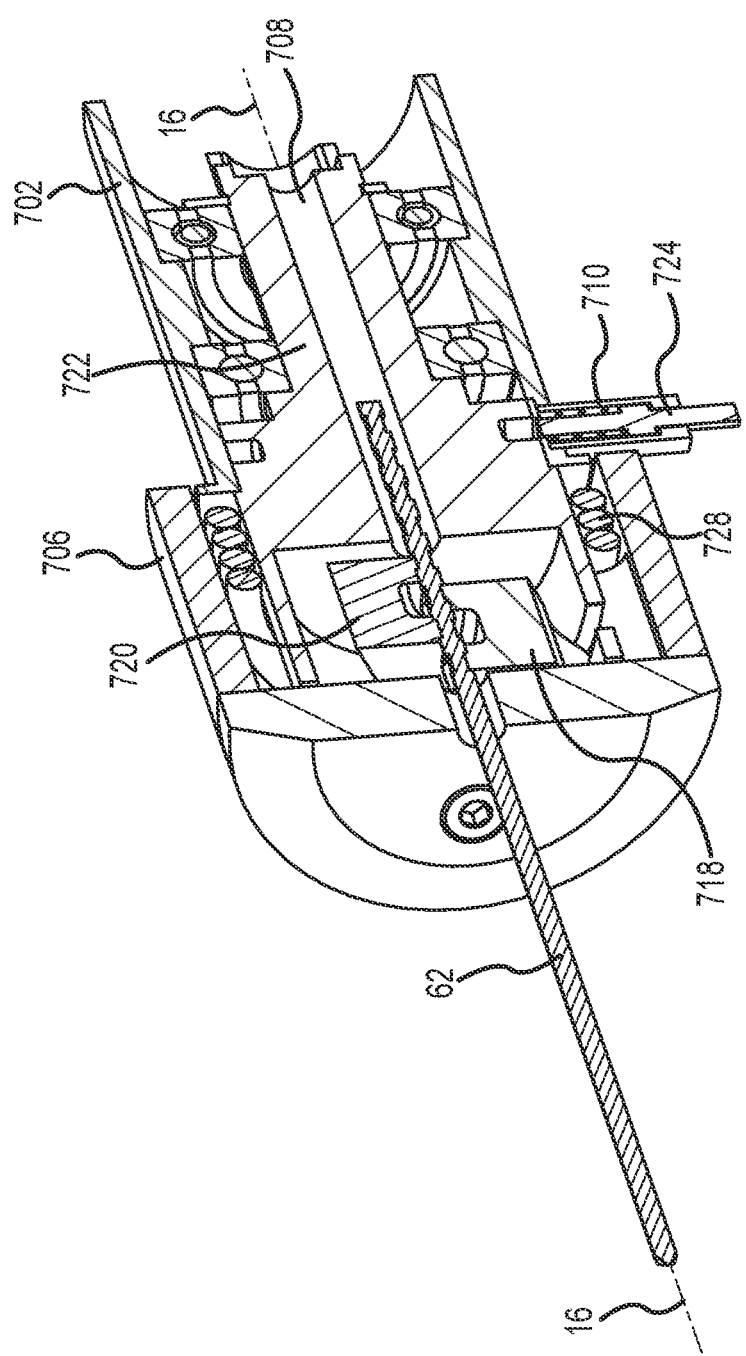
FIG. 27 depicts the embodiment of the chuck of FIG. 21 in cross section along a working axis thereof with an orthopedic implant engaged with the chuck.

For instance, FIG. 24 depicts a condition where the engagement control member 706 has been rotated relative to the chuck drive shaft 722 such that the cam surfaces 730 and 732 engage the follower portions 734 and 736 to move the jaw members 718 and 720 radially away from the work axis 16. In this regard, the orthopedic implant 62 may be inserted in the cannulated passage 708 as shown in FIG. 25. With further reference to FIGS. 26 and 27, the engagement control member 706 may be released. In turn, the bias member 728 may return the engagement control member 706 to a resting position such that the jaw members 718 and 720 are urged by the cam surfaces 730 and 732 acting on the follower portions 734 and 736 to cause the jaw members 718 and 720 to move radially inward toward and be biased toward the axis 16 under action of the biasing member 728 to engage an orthopedic implant in the cannulated passage 708.

One or more the plurality of index features 66 provided on the orthopedic implant 62 may be engaged by one or more of the jaw members 718 and 720. Specifically, the first and second jaw members 718 and 720 may include teeth members 738 correspondingly sized to engage the index feature 66 of an orthopedic implant 62. That is, the teeth members 738 may bear against the engagement surface 82 defined by the index feature 66 to engage the orthopedic implant 62. As the teeth members 738 may engage the engagement surface 82 of the orthopedic implant that is offset inward toward the working axis 16, the engagement feature 66 may define a shoulder that is engaged by the teeth members 738. As such, the interaction of the teeth member 738 with the orthopedic implant 62 may prevent relative axial movement between the orthopedic implant 62 and the chuck 700. However, force acting on the orthopedic implant 62 in a direction along the working axis 16 may still be imparted on the chuck 700 which may act upon the drive system 30 to bear against the for sensor 50 such that the force acting on the orthopedic implant 62 may be accurately measured.

As described above, a variety of different arrangements of indexing feature configurations may be provided on various embodiments of the orthopedic implant 62. In this regard, the jaw members 718 and 720, and specifically the teeth portions 738 may be sized correspondingly engage with the index features of a given orthopedic implant 62 to be used. As such, the jaw members 718 and 720 maybe offset relative to the working axis 16 such that a plurality of offset index features 66 at different positions along the working axis 16 of the orthopedic implant 62 (e.g., such as those shown in FIGS. 19, 19A, and 20) may be engaged by the teeth members 738. This may provide positive engagement to reduce the potential that the orthopedic implant 62 moves actually relative to the chuck 700 or slips rotationally relative to the chuck 700 during operation. However, other arrangements may be provided such as corresponding teeth portion 738 to engage an orthopedic implant as shown in FIG. 18 where the plurality of index member 66 are provided on coextensive portions of the length of the orthopedic implant 62 along the working axis 16 such the teeth 738 do not overlap.

With additional reference to FIGS. 31-35, another embodiment of a chuck 750 is shown. The chuck 750 may utilize a first jaw member 718 and a second jaw member 720 as described above. Also, the chuck 750 may include an engagement control member 706 that includes cam surfaces 730 and 732 to engage the follower portions 734 and 736 to move the jaw members 718 and 720 radially away from the work axis 16 as described above. However, the manner in which the engagement control member 706 is rotated may differ from that described above. In this regard, the chuck 750 may provide a means for engagement and disengagement of the orthopedic implant that is more ergonomic and provides easier movement to control the engagement and disengagement.

Specifically, the chuck 750 may include a lever handle 740 that is connected to the chuck body 702 via a pivot 742. A fork 744 extends on an opposite side of the pivot 742 from the lever handle 740. The fork 744 may engage pins 746 that couple the fork 744 to a control ring 748. In this regard, the chuck body 702 comprises slots 752 that accommodates movement of the control ring 748 distally and proximally in a direction along the working axis 16. Accordingly, movement of the lever handle 740 distally and proximally controls the movement of the control ring 748 distally and proximally along a direction corresponding to the working axis 16. Specifically, proximal movement of the lever handle 740 (i.e., in a direction toward the engagement portion 704) may result in distal movement of the control ring 748.

Figure 34:
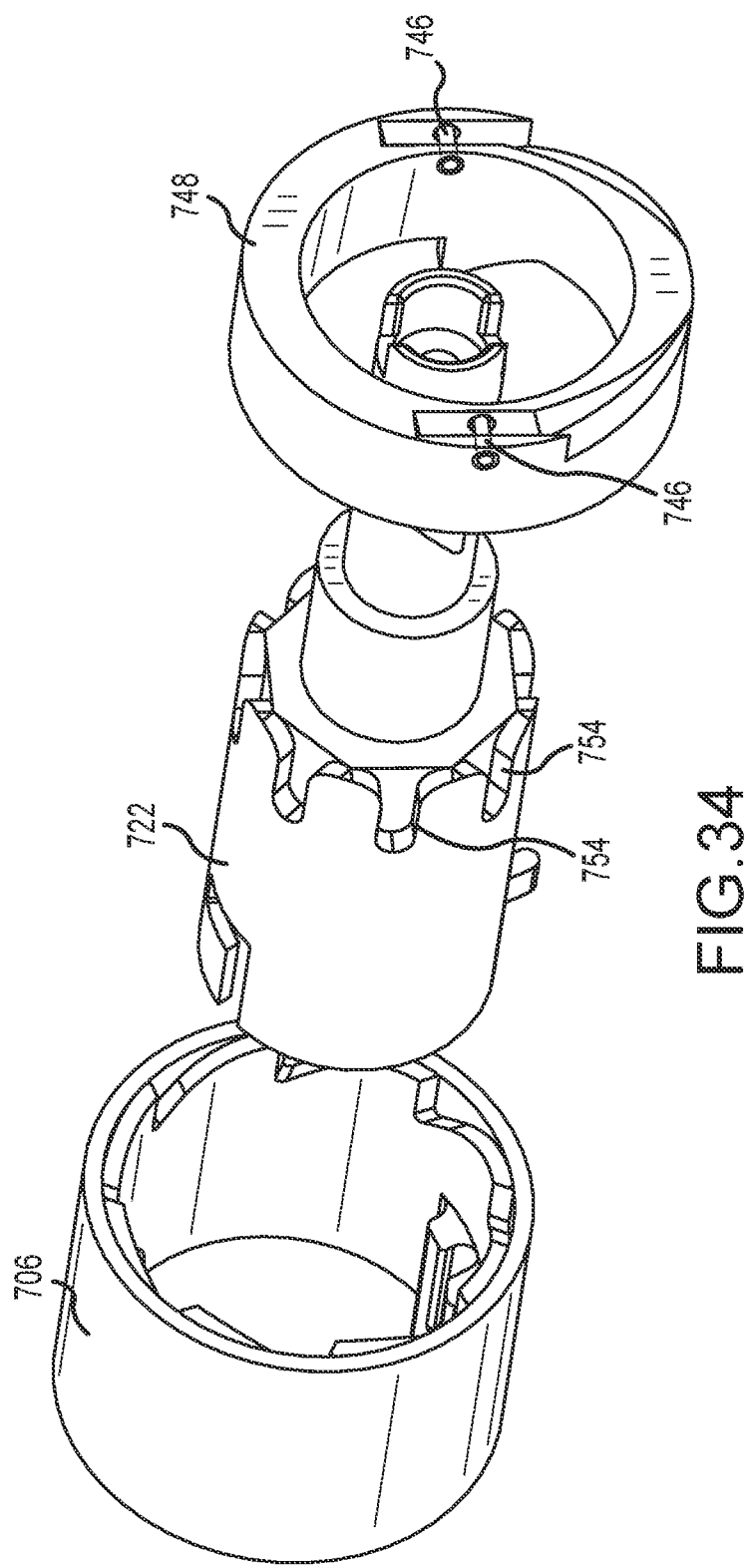
FIG. 34 depicts an exploded view of selected portions of the embodiment of the chuck of FIG. 31.
Figure 35:
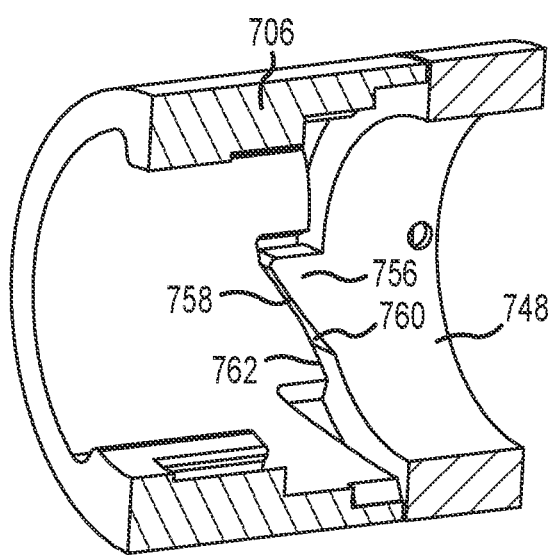
FIG. 35 depicts a cross sectional view of an engagement control member relative to a control ring in the embodiment of the chuck of FIG. 31.

With further reference to FIG. 34, which shows only the control ring 748, chuck drive shaft 722, and engagement control member 706, upon advancement of the control ring 748 distally, the pins 746 engaged with the control ring 748 may engage opposing notches 754 on the chuck drive shaft 722. This may result in rotationally locking of the chuck drive shaft 722.

Further distal advancement of the control ring 746 relative to the engagement control member 706 may result in a projection 756 on the control ring 746 engaging the engagement control member 706. Specifically, the projection 756 may comprise at least one cam surface 760 that contacts a corresponding ramped surface 762 of the control ring 706. The cam surface 760 may be arranged relative to the engagement control member 706 such that distal motion of the control ring 706 (e.g., under the influence of the lever handle 704) may cause the control member 706 to rotate about the working axis 16 so as to engage the jaw members 718 and 720 to move the jaw members 718 and 720 away from the working axis 16 as described above. As such, proximal movement of the lever handle 706 may result in distal movement of the control ring 706. This distal movement of the control ring 706 may result in the pins 746 being engaged with the notches 754 on the chuck drive shaft 722 to rotationally lock the drive shaft 722. The distal movement may also engage the projection 756 such that the cam surface 760 engages the ramped surface 762 of the engagement control member 706 to rotate the engagement control member 706 to move the jaw members 718 and 720. Upon release of the lever handle 704, the engagement control member 706 may return under the bias of the biasing member 728 as described above. Furthermore, the lever handle 704 may be engaged with biasing members 764 at the pivot 742 to return the lever handle 704 to a distal position so as to disengage the pins 746 from the notches 754 to release the chuck drive shaft 722 to allow rotation thereof.

With further reference to FIGS. 36A and 36B, a controller 146 is shown that may be utilized with the instrument 10. Specifically, as described above, the instrument 10 may have a displacement sensor 42 for outputting a signal indicative of the relative displacement of a working portion (e.g., a leading edge 10a of an orthopedic implant 62). Also, the instrument 10 may have a force sensor 50 for measurement of the force acting on the working portion (e.g., orthopedic implant 62) axially along the working axis 16. The instrument 10 may include a telemetry cable 174 in operative communication with the displacement sensor 42 and the force sensor 50. The telemetry cable 174 may have a connector 172 that may interface with a data port 170 of the controller 146. While a telemetry cable 174 is shown for interfacing with the controller 146, other approaches are possible for relay of data from the instrument 10 to a controller 146 such as, for example, by way of wireless telemetry via a wireless protocol such as Bluetooth, IEEE 802.11, or the like. Furthermore, the controller 146 may not be a separate unit, but may be integrated into the instrument 10.

As depicted, the controller 146 may include a touchscreen interface 152 for use by a user to interface with the controller 146. The interface 146 may allow a user to set a diameter of the working portion (e.g., orthopedic implant 62) at a diameter selection 160. Moreover, the rotational speed of the instrument may be displayed and/or controlled at the speed selection 162. An operation mode may be selected or input at the mode selection 150 as will be described in greater detail below. Also, the instrument direction may be selected or input at the direction selection 164. In an embodiment, the instrument 10 may measure a depth of a bore. This may be output in the length measurement output 166. Also, the controller 146 may have a reset selection 153 to allow for resetting the instrument (e.g., for establishing a reference point for the displacement sensor 42 and/or calibrating the force sensor 50). While a reset selection 153 may be provided on the controller 146, the reset selection 153 may be triggered by use of a first trigger 90 and a second trigger 92 of the instrument 10. For instance, in normal operation, actuation of the first trigger 90 may result in operation of the instrument 10 in a first direction (e.g., clockwise relative to the working axis 16). Actuation of the second trigger 92 may result in operation of the instrument 10 in an opposite direction (e.g., anticlockwise relative to the working axis 16). Actuation of the first trigger 90 at the same time as the second trigger 92 may send a reset signal to the controller 146 to zero a depth measurement (e.g., to establish a reference point). Actuation of the first trigger 90 simultaneously with the second trigger 92 may also sequence the controller 146 (e.g., to indicate a new bore or implant is to be utilized). The controller 146 may also display administrative data 168 (e.g., regarding an operation, patient, instrument status information, etc.).

In an embodiment, the controller 146 may determine that an implant 62 is released such that the instrument 10 is withdrawn distally relative to the implant 62. For example, the instrument 10 may be equipped with a sensor to detect disengagement of the orthopedic implant 62. For instance, a wired or wireless sensor may be disposed in the chuck such that the sensor may detect when various components of the chuck are in a position to disengage an orthopedic implant.

Such a sensor may provide an output to the controller. Additionally or alternatively, the controller 146 may include a selection for input of an indication that the orthopedic implant 62 is released. In any regard, upon release and retraction of the instrument 10 from the orthopedic implant 62, any measured relative displacement may be ignored (e.g., so as not to account for advancement or retraction of the orthopedic implant from the substrate into which it is advanced). In this regard, upon reengagement of the implant 62, further advancement may be accurately measured by the displacement sensor 42. The spacing of the indexing features 66 may be such that adjacent indexing features 66 are located nearer to each other than the measureable distance of the displacement sensor 42 such that the displacement sensor may accurately measure any subsequent advancement of the implant 62 upon being reengaged after withdrawing the instrument 10 distally upon disengagement.

Figure 37:
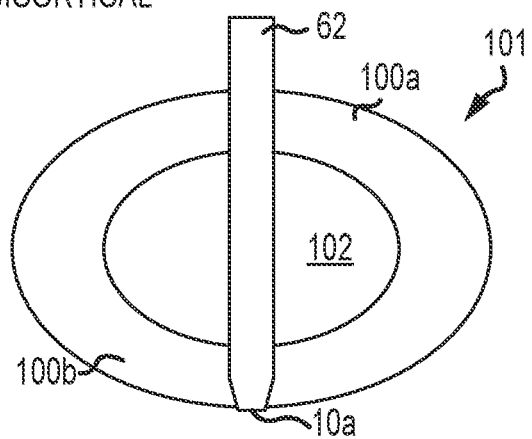
FIG. 37 depicts a cross sectional view of a bone with an orthopedic implant placed using a bicortical mode of operation of an instrument.

As mentioned briefly above, the controller 146 may be configured to perform in various different modes using the mode selection 150. As an example, the different modes of operation may correspond with different relative placements of the leading edge 10a of the orthopedic implant 62 relative to the anatomy of a patient. Different placements of an orthopedic implant are depicted in FIGS. 37, 38, 39, and 40. For instance, a bicortical bone cross-section such as those depicted in FIGS. 37-40 may include a hard outer cortex that surrounds a medullary layer 102. In this regard, in bicortical operation is depicted in FIG. 37, the leading edge 10a of the orthopedic implant 62 may be advanced through a first portion of the hard outer cortex 100a, the medullary layer 102, and a second portion of the hard outer cortex 100b. In turn, when the leading edge 10a breaches the exterior of the second portion of the hard outer cortex 100b, the instrument 100 may be arrested such that the orthopedic implant 62 is placed as depicted in FIG. 37 where the leading edge 10a just breaches the entire bicortical length of the bone. Bicortical operation of the instrument 10 is generally described in U.S. Pat. No. 6,665,948 which is incorporated by reference herein.

Figure 38:
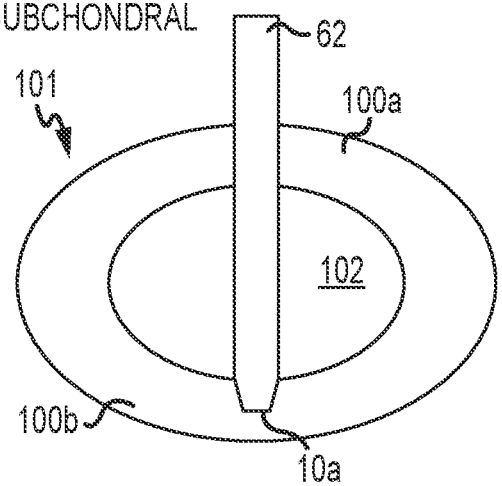
FIG. 38 depicts a cross sectional view of a bone with an orthopedic implant placed using a subchondral mode of operation of an instrument.

FIG. 38 depicts another mode of operation corresponding to subchondral placement of the orthopedic implant 62. In this regard, the leading edge 10a of the orthopedic implant 62 is advanced through the first portion of hard outer cortex 100a, the medullary layer 102, and a portion of the second portion of hard outer cortex 100b. In this regard, the instrument 10 may be arrested when the leading edge 10a is embedded in the second portion of hard outer cortex 100b as shown in FIG. 38.

Figure 39:
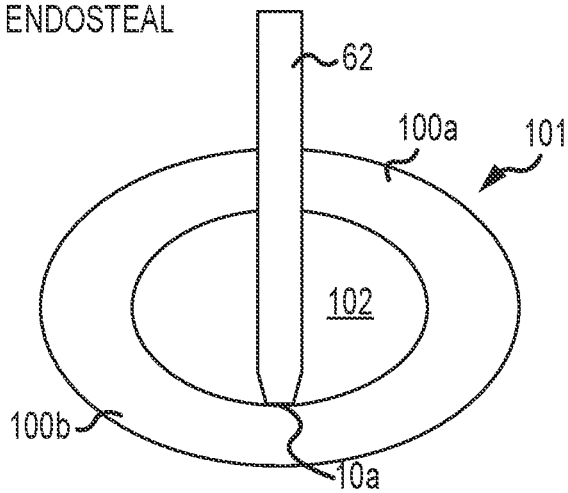
FIG. 39 depicts a cross sectional view of a bone with an orthopedic implant placed using an endosteal mode of operation of an instrument.

FIG. 39 depicts another mode of operation corresponding to an endosteal placement of the orthopedic implant 62. In this regard, the leading edge 10a may be advanced through the first portion of hard outer cortex 100a and through the medullary layer 102. The instrument 10 may be arrested when the leading edge 10a reaches the second portion of hard outer cortex 100b such that the leading edge 10a is disposed at the interface of the medullary layer 102 and the second portion of hard outer cortex 100b.

Figure 40:
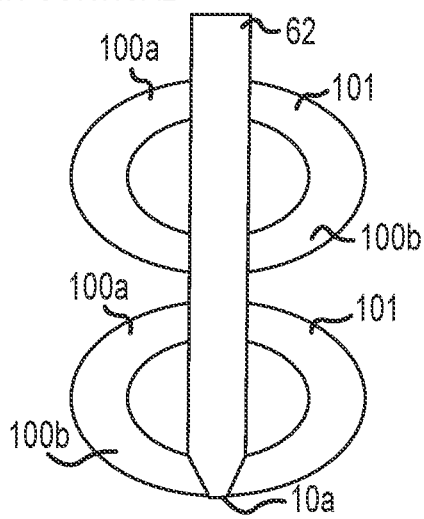
FIG. 40 depicts a cross sectional view of a plurality of bones with an orthopedic implant placed using a multi-cortical mode of operation of an instrument.

FIG. 40 depicts another mode of operation corresponding to multi-cortical placement of the orthopedic implant 62. In this mode, the leading edge 10a of the orthopedic implant 62 is advanced through a plurality of bones 101. In this regard, the number of bones through which the orthopedic implant 62 is to be advanced may be set such that instrument 10 is arrested when the leading edge 10a of the orthopedic implant 62 breaches the second portion of hard outer cortex 100b of the last bone 101 through which the orthopedic implant 62 is to be advanced. Multi-cortical placement of the implant 62 may involve setting occurrence flags that may at least in part be based on the number of bones though which the orthopedic implant 62 is to pass. For instance, if two bones are to be drilled through, the fourth occurrence of the passing of the leading edge 10a from a first medium into a second medium having a lower density may indicate completion of the operation. Also, while a bicortical placement is shown in FIG. 40, the multi-cortical mode may have submodes that allow for bicortical, subchondral, or endosteal placement through multiple bones using identification techniques to place the orthopedic implant 62 in the last bone in the series of bones through which the orthopedic implant 62 is to be advanced. That is, the measurement system 40 may monitor penetration through n−1 bones where n is the number of the last bone in which the orthopedic implant 62 is to be placed. For the nth bone, any of the following specific techniques may be used for bicortical, subchondral, or endosteal placement of the orthopedic implant 62 in the last bone.

Any of the foregoing placements may correspond with modes of operation of the instrument 10. For instance, selection of a mode corresponding to any one of the foregoing placements may be utilized by selection via the mode selection 150 of the controller 146. As such, when a corresponding one of the modes is selected, the controller 146 may be operative to control operation of the measurement system 40 so as to arrest the instrument 10 when the leading edge 10a of the orthopedic implant 62 reaches the placement designated for the mode or may output an alarm or take some other action. In this regard, any one of a variety of approaches may be utilized to determine when the orthopedic implant 62 reaches the various placements described above. In this regard, various embodiments of methods are described herein.

For instance, determination of the position of the leading edge 10a of the orthopedic implant 62 relative to the structure of a bone 101 may be determined using signals output from force and/or displacement sensors of a measuring system 40 as described in the '948 patent incorporated by reference in its entirety above. That is, as the leading edge 10a passes through the various interfaces of the bone structure 101, these interfaces may be detected based on signals from the force sensor 50 and displacement sensor 42. For instance, when the leading edge 10a passes from the first portion of hard cortex 100a to the medullary layer 102, the working portion 16 may experience a decrease in the force sensed by the force sensor 50 and an increase in acceleration. The decrease in the force may be determined by taking the derivative of the signal output from the force sensor 50. Specifically, the derivative of the signal output from the force sensor 50 may become negative, indicating a negative rate of change of the force applied. Alternatively, a local minimum of a second derivative of the force may be determined that corresponds to a reduction in the force acting on the working portion 16. For instance, a second derivative of the force signal may be taken and the local minimum of the second derivative of the force signal may be determined using any appropriate computational approach to determine such a state in the force signal. Additionally, taking the second derivative of the output from the displacement sensor 42 may provide a signal indicative of the acceleration. This technique may also be used to determine when the working portion 16 passes through the second portion 100b of hard cortex 100. This may be the first occurrence of a decrease in force and increase in acceleration in the case of unicortical operation or the second occurrence in the case of bicortical operation.

Moreover, it may be determined when the leading edge 10a contacts the second portion 100b of cortex 100 after passing through the medullary layer 102. In this regard, a decrease in acceleration and an increase in force as measured from the displacement sensor 42 and the force sensor 50 may be utilized to determine the second portion 100b of cortex 100 has been contacted for endosteal placement. For subchondral placement, a given displacement offset from the contacting of the second portion 100b of the cortex 100 may be used to advance the leading edge 10a of the orthopedic implant 62 partially into the second portion 100b of cortex 100.

Figure 41:
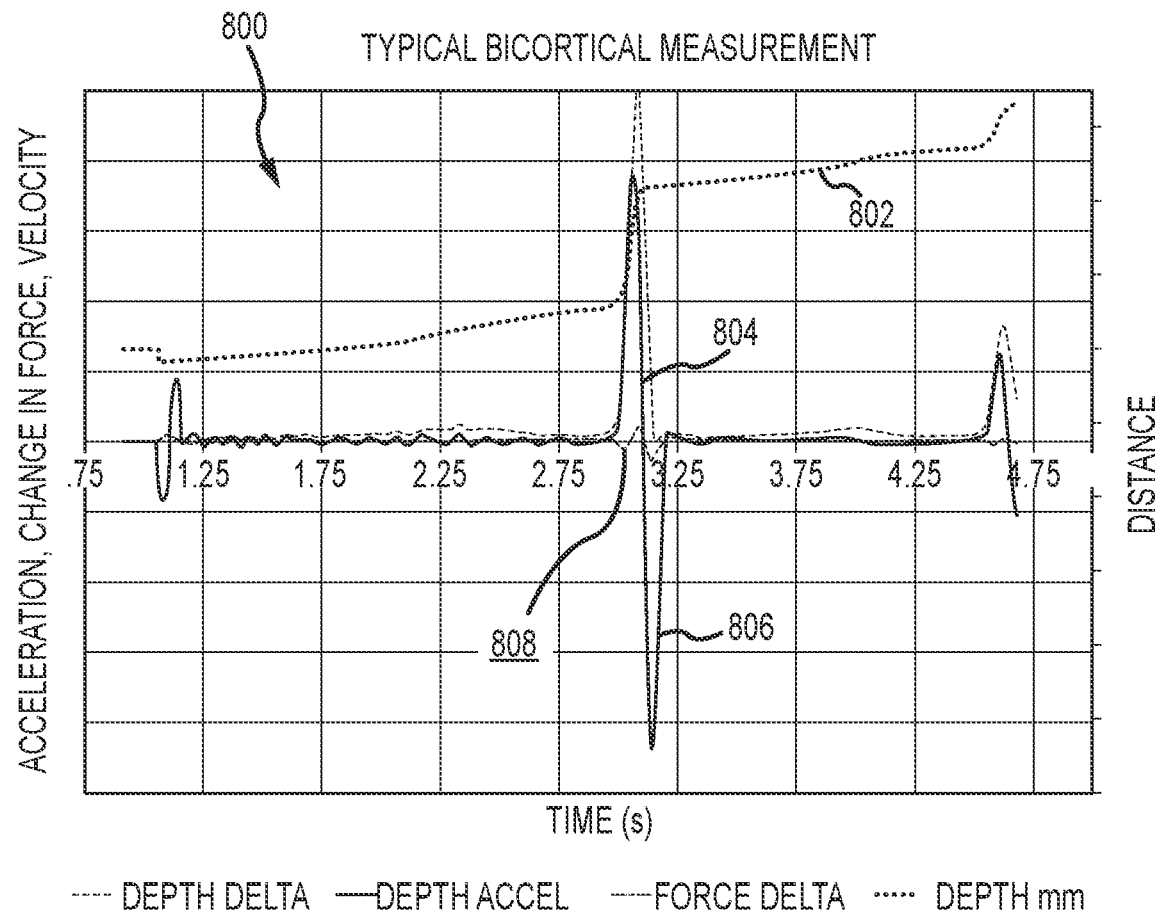
FIGS. 41 and 42 depict a plot of various signals measured or derived in an embodiment of operation of the instrument that include a change in force measure as measured by a force sensor of the measurement system.
Figure 42:
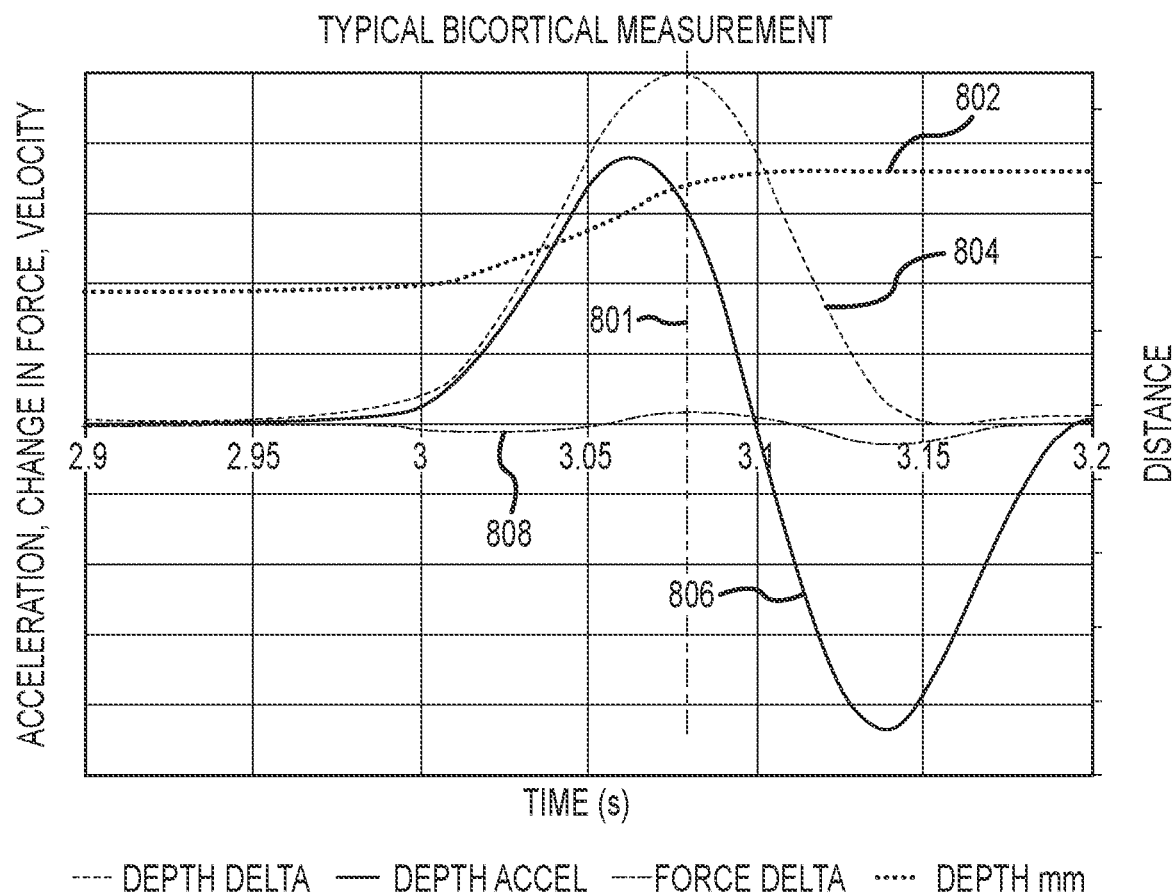

Such a context is depicted in FIGS. 41 and 42. FIG. 41 depicts a plot 800 of various sensor outputs and/or calculated signals during a normal bicortical pass of a leading edge 10a of an orthopedic implant 62 through a bone 101 of a patient. The plot 800 includes a displacement signal 802. The displacement signal 802 may be a directly measured signal from a displacement sensor 42 of a measurement system 40. Alternatively, the displacement signal 802 may be derived from another sensor (e.g., as a second integral of a signal from an accelerometer or the like). The plot 800 also includes a velocity signal 804, which may be measured directly or derived from a displacement sensor or an accelerometer. The plot 800 also includes an acceleration signal 806. The acceleration signal 806 may be measured (e.g., using an accelerometer or the like) or may be derived from the displacement signal 802 (e.g., as a second derivative of the displacement signal 802). As discussed above, the velocity signal 804 may be derived from either the displacement signal 802 (e.g., as a first derivative thereof) or from the acceleration signal 806 (e.g., as a first integral thereof). Moreover, FIG. 41 may include a force signal 808 representative of a change in force as measured by a force sensor 50. In this regard, the force signal 808 may not depict an actual force measure, but rather a first derivative of actual force. FIG. 42 shows an enlarged portion of the plot 800 in a region of interest around the interfaces of the cortices.

As best seen in FIG. 42, the contact between the leading edge 10a and interface of the medullary layer 102 and the second portion 100b of cortex 100 occurs between 3.05 seconds and 3.1 second in the plot 800 at the interface 801. This interface 801 coincides with the point at which the force signal 808 (representing the first derivative of the measured force) experiences a maximum (as may be measured by determining when a second derivative of the measured force is positive). The interface 801 may also coincide with a reduction in the acceleration signal 806. As such, when the force signal 808 is at a local maximum that coincides with the acceleration being negative, the interface 801 may be determined.

Additionally, and as described in U.S. patent application Ser. No. 14/845,602, incorporated by reference above, placement of the orthopedic implant 62 may be based solely on a single sensor such as a displacement sensor 42 or an acceleration sensor provided with the measurement system 40. In this regard, whether an acceleration sensor or a displacement sensor 42 is used, the resulting single signal may be processed to arrive at a displacement signal, a velocity signal, and an acceleration signal. In turn, these complimentary signals may be used to determine when the leading edge 10a passed through an interface. For instance, as the leading edge 10a passes from the first portion 100a of hard cortex 10 to the medullary layer 102, there may be a simultaneous positive displacement, velocity, and acceleration as determined from the displacement signal, velocity signal, and acceleration signal. This may be indicative that the leading edge 10a has passed from the hard outer cortex 100a to the medullary layer 102. A similar condition may occur at a second occurrence of positive displacement, velocity, and acceleration as the leading edge 10a passes from the second portion 100b of hard cortex 100 to the medium surrounding the bone 101. As such, the bicortical or unicortical mode may be facilitated whereby either a second occurrence or a first occurrence, respectively, of positive displacement, velocity, and acceleration occur simultaneously.

This approach using a single sensor to arrive at a displacement, velocity, and acceleration may also be used to determine when the leading edge 10a contacts the second portion 100b of hard cortex 100 for support of an endosteal mode. Specifically, as the leading edge 10a is advanced through the medullary layer 102, the orthopedic implant 62 may experience positive displacement, positive velocity, and a negative acceleration when the second portion 100b of hard cortex 100 is contacted. That is, contact of the leading edge 10a with the second portion of hard cortex 100b may be detected with positive displacement, positive velocity, and negative acceleration. As such, an endosteal mode of operation may be supported using a single sensor for generation of a displacement signal, velocity signal, and acceleration signal. Furthermore, as described above, subchondral placement of the orthopedic implant 62 may be facilitated by advancing the leading edge 10a a predetermined distance beyond detection of the leading edge 10a passing from the medullary layer 102 to the second portion 100b of hard cortex 100. This predetermined distance may be controlled by selection of a bone type, a value input by a user, or a calculated value based on measured values of the first portion 100a of hard cortex 100 and/or medullary layer 102 thickness.

Figure 43:
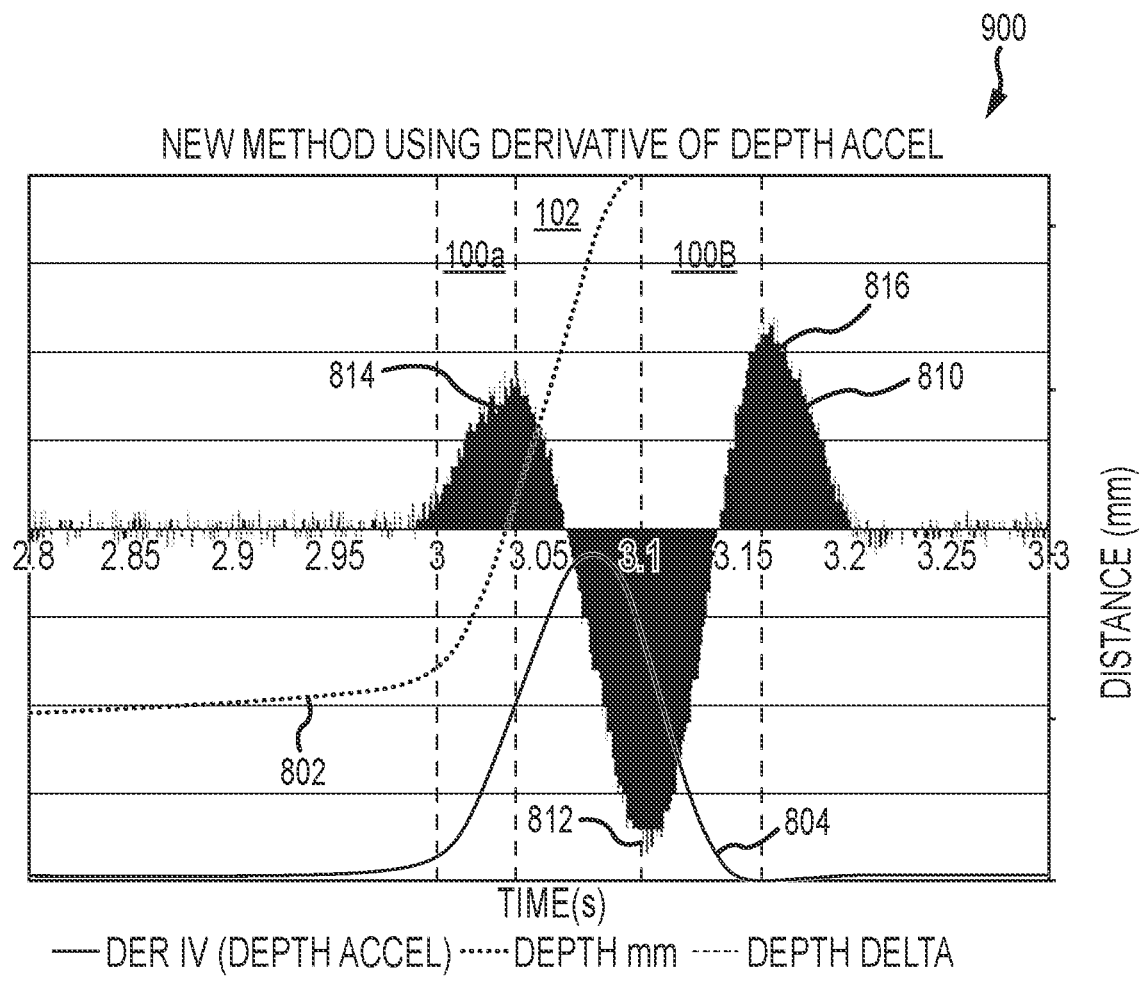
FIGS. 43 and 44 depict a plot of various signals including a derivative signal derived in an embodiment of an operation of the instrument that are derived from a single sensor.
Figure 44:
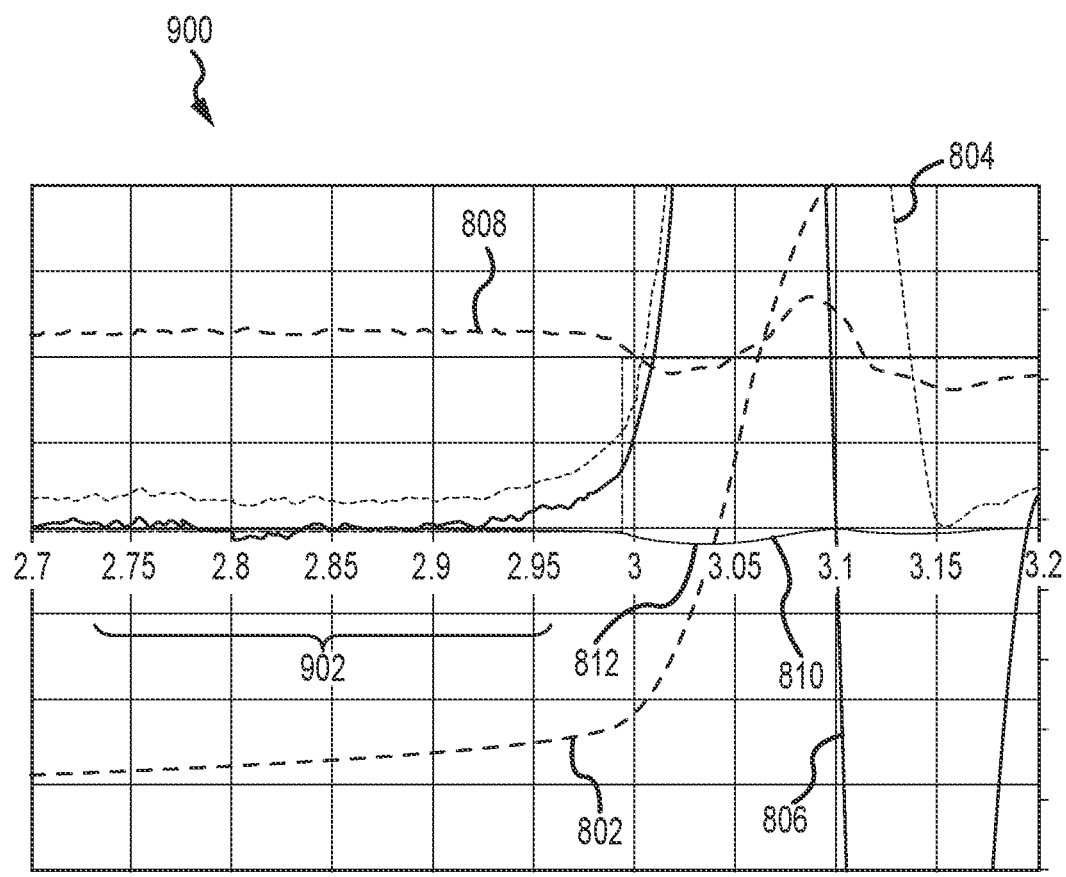

FIGS. 43 and 44 reflect a plot 900 reflecting signals that are measured or determined utilizing a single displacement or acceleration sensor. In FIG. 43, a displacement signal 802 and a velocity signal 804 may be provided. Furthermore, a derivative signal 810 representative of the derivative of an acceleration signal may be provided. This signal 810 may indicate changes of inflection 814 and 816 where the rate of change of inflection is "concave down" corresponding with a maximum rate of change of positive acceleration. As such, these inflection points 814 and 816 may be indicative of the passing of the leading edge 10a of the orthopedic implant 62 passes from a relatively hard medium to a relatively soft medium. In this regard, inflection point 814 may be indicative of the leading edge 10a passing from the first portion 100a of hard cortex 100 to the medullary layer 102 and inflection point 816 may be indicative of the passing of the leading edge 10a passing from the second portion 100b of the cortex 100 into the medium surrounding the bone 101. Moreover, a local minimum at inflection point 812 of the derivative signal 810 may indicate a maximum deceleration of the leading edge 10a indicating contact with the second cortex 100b. In any of these instances, determination of the local minimum and/or maximum of the derivative signal 810 may be determined using any signal processing known in the art. For instance, a further derivative may be taken of the derivative signal 810 for use in determining the local minimums and/or maximums. This signal would be the second derivative of the acceleration signal. In turn, the derivative signal 810 may be utilized to determine all three interfaces of interest in a bicortical operation. As such, the derivative signal may be used for bicortical, endosteal, and subchondral modes.

With further reference to FIG. 44, the inflection point 812 of the derivative signal 810 may coincide with the acceleration signal 808 passing through zero (i.e., the acceleration passing from positive acceleration to negative acceleration). This may not always be true, as demonstrated in FIG. 44. For example, there is a region 902 in which the acceleration signal 808 passes over the zero axis several times corresponding with increases and decreases in acceleration. However, the minor changes in acceleration direction may not occur with a large enough rate of change to be detectable in the derivative signal 810. However, the inflection point 812 in FIG. 44 does indicate the interface between a relatively soft layer and a relatively hard layer as the rate of change (negative) of the acceleration signal 810 is a maximum as reflected in the inflection point 812 of the derivative signal 810. As such, a filtering approach may be applied such that a rate of change of the acceleration signal 810 may be required to be greater than a threshold value to be used to indicate a detected interface.

As may be appreciated, various ones of the foregoing embodiments of chucks may be utilized to dispose either a smooth walled orthopedic implant or an orthopedic implant having a plurality of indexing features disposed along the side wall thereof. In this regard, the distal portion of the orthopedic implant has not been discussed in the foregoing embodiments and can generally be among any of the available distal configurations, and to orthopedic implants. However, it is presently recognized that in certain contexts it may be difficult for a measurement system 40 as described herein to accurately discern the position of an orthopedic implant as it moves through the various structures of a bone of a patient. For instance, small diameter orthopedic implants and/or orthopedic implants that are slowly advanced relative to the bone may not provide sufficient force, acceleration, and/or other displacement based values sufficient for discerning the placement of the orthopedic implant.

Figure 47:
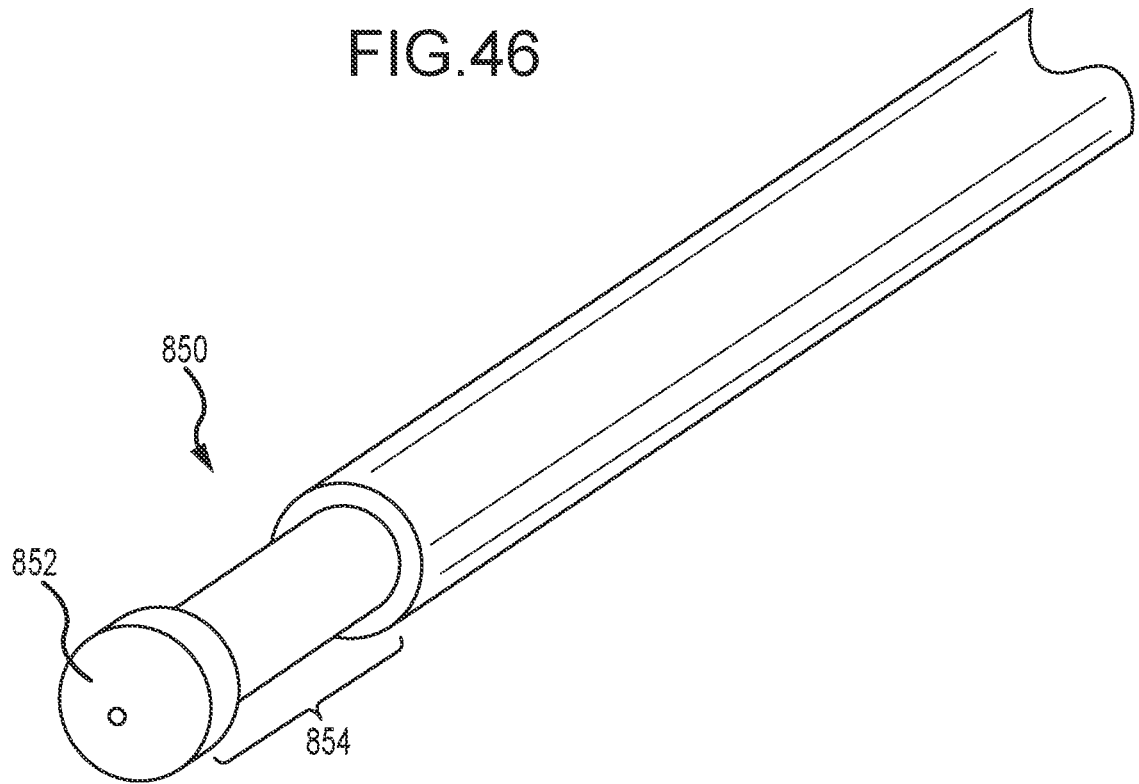
FIGS. 47-49 depict the distal end of embodiment of an orthopedic implant that may be utilized in connection with an instrument as described herein.
Figure 48:
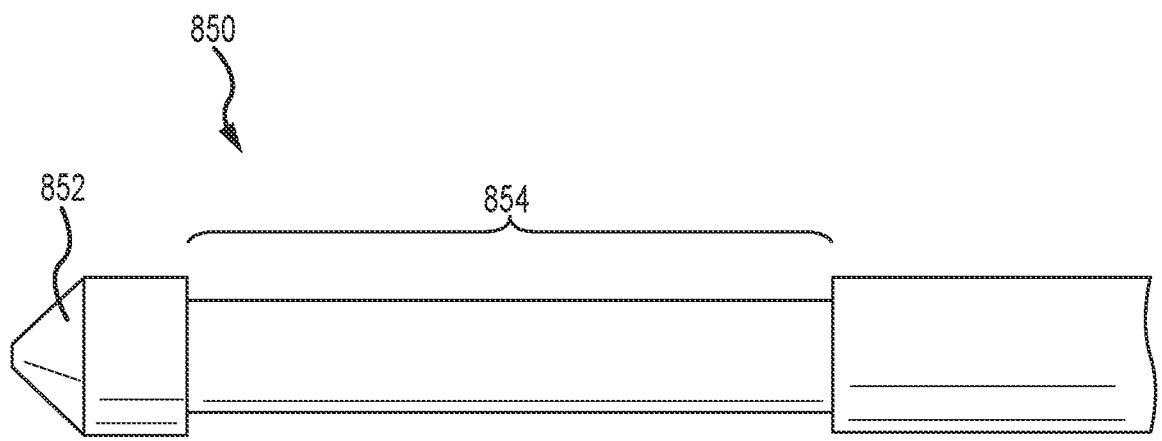
Figure 49:
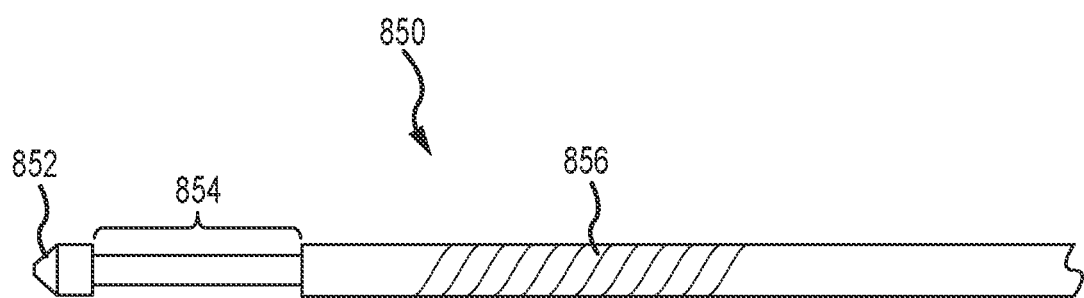

In this regard, an embodiment of an orthopedic implant is depicted in FIGS. 47-49 that may be utilized to assist in determination of the placement of an orthopedic implant 850 using a measurement system 40 as described herein. Specifically, the orthopedic implant 850 may have a tapered or conical distal tip 852. Specifically, the conical distal tip 852 may be a relatively shallow taper. Moreover, the distal tip 852 may be fluted. The fluting of the distal tip 852 may be a high helix angle. This may increase the resulting forces required to induce movement of the orthopedic implant 850 through the bone of the patient, thus assisting in the determination of the forces and/or displacement values associated with the advancement. Furthermore, the orthopedic implant 850 may include a relief portion 854 disposed proximally to the distal end 852 of the orthopedic implant a 50. The relief portion 854 may include a stepped in diameter portion of the orthopedic implant 850. That is, the relief portion 854 may comprise a portion of the orthopedic implant having a diameter smaller than that of the remaining portion of the orthopedic implant 850. The relief portion 854 may reduce thermal load on the orthopedic implant he 50 as it is advanced relative to the bone of the patient. This may assist in reducing trauma to the bone tissue disposed proximally to the distal end 852 as the orthopedic implant 850 is advanced relative to the bone. The orthopedic implant 850 may further include a helical portion 856 proximal to the relief portion 854. The helical portion 854 may include fluted reliefs within the side wall of the orthopedic implant 850 and/or threads that extend externally to the side wall of the orthopedic implant 850. In either regard, it has been found that the helical portion 856 may be operative to gain purchase on a proximal portion of a cortex of a bone, thus assisting in driving the distal tip 852 of the orthopedic implant 850 relative to a distal portion of cortex of the bone. That is, the helical portion 854 may assist in advancing the orthopedic implant 850 distally into the bone of the patient.

While the invention has been illustrated and described in detail in the drawings and foregoing description, such illustration and description is to be considered as exemplary and not restrictive in character. For example, certain embodiments described hereinabove may be combinable with other described embodiments and/or arranged in other ways (e.g., process elements may be performed in other sequences). Accordingly, it should be understood that only the preferred embodiment and variants thereof have been shown and described and that all changes and modifications that come within the spirit of the invention are desired to be protected.

What is claimed is:

1. A method of advancing an orthopedic implant into a bone of a patient, comprising:
    engaging the orthopedic implant with a chuck of an instrument to restrict axial movement of the orthopedic implant relative to the chuck along a working axis of the chuck;
    first advancing the orthopedic implant distally into the bone of the patient a first distance by imparting rotational motion to the chuck when engaged with the orthopedic implant;
    first measuring the first distance using a displacement sensor of a measurement system associated with the instrument;
    releasing the orthopedic implant from the chuck;
    retracting the instrument relative to the orthopedic implant in a proximal direction opposite of the direction of the advancing;
    reengaging the orthopedic implant with the chuck of the instrument to restrict axial movement of the orthopedic implant relative to the chuck along a working axis of the chuck; and
    second advancing the orthopedic implant distally into the bone of the patient a second distance by imparting rotational motion to the chuck; and
    second measuring the second distance using the displacement sensor of the measurement system associated with the instrument.

2. The method of claim 1, further comprising:
    summing the first distance and the second distance at the measurement system.

3. The method of claim 2, further comprising:
    determining that the orthopedic implant is released from the chuck; and
    disregarding any change in displacement of the displacement sensor when the orthopedic implant is released from the chuck.

4. The method of claim 3, wherein a sensor is provided relative to the chuck to determine the orthopedic implant is released from the chuck.

5. The method of claim 3, wherein the determining is based on a user input provided to the measurement system.

6. The method of claim 1, wherein the engaging comprises the chuck engaging the orthopedic implant at a first indexing feature of a plurality of indexing features and the reengaging comprises the chuck engaging the orthopedic implant at a second indexing feature of the plurality of indexing features that is proximal to the first indexing feature.

7. The method of claim 6, wherein the engaging occurs in response to the first advancing, the reengaging occurs in response to the second advancing, and the releasing occurs in response to the retracting.

\* \* \* \* \*